United States Patent
Huang et al.

(10) Patent No.: US 10,433,742 B2
(45) Date of Patent: Oct. 8, 2019

(54) MAGNETOENCEPHALOGRAPHY SOURCE IMAGING FOR NEUROLOGICAL FUNCTIONALITY CHARACTERIZATIONS

(71) Applicant: The Regents of the University of California, Oakland, CA (US)

(72) Inventors: Ming-Xiong Huang, San Diego, CA (US); Roland R. Lee, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 878 days.

(21) Appl. No.: 14/910,218

(22) PCT Filed: Aug. 5, 2014

(86) PCT No.: PCT/US2014/049824
§ 371 (c)(1),
(2) Date: Feb. 4, 2016

(87) PCT Pub. No.: WO2015/021070
PCT Pub. Date: Feb. 12, 2015

(65) Prior Publication Data
US 2016/0157742 A1 Jun. 9, 2016

Related U.S. Application Data

(60) Provisional application No. 61/862,511, filed on Aug. 5, 2013.

(51) Int. Cl.
*A61B 5/04* (2006.01)
*A61B 5/00* (2006.01)
*A61B 5/055* (2006.01)

(52) U.S. Cl.
CPC .......... *A61B 5/04008* (2013.01); *A61B 5/04* (2013.01); *A61B 5/04001* (2013.01);
(Continued)

(58) Field of Classification Search
CPC ......... A61B 5/04; A61B 5/05; A61B 5/04001; A61B 5/04004; A61B 5/04005;
(Continued)

(56) References Cited

U.S. PATENT DOCUMENTS

| | | | |
|---|---|---|---|
| 6,697,660 B1 * | 2/2004 | Robinson | A61B 5/04005 324/248 |
| 2009/0285463 A1 | 11/2009 | Otazo et al. | |

(Continued)

FOREIGN PATENT DOCUMENTS

| | | | | |
|---|---|---|---|---|
| WO | WO-2012006129 A2 * | 1/2012 | | A61B 5/0476 |
| WO | 2012162569 A2 | 11/2012 | | |

OTHER PUBLICATIONS

Huang, Ming-Xiong, Sharon Nichols, Ashley Robb, Annemarie Angeles, Angela Drake, Martin Holland, Sarah Asmussen et al. "An automatic MEG low-frequency source imaging approach for detecting injuries in mild and moderate TBI patients with blast and non-blast causes." Neuroimage 61, No. 4 (2012): 1067-1082.*

(Continued)

*Primary Examiner* — Carolyn A Pehlke
(74) *Attorney, Agent, or Firm* — Perkins Coie LLP

(57) ABSTRACT

Methods, systems, and devices are disclosed for implementing magnetoencephalography (MEG) source imaging. In one aspect, a method includes determining a covariance matrix based on sensor signal data in the time domain or frequency domain, the sensor signal data representing magnetic-field signals emitted by a brain of a subject and detected by MEG sensors in a sensor array surrounding the brain, defining a source grid containing source locations within the brain that generate magnetic signals, the source locations having a particular resolution, in which a number of source locations is greater than a number of sensors in the sensor array, and generating a source value of signal power for each location in the source grid by fitting the selected (Continued)

sensor covariance matrix, in which the covariance matrix is time-independent based on time or frequency information of the sensor signal data.

21 Claims, 19 Drawing Sheets

(52) U.S. Cl.
CPC .......... *A61B 5/04005* (2013.01); *A61B 5/055* (2013.01); *A61B 5/7203* (2013.01); *A61B 5/7235* (2013.01); *A61B 5/04009* (2013.01)

(58) Field of Classification Search
CPC . A61B 5/04008; A61B 5/04009; A61B 5/055; A61B 5/7235; G01R 33/00; G01R 33/326
USPC ......................................................... 600/409
See application file for complete search history.

(56) References Cited

U.S. PATENT DOCUMENTS

2011/0313274 A1  12/2011  Subbarao
2013/0096408 A1   4/2013  He et al.

OTHER PUBLICATIONS

Huang, Ming-Xiong, Anders M. Dale, Tao Song, Eric Halgren, Deborah L. Harrington, Igor Podgorny, Jose M. Canive, Stephen Lewis, and Roland R. Lee. "Vector-based spatial-temporal minimum L1-norm solution for MEG." NeuroImage 31, No. 3 (2006): 1025-1037.*

Huang, Ming-Xiong, Rebecca J. Theilmann, Ashley Robb, Annemarie Angeles, Sharon Nichols, Angela Drake, John D'Andrea et al. "Integrated imaging approach with MEG and DTI to detect mild traumatic brain injury in military and civilian patients." Journal of neurotrauma 26, No. 8 (2009): 1213-1226.*

Baldissera, F. et al., "Afferent excitation of human motor cortex as revealed by enhancement of direct cortico-spinal actions on motoneurones" Electroencephalogr.Clin.Neurophysiol. 97, 1995, 394-401.

Barnes, G.R. et al., "Statistical flattening of MEG beamformer images", Hum.Brain Mapp. 18, 2003, 1-12.

Barros, A.K. et al., "Extraction of event-related signals from multichannel bioelectrical measurements", IEEE Trans. Biomed.Eng 47, 2000, 583-588.

Boakye, M. et al., "Functional magnetic resonance imaging of somatosensory cortex activity produced by electrical stimulation of the median nerve or tactile stimulation of the index finger", J.Neurosurg. 93, 2000, 774-783.

Brookes, M.J. et al., "Measuring functional connectivity using MEG: methodology and comparison with fcMRI", Neuroimage 56, 2011, 1082-1104.

Brookes, M.J. et al., "Investigating the electrophysiological basis of resting state networks using magnetoencephalography", Proc.Natl.Acad.Sci.U.S.A 108, 2011, 16783-16788.

Cohen, D., "Magnetoencephalography: evidence of magnetic fields produced by alpha-rhythm currents", Science 161, 1968, 784-786.

Cohen, D. et al., "Detection of magnetic fields outside the human head produced by alpha rhythm currents", 1970, Electroencephalogr. Clin. Neurophysiol. 28, 102.

Cohen, D. et al., "New Six-Layer Magnetically-Shielded Room for MEG", In: Nowak, H.H.J., Gießler, F. (Eds.), Proceedings of the 13th International Conference on Biomagnetism. VDE Verlag, Jena, Germany, 2002, pp. 919-921.

Davidoff, R.A., "The pyramidal tract", Neurology 40, 1990, 332-339.

Disbrow, E. et al., "Evidence for interhemispheric processing of inputs from the hands in human S2 and PV", J. Neurophysiol. 85, 2001, 2236-2244.

Forss, N. et al., "Activation of the human posterior parietal cortex by median nerve stimulation", Exp.Brain Res. 99, 1994, 309-315.

Forss, N. et al., "Sensorimotor integration in human primary and secondary somatosensory cortices", Brain Res. 781, 1998, 259-267.

Friston, K. et al., "Multiple sparse priors for the M/EEG inverse problem" Neuroimage 39, 2008, 1104-1120.

Fujiwara, N. et al., "Second somatosensory area (SII) plays a significant role in selective somatosensory attention", Brain Res. Cogn Brain Res. 14, 2002, 389-397.

Gaetz, W. et al., "Presurgical localization of primary motor cortex in pediatric patients with brain lesions by the use of spatially filtered magnetoencephalography", Neurosurgery 64, 2009, ons177-ons185.

Gaetz, W. et al., "Localization of human somatosensory cortex using spatially filtered magnetoencephalography", Neurosci.Lett. 340, 2003, 161-164.

Gross, J. et al., "Linear transformations of data space in MEG", Phys.Med.Biol. 44, 1999, 2081-2097.

Gross, J. et al. "Dynamic imaging of coherent sources: Studying neural interactions in the human brain", Proc.Natl.Acad.Sci.U.S.A 98, 694-699.

Hall, E.L. et al., "Using variance information in magnetoencephalography measures of functional connectivity", Neuroimage 67, 2013, 203-212.

Hari, R. et al., "Magnetoencephalography in the study of human somatosensory cortical processing", Philos.Trans.R.Soc.Lond B Biol. Sci. 354, 1999, 1145-1154.

Hari, R. et al., "Functional organization of the human first and second somatosensory cortices: a neuromagnetic study", Eur.J. Neurosci. 5, 1993, 724-734.

Hashimoto, I. et al., "Dynamic activation of distinct cytoarchitectonic areas of the human SI cortex after median nerve stimulation", Neuroreport 12, 2001, 1891-1897.

Hillebrand, A., et al., "The use of anatomical constraints with MEG beamformers", Neuroimage. 20, 2003, 2302-2313.

Hillebrand, A. et al., "Feasibility of clinical magnetoencephalography (MEG) functional mapping in the presence of dental artefacts", Clin.Neurophysiol. 124, 2013, 107-113.

Hipp, J.F. et al., "Large-scale cortical correlation structure of spontaneous oscillatory activity", Nat.Neurosci. 15, 2012, 884-890.

Hirata, M-X. et al., "Frequency-dependent spatial distribution of human somatosensory evoked neuromagnetic fields", Neurosci. Lett. 318, 2002, 73-76.

Huang, M-X. et al., "Multi-start downhill simplex method for spatio-temporal source localization in magnetoencephalography", Electroencephalogr. Clin. Neurophysiol. 108, 1998, 32-44.

Huang, M-X. et al., "MEG response to median nerve stimulation correlates with recovery of sensory and motor function after stroke", Clin.Neurophysiol. 115, 2004, 820-833.

Huang, M-X. et al., "Sources on the anterior and posterior banks of the central sulcus identified from magnetic somatosensory evoked responses using multistart spatio-temporal localization", Hum.Brain Mapp. 11, 2000, 59-76.

Huang, M-X. et al., "Vector-based spatial-temporal minimum L1-norm solution for MEG", Neuroimage 31, 2006, 1025-1037.

Huang, M-X. et al., "Somatosensory system deficits in schizophrenia revealed by MEG during a median-nerve oddball task", Brain Topogr. 23, 2010, 82-104.

Huang, M-X. et al., "A parietal-frontal network studied by somatosensory oddball MEG responses, and its cross-modal consistency", Neuroimage. 28, 2005, 99-114.

Huang, M-X. et al., "An automatic MEG low-frequency source imaging approach for detecting injuries in mild and moderate TBI patients with blast and non-blast causes", Neuroimage 61, 2012, 1067-1082.

Huang, M-X. et al. "A novel integrated MEG and EEG analysis method for dipolar sources", Neuroimage 37, 2007, 731-748.

Huang, M-X. et al., "Integrated imaging approach with MEG and DTI to detect mild traumatic brain injury in military and civilian patients", J.Neurotrauma 26, 2009, 1213-1226.

Hymers, M. et al. "Source stability index: a novel beamforming based localisation metric", Neuroimage 49, 2010, 1385-1397.

(56) References Cited

OTHER PUBLICATIONS

Ioannides, A.A. et al., "Comparison of single current dipole and magnetic field tomography analyses of the cortical response to auditory stimuli", Brain Topogr. 6, 1993, 27-34.
Jones, E.G. et al., "Intracortical connectivity of architectonic fields in the somatic sensory, motor and parietal cortex of monkeys", J.Comp Neurol. 181, 1978, 291-347.
Jones, E.G. et al., "Differential thalamic relationships of sensory-motor and parietal cortical fields in monkeys", J. Comp Neurol. 183, 1979, 833-881.
Jousmaki, V. et al., "Effects of stimulus intensity on signals from human somatosensory cortices", Neuroreport 9, 1998, 3427-3431.
Jung, T-P. et al., "Analysis and visualization of single-trial event-related potentials", Hum.Brain Mapp. 14, 2001, 166-185.
Kawamura, T. et al., "Neuromagnetic evidence of pre- and post-central cortical sources of somatosensory evoked responses", Electroencephalogr. Clin. Neurophysiol. 100, 1996, 44-50.
Lemon, R.N., "Short-latency peripheral inputs to the motor cortex in conscious monkeys", Brain Res. 161, 1979, 150-155.
Lemon, R.N., "Functional properties of monkey motor cortex neurones receiving afferent input from the hand and fingers", J.Physiol 311, 1981, 497-519.
Lemon, R.N., "Afferent input to movement-related precentral neurones in conscious monkeys", Proc.R.Soc.Lond B Biol.Sci. 194, 1976, 313-339.
Makeig, S. et al., "Blind separation of auditory event-related brain responses into independent components", Proc.Natl.Acad.Sci.U.S.A 94, 1997, 10979-10984.
Manshanden, I. et al., "Source localization of MEG sleep spindles and the relation to sources of alpha band rhythms", Clin. Neurophysiol. 113, 2002, 1937-1947.
Matsuura, K. et al., "A robust reconstruction of sparse biomagnetic sources", IEEE Transactions on Biomedical Engineering 44, 1997, 720-726.
Mauguiere, F. et al., "Activation of a distributed somatosensory cortical network in the human brain. A dipole modelling study of magnetic fields evoked by median nerve stimulation. Part I: Location and activation timing of SEF sources", Electroencephalogr. Clin.Neurophysiol. 104, 1997, 281-289.
Mauguiere, F. et al., "Activation of a distributed somatosensory cortical network in the human brain: a dipole modelling study of magnetic fields evoked by median nerve stimulation. Part II: Effects of stimulus rate, attention and stimulus detection", Electroencephalogr. Clin.Neurophysiol. 104, 1997, 290-295.
McCubbin, J. et al., "Advanced electronics for the CTF MEG system" Neurol.Clin.Neurophysiol. 2004, 69.
McGlone, F. et al., "Functional neuroimaging studies of human somatosensory cortex", Behav.Brain Res. 135, 2002, 147-158.
Mizuki, Y. et al., "Differential responses to mental stress in high and low anxious normal humans assessed by frontal midline theta activity", Int.J Psychophysiol. 12, 1992, 169-178.
Mizuki, Y. et al., "Appearance of frontal midline theta rhythm and personality traits", Folia Psychiatr.Neurol.Jpn. 38, 1984, 451-458.
Mizuki, Y. et al., "Periodic appearance of theta rhythm in the frontal midline area during performance of a mental task", Electroencephalogr. Clin. Neurophysiol. 49, 1980, 345-351.
Mosher, J.C. et al., "Recursive MUSIC: a framework for EEG and MEG source localization", IEEE Trans.Biomed. Eng 45, 1998, 1342-1354.
Mosher, J.C. et al., "EEG and MEG: forward solutions for inverse methods", IEEE Trans.Biomed.Eng 46, 1999, 245-259.
Mosher, J.C. et al., "Multiple dipole modeling and localization from spatio-temporal MEG data", IEEE Trans.Biomed.Eng 39, 1992, 541-557.
Rosen, I. et al., "Peripheral afferent inputs to the forelimb area of the monkey motor cortex: input-output relations", Exp.Brain Res. 14, 1972, 257-273.
Sekihara, K. et al., "Performance of prewhitening beamforming in MEG dual experimental conditions", IEEE Trans.Biomed.Eng 55, 2008, 1112-1121.
Sekihara, K. et al. "Reconstructing spatio-temporal activities of neural sources using an MEG vector beamformer technique", IEEE Trans.Biomed.Eng 48, 2001, 760-771.
Sekihara, K. et al., "Noise covariance incorporated MEG-MUSIC algorithm: a method for multiple-dipole estimation tolerant of the influence of background brain activity", IEEE Trans.Biomed.Eng 44, 1997, 839-847.
Sekihara, K. et al., "MEG spatio-temporal analysis using a covariance matrix calculated from nonaveraged multiple-epoch data", IEEE Trans.Biomed.Eng 46, 1999, 515-521.
Simoes, C. et al., "Phase locking between human primary and secondary somatosensory cortices", Proc.Natl.Acad.Sci.U.S.A 100, 2003, 2691-2694.
Song, T. et al., "Evaluation of signal space separation via simulation", Med.Biol.Eng Comput. 46, 2008, 923-932.
Soto, J. et al., "Investigation of cross-frequency phase-amplitude coupling in visuomotor networks using magnetoencephalography", Conf.Proc.IEEE Eng Med.Biol.Soc. 2012, 1550-1553.
Spiegel, J. et al., "Functional MRI of human primary somatosensory and motor cortex during median nerve stimulation", Clin. Neurophysiol. 110, 1999, 47-52.
Takahashi, N. et al., "Frontal midline theta rhythm in young healthy adults", Clin.Electroencephalogr. 28, 1997, 49-54.
Taulu, S. et al., "Suppression of interference and artifacts by the Signal Space Separation Method", Brain Topogr. 16, 2004 269-275.
Taulu, S. et al., "MEG recordings of DC fields using the signal space separation method (SSS)", Neurol.Clin. Neurophysiol. 2004, 35.
Van Veen, B.D. et al., "Localization of brain electrical activity via linearly constrained minimum variance spatial filtering", IEEE Trans.Biomed.Eng 44, 1997, 867-880.
Vigario, R. et al., "Independence: a new criterion for the analysis of the electromagnetic fields in the global brain?", Neural Netw. 13, 2000, 891-907.
Vigario, R. et al., "Independent component approach to the analysis of EEG and MEG recordings", IEEE Trans.Biomed.Eng 47, 2000, 589-593.
Waberski, T.D. et al., "Spatiotemporal imaging of electrical activity related to attention to somatosensory stimulation", Neuroimage. 17, 2002, 1347-1357.
Wong, Y.C. et al., "Spatial organization of precentral cortex in awake primates. I. Somatosensory inputs", J. Neurophysiol. 41, 1978, 1107-1119.
Wood, C.C. et al., "Electrical sources in human somatosensory cortex: identification by combined magnetic and potential recordings", Science 1985, 227, 1051-1053.
International Search Report and Written Opinion of International Application No. PCT/US2014/049824; dated Dec. 11, 2014.
Brang, D. et al., "Magnetoencephalography reveals early activation of V4 in grapheme-color synesthesia", Neuroimage 53, 2010, 268-274.
Berger, H., "Uber das Elektrenkephalogramm des Menschen", Arch.Psychiatr.Nervenkr.Z.Gesamte Neurol. Psychiatr. 87, 1929, 527-570.

* cited by examiner

MAGNETOENCEPHALOGRAPHY SOURCE IMAGING FOR NEUROLOGICAL FUNCTIONALITY CHARACTERIZATIONS

PRIORITY CLAIM

This patent document claims the priority of U.S. provisional application No. 61/862,511 entitled "MAGNETOENCEPHALOGRAPHY SOURCE IMAGING FOR NEUROLOGICAL FUNCTIONALITY CHARACTERIZATIONS" filed on Aug. 5, 2013, which is incorporated by reference as part of this document.

STATEMENT REGARDING FEDERALLY SPONSORED RESEARCH OR DEVELOPMENT

This invention was made with government support under MH068004 awarded by National Institutes of Health. The government has certain rights in the invention.

TECHNICAL FIELD

This patent document relates to medical imaging technologies.

BACKGROUND

Axonal injury is a leading factor in neuronal injuries such as mild traumatic brain injury (TBI), multiple sclerosis (MS), Alzheimer's Disease/dementia (AD), among other disorders. In addition, abnormal functional connectivity exists in these neuronal disorders as well as others, such as post-traumatic stress disorder (PTSD). Neuroimaging tools have been used for diagnosing neurological and psychiatric disorders, e.g., including TBI, PTSD, AD, autism, MS, and schizophrenia. For example, neuroimaging techniques such as X-radiation (X-ray), X-ray computed tomography (CT), magnetic resonance imaging (MRI), and diffusion tensor imaging (DTI) have been employed.

Many of these neuroimaging techniques mainly focus on detecting blood products, calcification, and edema, but are less sensitive to axonal injuries and abnormal functional connectivity in the brain. For example, X-ray, CT, and MRI can have relatively low diagnostic rates to these neurological and psychiatric disorders. For example, less than 10% of mild TBI patients have shown positive findings in X-ray, CT, and MRI. Some techniques such as diffusion tensor imaging (DTI) have shown to produce a positive finding rate ~20-30% for mild TBI.

SUMMARY

Disclosed are diagnostic systems, devices and techniques using magnetoencephalography (MEG) to detect loci of neuronal injury and abnormal neuronal networks, which are not visible with conventional neuroimaging techniques (e.g., X-ray, CT and MRI).

In one aspect, a method includes determining a covariance matrix based on sensor signal data in the time or frequency domain, the sensor signal data representing magnetic-field signals emitted by a brain of a subject and detected by a plurality of MEG sensors in a sensor array surrounding the brain, defining a source grid containing source locations within the brain that generate magnetic signals, the source locations having a particular resolution, in which a number of source locations is greater than a number of sensors in the sensor array, and generating a source value of signal power for each location in the source grid by fitting the selected sensor covariance matrix, in which the covariance matrix is time-independent based on time or frequency information of the sensor signal data.

Implementations of the described method can optionally include one or more of the following features. The number of source locations can be at least 30 times greater than the number of sensors in the sensor array. Also, the number of source locations can include at least 10,000 voxels. In addition, the number of sensors in the sensor array can include at least 250 sensors. An image including image features representing the source values at locations mapped to corresponding voxels in a magnetic resonance imaging (MRI) image of the brain can be produced.

In another aspect, a magnetoencephalography (MEG) source imaging system includes a MEG machine including MEG sensors to acquire magnetic field signal data including MEG sensor waveform signals from a brain of a subject. The MEG sensor signal data can represent magnetic-field signals emitted by the brain of the subject. The MEG source imaging system can include a processing unit including a processor configured to perform the following including determine time-independent signal-related spatial modes from the detected MEG sensor waveform signals, obtain spatial source images of the brain based on the determined time-independent signal-related spatial modes, and determine source time-courses of the obtained spatial source images.

Implementations of the described system can optionally include one or more of the following features. The processing unit can objectively remove correlated noise from the detected MEG sensor waveform signals. The processing unit can obtain the spatial source images of the brain based on the determined time-independent signal-related spatial modes based at least on a source imaging map associated with each time-independent signal-related spatial mode. The processing unit can remove bias toward grid nodes. The processing unit can remove bias towards coordinate axes. The processing unit can determine the source time-courses of the obtained spatial source images based at least on the following including an inverse operator matrix constructed based on the obtained spatial source images; and application of the constructed inverse operator matrix to the detected MEG sensor waveform signal.

Implementations of the described system can optionally include one or more of the following features. The processing unit can determine a goodness-of-fit to the detected MEG sensor waveform signal. The processing unit can determine the goodness-of-fit without calculating a predicted MEG sensor waveform signal. The processing unit can determine the goodness-of-fit based at least on measured and predicted sensor spatial-profile matrix. The processing unit can objectively remove the correlated noise from the detected MEG sensor waveform signals based at least on the following including a mother brain noise covariance matrix estimated based on incomplete information; a pre-whitening operator constructed based on the estimated mother brain noise covariance matrix; a daughter pre-whitened brain noise covariance matrix formed based on application of the pre-whitening operator to daughter brain noise data; a plot of square root of eigenvalues of the daughter pre-whitened brain noise covariance matrix; a plot of 2nd order derivatives of the square root of the eigenvalues in the daughter pre-whitened brain noise covariance matrix; a noise-subspace identified from the plot of 2nd order derivatives; and associated threshold values from the plot of square root of the eigenvalues of the daughter pre-whitened brain noise covariance matrix. The MEG source imaging system can include a magnetic resonance imaging (MRI) machine configured to acquire MRI images to obtain a source grid of the brain.

In yet another aspect, a tangible non-transitory storage medium embodying a computer program product can include instructions for performing magnetoencephalography (MEG) source imaging when executed by a processing unit. The instructions of the computer program product can include determining by the processing unit a covariance matrix based on sensor signal data in the time domain, the sensor signal data representing magnetic-field signals emitted by a brain of a subject and detected by a plurality of MEG sensors in a sensor array surrounding the brain; defining by the processing unit a source grid containing source locations within the brain that generate magnetic signals, the source locations having a particular resolution, wherein a number of source locations is greater than a number of sensors in the sensor array; and generating by the processing unit a source value of signal power for each location in the source grid by fitting the selected sensor covariance matrix. The covariance matrix is time-independent based on time information of the sensor signal data.

Implementations of the described tangible non-transitory storage medium embodying a computer program product that includes instructions for performing magnetoencephalography (MEG) source imaging can optionally include one or more of the following features. The number of source locations can be at least 30 times greater than the number of sensors in the sensor array. The number of source locations can include at least 10,000 voxels. The number of sensors in the sensor array can include at least 250 sensors. The instructions can include producing by the processor an image including image features representing the source values at locations mapped to corresponding voxels in a magnetic resonance imaging (MRI) image of the brain.

The subject matter described in this patent document can be implemented in specific ways that can potentially provide one or more of the following features. For example, the disclosed technology that includes a fast MEG source imaging technique is based on an L1-minimum-norm solution referred to as Fast-Vector-based Spatial-Temporal Analysis, which can be applied to obtain the source amplitude images of resting-state MEG signals for different frequency bands. In some aspects, an exemplary Fast-VESTAL technique can include a process to obtain L1-minimum-norm MEG source images for the dominant spatial modes of sensor-waveform covariance matrix, and a process to obtain accurate source time-courses with millisecond temporal resolution, using an inverse operator constructed from the spatial source images obtained in the previous process. In some aspects, the disclosed Fast-VESTAL techniques can be implemented in conjunction with a disclosed objective pre-whitening method (OPWM) to remove correlated noises.

Implementations of the disclosed Fast-VESTAL technique can potentially improve sensitivity of detecting injuries and abnormalities in mild traumatic brain injury (TBI) and post-traumatic stress disorder (PTSD). Additionally, for example, the disclosed Fast-VESTAL technology can be implemented using low computational costs of the computer or computer systems that implement the Fast-VESTAL techniques. The disclosed Fast-VESTAL technology includes the capability to (1) localize and resolve a large number (e.g., up the limit determined by the number of MEG sensors) of focal and distributed neuronal sources with any degrees of correlations, (2) obtain accurate source time-courses, and hence the accurate source-based functional connectivity at poor signal-to-noise (SNR) conditions, e.g., even at SNRs in the negative dB ranges, (3) operate with substantially low signal leakage of the Fast-VESTAL solution to other areas where no sources exist, and (4) facilitate imaging registration and group analysis by providing voxel-based whole brain imaging of MEG signal, among other potential features and advantages.

BRIEF DESCRIPTION OF THE DRAWINGS

FIG. 12A shows, in the bottom row, F-value maps of the beamformer solution.

DETAILED DESCRIPTION

Systems, devices, and techniques are disclosed for using MEG to detect loci of neuronal injury and abnormal neuronal networks to characterize neurological functionality.

MEG is a technique for mapping brain activity by recording magnetic fields produced by intracellular electrical currents in the brain. MEG source modeling for analyzing MEG data (e.g., MEG slow-wave) uses equivalent current dipole models to fit operator-specified time-window of activities. MEG source imaging can be used to detect neuronal injuries and abnormalities in patients with neurological and/or psychiatric disorders with high resolution and great sensitivity. In this document, an exemplary MEG-based system that can be used to perform VESTAL and Fast-VESTAL solutions is described. The description of the exemplary MEG-based system is followed by a summary of VESTAL techniques and detailed description of Fast-VESTAL techniques that provide various improvements to VESTAL.

Exemplary MEG-Based System

Figure 1:
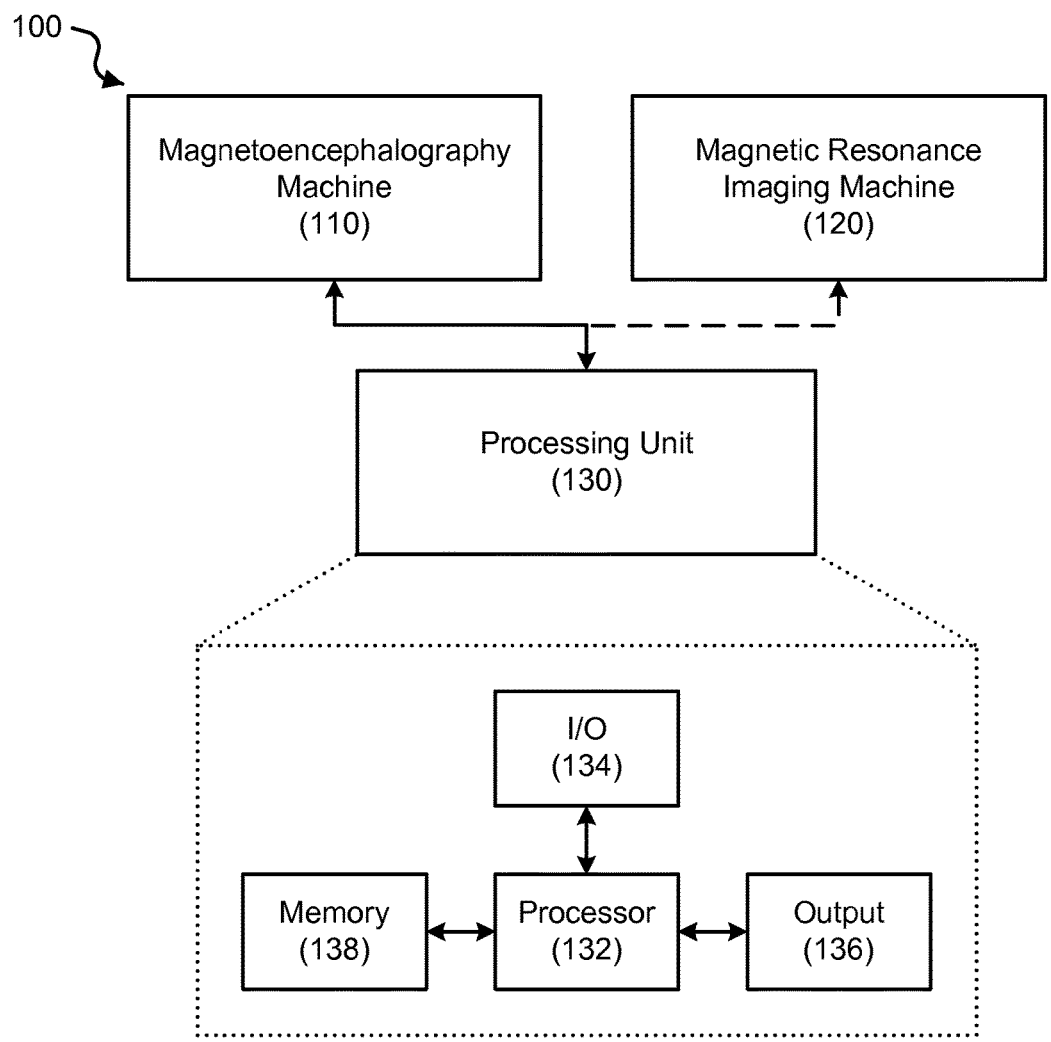
FIG. 1A shows an exemplary MEG-based system for implementing the disclosed Fast-VESTAL techniques.

FIG. 1 shows an exemplary MEG-based system 100 for implementing VESTAL and Fast-VESTAL techniques. The MEG-based system 100 can be used to obtain non-invasive, in vivo biomarker data from healthy and diseased tissues using the high resolution MEG source imaging technique in time and frequency domains to detect loci of neuronal injury and abnormal neuronal networks. The exemplary system 100 can include a magnetoencephalography (MEG) machine 110 and magnetic resonance imaging (MRI) machine 120, which can be controlled by a processing unit 130. For example, processing unit 130 can control operations of MEG machine 110 and MRI machine 120 to implement various processes and applications of the disclosed Fast-VESTAL technology.

MEG machine 110 can be used in the system 100 to implement magnetic field signal data acquisition. For example, MEG machine 110 can include an array of magnetometer sensors that can detect magnetic signals emitted by the brain. Examples of the array of magnetometer sensors include a superconducting quantum interference device (SQUID). In some implementations, the SQUID sensors can be contained in an enclosed casing or housing that can maintain cryogenic temperatures for operation. Examples of the enclosed casing or housing include a helmet-shaped liquid helium containing vessel or dewar. However, other functionally similar enclosed casing or housing that can maintain the cryogenic temperatures for operation can also be used.

The MEG machine 110 can include an array of hundreds or thousands of SQUIDS that can record simultaneous measurements over a subject's head at several regions on a micrometer or millimeter scale. A large number of sensors can be used at different spatial locations around the subject's brain to collect magnetic signals emitted by the brain to gain the spatial diversity of the brain's emission of magnetic signals. Increasing the number of the sensors in the MEG machine 110 can likewise increase or enhance the spatial resolution of the source imaging information. However, the techniques described in this document can allow the system 100 to utilize a total number of sensors that is much smaller than the number of source locations to be imaged. In other words, the techniques described in this document can allow the system 100 to use a limited number of sensors to provide MEG imaging at a much greater number of source locations in the brain.

The system 100 can include a magnetically shielded room to contain the exemplary MEG machine 110 to minimize interference from external magnetic noise sources, e.g., including the Earth's magnetic field, electrical equipment, radio frequency (RF) signaling, and other low frequency magnetic field noise sources. The exemplary magnetically shielded room can be configured to include a plurality of nested magnetically shielding layers, e.g., including pure aluminum layer and a high permeability ferromagnetic layer (e.g., such as molybdenum permalloy).

The MRI machine 120 can be used in the system 100 to implement MRI imaging in support of the exemplary Fast-VESTAL characterization process described below under the control of the processing unit 130. The MRI machine 120 can include various types of MRI systems, which can perform at least one of a multitude of MRI scans that can include, but are not limited to, T1-weighted MRI scans, T2-weighted MRI scans, T2*-weighted MRI scans, spin (proton ($^1$H)) density weighted MRI scans, diffusion tensor imaging (DTI) and diffusion weighted imaging (DWI) MRI scans, diffusion spectrum imaging (DSI) MRI scans, T1ρ MRI scans, magnetization transfer (MT) MRI scans, real-time MRI, functional MRI (fMRI) and related techniques such as arterial spin labeling (ASL), among other MRI techniques.

The processing unit 130 can include a processor 132 that can be in communication with an input/output (I/O) unit 134, an output unit 136, and a memory unit 138. For example, the processing unit 130 can be implemented as one of various data processing systems, such as a personal computer (PC), laptop, tablet, and mobile communication device. To support various functions of the processing unit 130, the processor 132 can be implemented to interface with and control operations of other components of the processing unit 130, such as the I/O unit 134, the output unit 136, and the exemplary memory unit 138.

To support various functions of the processing unit 130, the memory unit 138 can store other information and data, such as instructions, software, values, images, and other data processed or referenced by the processor 132. For example, various types of Random Access Memory (RAM) devices, Read Only Memory (ROM) devices, Flash Memory devices, and other suitable storage media can be used to implement storage functions of the memory unit 138. The exemplary memory unit 138 can store MEG and MRI data and information, which can include subject MEG and MRI data including temporal, spatial and spectral data, MEG system and MRI machine system parameters, data processing parameters, and processed parameters and data that can be used in the implementation of a Fast-VESTAL characterization. The memory unit 138 can store data and information that can be used to implement an MEG-based Fast-VESTAL process and that can be generated from an MEG-based Fast-VESTAL characterization algorithm and model.

To support various functions of the processing unit 130, the I/O unit 134 can be connected to an external interface, source of data storage, or display device. For example, various types of wired or wireless interfaces compatible with typical data communication standards, such as Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement the I/O unit 134. The I/O unit 134 can interface with an external interface, source of data storage, or display device to retrieve and transfer data and information that can be processed by the processor 132, stored in the memory unit 138, or exhibited on the output unit 136.

To support various functions of the processing unit 130, the output unit 136 can be used to exhibit data implemented by the processing unit 130. The output unit 136 can include various types of display, speaker, or printing interfaces to implement the exemplary output unit 136. For example, the output unit 136 can include cathode ray tube (CRT), light emitting diode (LED), or liquid crystal display (LCD) monitor or screen as a visual display to implement the output unit 136. In other examples, the output unit 136 can include toner, liquid inkjet, solid ink, dye sublimation, inkless (such as thermal or UV) printing apparatuses to implement the output unit 136; the output unit 136 can include various types of audio signal transducer apparatuses to implement the output unit 136. The output unit 136 can exhibit data and information, such as patient diagnostic data, MEG machine system information, MRI machine system information, partially processed MEG-based Fast-VESTAL processing information, and completely processed MEG-based Fast-VESTAL processing information. The output unit 136 can store data and information used to implement an exemplary MEG-based Fast-VESTAL characterization process and from an implemented MEG-based Fast-VESTAL characterization process.

Exemplary implementations were performed using the disclosed Fast-VESTAL techniques. In one example, a computer-implemented Fast-VESTAL method was implemented to localize correlated sources and accurately reconstructs their source time-courses, e.g., even at poor signal-SNR conditions. For example, application of the disclosed Fast-VESTAL techniques to human MEG median-nerve responses further demonstrated its power in reconstructing source time-courses that were highly consistent with known electrophysiology of the human somatosensory system. For example, implementation of an exemplary Fast-VESTAL technique provided a set of comprehensive MEG source-amplitude images that covered the entire brain in standard atlas coordinates for different frequency bands of resting-state signals, which also showed that the Fast-VESTAL technology involves low computational costs.

Exemplary Source Models for MEG

In one aspect, described is a MEG source imaging technique based on Fast Vector-based Spatio-Temporal Analysis using L1-minimum-norm (Fast-VESTAL), which can be implemented to obtain the source amplitude images of resting-state MEG signals for different frequency bands. In one exemplary implementation, a Fast-VESTAL technique includes a first process to obtain L1-minimum-norm MEG source images for the dominant spatial modes of sensor-waveform covariance matrix, and a second process to obtain accurate source time-courses with millisecond temporal resolution, e.g., using an inverse operator constructed from the spatial source images of first process. Also disclosed is an objective pre-whitening method that can be implemented with the Fast-VESTAL techniques to objectively remove correlated brain noise.

MEG is a functional imaging technique that directly measures neuronal activity with millisecond temporal resolution. MEG source imaging is used to determine the source locations and the source time-courses of neuronal activities responsible for the observed MEG field distribution. Because many sets of source configurations can generate essentially the same MEG field distribution, constraints can be imposed on sources by stipulating a "source model".

A source model for MEG based on a set of equivalent current dipoles (ECDs) assumes focal neuronal currents can be modeled by one or more point-like dipoles. Automated multiple-dipole model algorithms such as multiple signal classification (MUSIC) and multi-start spatio-temporal (MSST) multiple-dipole modeling can be applied to the analysis of human MEG data. Adequately characterizing neuronal responses using dipole models can be affected by the ability of the dipole models to accurately model extended sources with ECDs and accurately estimate the number of dipoles in advance.

Minimum L2-norm solutions (e.g., dSPM, MNE, sLORETA)-based modeling is another type of a source model for MEG. Source space, such as brain volume or cortex, is divided into a grid containing a large number of dipoles, which can typically be several thousands. An inverse procedure is used to obtain the dipole moment distribution across different grid nodes by minimizing the total power, L2 norm. The minimum L2-norm solution is obtained using a direct linear inverse operator, such as pseudo-inverse with regularization, of the lead-fields. However, the spatial resolution of the minimum L2-norm solution is low and can often provide distributed reconstructions even if true generators are focal. Cross-talk between source time-courses of nearby grid points can also be high.

Spatial filtering is yet another type of source modeling for MEG that makes assumptions about the temporal property of source time-courses. For example, single-core beamformer approaches fall into the spatial filtering framework, and assume that different source time-courses are uncorrelated. The application of the single-core beamformer can be affected by the assumption of different source time-courses being uncorrelated because of the signal leaking and distortion associated with reconstructed source time-courses when neuronal sources are correlated. In evoked responses, electro-neurophysiology studies show that brain sources can be highly correlated because they work together to achieve a task goal.

For highly-correlated sources, dual-core beamformer techniques can be used. In one example, a source reconstruction algorithm Champgne uses an iterative approach to optimize a cost function related to the logarithm of the trace in data model covariance. In another example, a high-resolution MEG time-domain inverse imaging method known as Vector-based Spatial-Temporal Analysis uses a L1-minimum-norm solution (VESTAL), in which temporal information in the data is used to enhance the stability of the reconstructed vector-based L1-minimum norm solution. Potential advantages of VESTAL include (1) the ability to model many dipolar and non-dipolar sources, (2) no requirement of pre-determination of the number of sources (model order), (3) the ability to resolve 100% temporally correlated sources, and (4) substantially higher spatial resolution than many lead-field-based MEG source modeling techniques. VESTAL can be expanded from the time-domain to the frequency-domain to effectively image oscillatory MEG signals including complicated MEG slow-waves in patients with traumatic brain injury. While the computational costs of VESTAL in the time- and frequency-domains are manageable, they increase linearly with the number of time samples or frequency bins. Basic description of VESTAL technology is provided below.

Exemplary VESTAL Techniques

In VESTAL, an imaging (lead-field) data set can be taken, in which the source space (e.g., gray-matter brain volume) is divided into a grid of source locations. Exemplary MEG time-domain signals can then be expressed in a data matrix, e.g., such as $B(t)=[b(t_1), b(t_2), \ldots, b(t_N)]$, where N is the number of time samples and $b(t_i)$ is a M×1 vector containing the magnetic fields at M sensor sites at time point $t_i$. The data matrix can be expressed as:

$$B(t)=GQ(t)+\text{Noise}(t) \qquad \text{(Eq. 1)}$$

where G can represent an M×2P gain (lead-field) matrix calculated from MEG forward modeling for the pre-defined source grid with P dipole locations, e.g., with each dipole location having two orthogonal orientations (e.g., θ and φ), and Q(t) can represent a 2P×N source time-course matrix. In the exemplary spherical MEG forward head model, θ and φ can represent the two tangential orientations for each dipole location; whereas in a realistic MEG forward model using the boundary element method (BEM), the θ and φ orientations can be obtained as the two dominant orientations from the singular value decomposition (SVD) of the M×3 lead-field matrix for each dipole. An exemplary inverse solution in Eq. 1 can be to obtain the source time-courses Q(t) for given MEG sensor wave-forms B(t). For example, for each time-sample, since the number of unknown parameters can be far greater than the number of sensor measurements (e.g., 2P>>M), MEG source imaging deals with a highly under-determined problem, e.g., in which there can be a large number of solutions that will fit the data. To reduce the ambiguity, additional constraints (e.g., source models) can be applied, as described herein.

The disclosed vector-based spatio-temporal analysis using L1-minimum norm (VESTAL) techniques can be implemented as a high-resolution time-domain and frequency-domain MEG source imaging solution for Eq. 1 that includes the following exemplary properties. For example, exemplary VESTAL techniques can be used to model many dipolar and non-dipolar sources; the disclosed VESTAL techniques can be implemented with no pre-determination of the number of sources (e.g., model order); and exemplary VESTAL techniques can resolve 100% temporally correlated sources. For example, to more effectively image oscillatory MEG signals, such as complicated MEG slow-waves, the described VESTAL techniques can be utilized in the frequency-domain. For example, the MEG signal for a few frequency bins can be analyzed, instead of thousands of time samples in a given time window (e.g., an epoch).

For example, to image resting-state MEG signal, the spontaneous time-domain data (e.g., MEG signal data) can be divided into epochs. For example, by performing Fast Fourier Transform (FFT) techniques to transfer each epoch into F frequency bins, Eq. 1 can be expressed as:

$$[K_{real}(f) K_{imag}(f)] = G[\Omega_{real}(G(f)\Omega_{imag}(f)] \qquad \text{(Eq. 2)}$$

where the M×F matrices $K_{eal}$ and $K_{imag}$ are the real and imaginary parts of the FFT of the sensor waveform B(t) for given frequency f, and the 2P×F matrices $\Omega_{real}$ and $\Omega_{imag}$ contain the Fourier Transformation coefficients of source time-course Q(t). For example, the inverse solution to the frequency-domain Eq. 2 can include determining $\Omega_{real}$ and $\Omega_{imag}$, which are the source amplitudes at different frequency bins for given sensor-space frequency-domain signal $K_{real}$ and $K_{imag}$. As in the time-domain, the exemplary inverse problem can be under-determined.

For example, letting ω be the 2P×1 source-spaced Fourier coefficient vector from a column in either $\Omega_{real}$ or $\Omega_{imag}$ for a given frequency bin (e.g., no longer represented with the "real" and "imag" subscripts for now), and letting $G=USV^T$ be the truncated singular value decomposition of the gain matrix, the L1-minimum norm solution to Eq. 2 can be represented as:

$$\min(w^T|\omega|) \text{ subject to constraints } SV^T\omega \approx U^T\kappa \qquad \text{(Eq. 3)}$$

where κ is the sensor-spaced Fourier coefficient vector from the corresponding column in either $K_{real}$ or $K_{imag}$. For example, on an exemplary Elekta/Neuromag VectorView system, the top 40 singular values can be kept during the singular value decomposition (SVD) truncation of the gain matrix G. In Eq. (3), w is a 2P×1 weighting vector chosen to remove potential bias towards grid nodes at the superficial layer, and it can be taken to be the column norm of the G matrix or a Gaussian function. The solution to Eq. (2) can be a non-linear minimization procedure since the source-space Fourier coefficient ω can be either positive or negative. However, in practice, one can replace the absolute values in |ω| with the following two sets of non-negative values related to ω, and solve the set of equations through linear programming (LP). For example, with the introduction of two new non-negative variables $\omega^a$ and $\omega^b$, Eq. (3) can be represented as:

$$\min(w^T(\omega^a+\omega^b)) \text{ subject to } SV^T\omega \cong U^T\kappa, \omega=\omega^a-\omega^b,$$

$$\{\omega_j^a\},\{\omega_j^b\}\geq 0,\{\omega_j\},j=1,2,\ldots,2P \quad \text{(Eq. 4)}$$

Eq. (4) can be solved (e.g., by using LP techniques, including SeDuMi to solve the above equation-set to get source imaging ω for a given frequency bin). This exemplary step can be repeated for each frequency bin to obtain the whole frequency-domain source images for both the real and imaginary parts of the signal, e.g., $\Omega_{real}$ or $\Omega_{imag}$.

The L1-minimum norm approach can be used to address a problem in which the solution can have a small tendency (bias) towards the coordinate axes. For example, in a spherical MEG head model, for a dipole at the $i^{th}$ node of the grid, the vector-based L1-minimum norm solution can also be expressed as minimizing $$\sum_{i=1}^{P} w_i \omega_i (|\cos(\psi_i)| + |\sin(\psi_i)|),$$

where $\psi_i$ is the angle between total dipole moment and the orientation of the elevation in a tangential plane containing the dipole node, and $\omega_i = \sqrt{(\omega_i^\theta)^2+(\omega_i^\phi)^2}$ is the non-negative dipole strength. This can introduce a bias towards the coordinate axes. In order to handle this small bias, an additional correction factor $(|\cos(\psi_i^e)|+|\sin(\psi_i^e)|)^{-1}$ can be included in the weighting vector w in Eq. (4) for one more iteration, where $\psi_i^e$ to is the angle associated with the estimated orientation based on L1-minimum norm solution without the correction factor.

In a time-domain L1-norm approach, problems can exist that include instability in spatial construction and discontinuity in reconstructed source time-courses. For example, this can be seen as "jumps" from one grid point to (usually) the neighboring grid points. Equivalently, the time-course of one specific grid point can show substantial "spiky-looking" discontinuity. Direct frequency-domain L1-norm solution (e.g., $\Omega_{real}$ or $\Omega_{imag}$) operating on individual frequency bins can also suffer from the same instability as in the time domain.

For example, according to MEG physics, magnetic waveforms in the sensor-space are linear functions of the dipole time-courses in the source-space. The exemplary frequency-domain VESTAL can include performing singular value decomposition (SVD) for the M×F frequency domain MEG sensor signal:

$$K=U_B S_B V_B^T \quad \text{(Eq. 5)}$$

(e.g., variables in Eq. 5 are shown without the "real" and "imag" subscripts, as it applies to both).

For example, all frequency-related information in the MEG sensor signal can be represented as a linear combination of the singular vectors in the matrix $V_B$. For example, since MEG sensor-spaced signals can be linear functions of the underlying neuronal source-space signal, the same signal sub-space that expands the frequency dimension of sensor-space Fourier coefficient matrix K can also expand the frequency dimension of the 2P×F source-space Fourier coefficient matrix Ω (e.g., also noted that the "real" and "imag" subscripts are not shown here). For example, by projecting Ω towards $V_B$, it is ensured that the source spectral matrix Ω and sensor spectral matrix K share the same frequency information (e.g., as required by the MEG physics):

$$\Omega_{Freq\_VESTAL}=\Omega P_\| \quad \text{(Eq. 6)}$$

where the projection matrix $P_\|=V_B V_B^T$ is constructed using the dominant (signal-related) temporal singular vectors (subspace) of the sensor waveforms. For example, $\Omega_{Freq\_VESTAL}$ can be called the frequency-domain singular vectors (subspace) of the sensor waveforms. $\Omega_{Freq\_VESTAL}$ can be referred to as the frequency-domain VESTAL solution. For example, the procedure as described in Eqs. (4)-(6) can apply to the real and imaginary parts of the signal separately. The exemplary frequency-domain VESTAL source image can be obtained by combining the real and imaginary parts together.

Figure 2A:
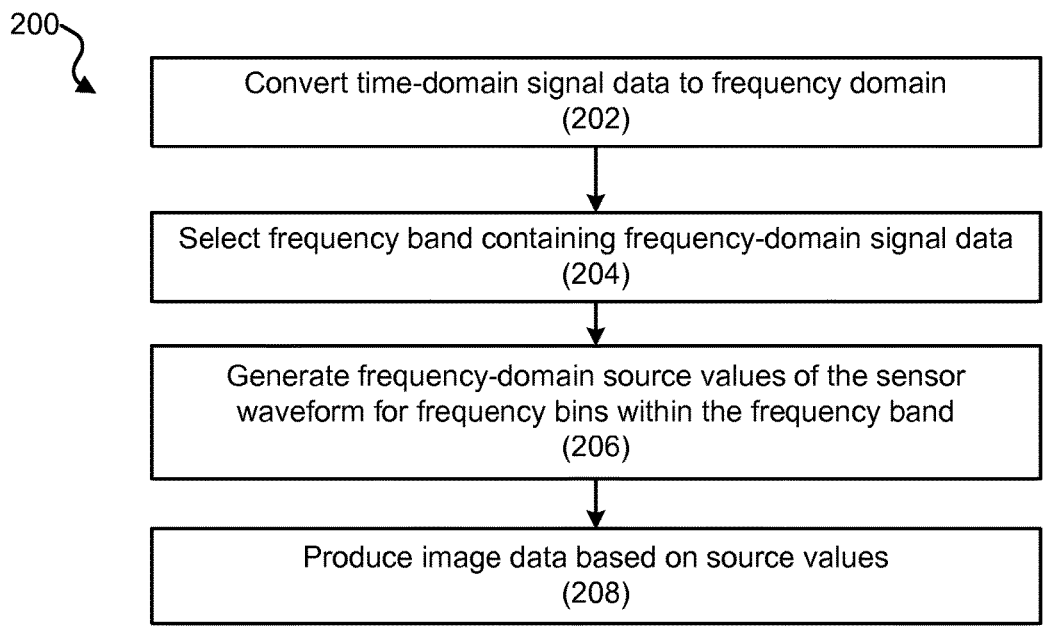
FIGS. 2A and 2B are process flow diagrams showing exemplary MEG-based VESTAL imaging processes.
Figure 2B:
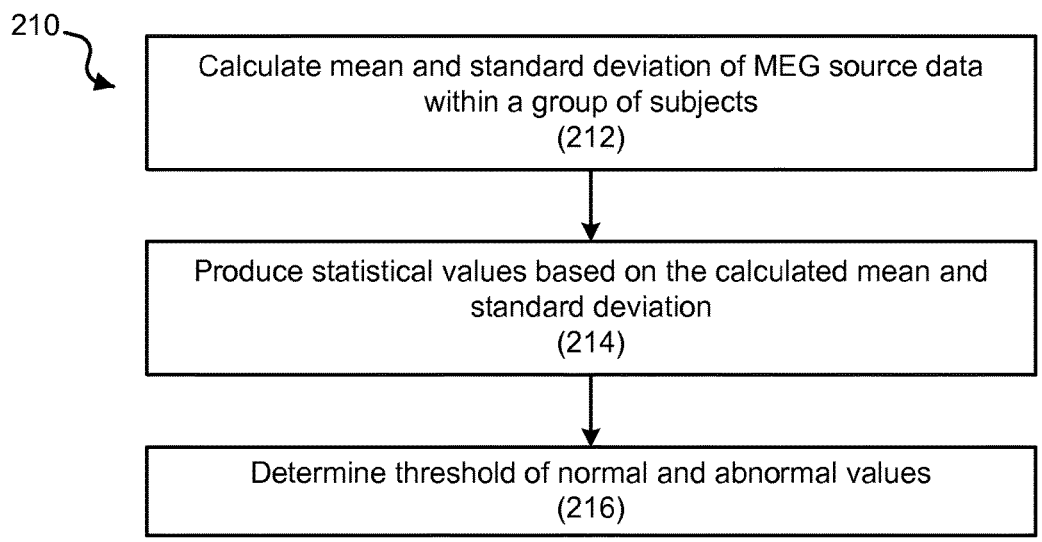

FIGS. 2A and 2B show block diagrams of exemplary frequency-based VESTAL processes. FIG. 2A shows an exemplary process 200 to determine source data with high spatial and temporal resolutions from detected signal data, e.g., in which the source data locations are substantially greater (e.g., at least 10 times greater) than the number of sensors used to detect the signals. For example, the process 200 can be used to implement a frequency-domain VESTAL technique for MEG source imaging that can select signal data (e.g., magnetic field signals obtained by MEG sensors) within one or more frequency bands from a spectrum of the signal data in the frequency domain, define location values (e.g., source grid points that can correspond to voxels) that map to locations within the brain, and generate a source value of signal power based on the selected signal data corresponding to the location values for each frequency bin of the selected frequency band. For example, selecting the signal data within the particular frequency band can include removing other signal data associated with other frequency bands, e.g., optimizing the generation of signal source values.

The exemplary process 200 can include a signal conversion process 202 to convert time-domain signal data to data in the frequency domain. For example, the signal conversion process 202 can include implementing a Fourier Transformation to convert the time-domain MEG sensor waveforms to the frequency domain and obtain the Fourier components (e.g., the exemplary sensor-space frequency-domain signal $K_{real}$ and $K_{imag}$) of the MEG sensor waveforms, as described by Eq. 2.

The exemplary process 200 can include a frequency band selection process 204 to select a specific frequency band or multiple frequency bands. For example, the frequency band selection process 204 can include selecting frequency-domain MEG signal data in the delta band (e.g., 1-4 Hz). For example, the selected frequency band(s) can include any number of discrete frequencies (e.g., which can be referred to as frequency bins), e.g., such as 1.0, 1.1, 1.2, ... 4.0 Hz within the exemplary selected delta band. For example, frequency-domain signal data can be selected by determining the particular frequency bands, e.g., by filtering the signal data through one or more filters (e.g., including low pass, high pass, band pass filters, among other filters).

The exemplary process 200 can include a frequency-domain VESTAL solution generation process 206 to generate frequency-domain singular vectors of the sensor waveform (e.g., the frequency-domain VESTAL solutions), e.g., by applying minimum L1-norm inverse solution. For example, the exemplary singular vectors of the sensor waveform can include the source value of signal power based on the selected MEG signal data corresponding to each source location (e.g., voxels in an image) for each frequency bin within the selected frequency band. For example, the frequency-domain VESTAL solution generation process 206 can include calculating the MEG forward solution using a boundary element method (BEM) to construct the gain matrix G (e.g., also referred to as the lead-field matrix), and applying singular value decomposition (SVD) to the gain matrix $G=USV^T$. The frequency-domain VESTAL solution generation process 206 can include arranging the exemplary SVD matrices of G and the Fourier components of sensor waveforms ($K_{real}$ and $K_{imag}$), as described in Eqs. 3 and 4, for minimum L1-norm solver. For example, the first terms of the L1-minimum norm requirement (e.g., $\min(w^T|\omega|)$ in Eqs. 3 and 4) are the important terms to obtaining high-resolution source imaging, e.g., for MEG source imaging that includes the number of MEG sensors (e.g., ~250) that is far less than the number of source variables (e.g., ~>10, 000) for a typical sources grid with thousands of voxels (e.g., ~10,000 voxels). For example, the remaining terms of Eqs. 3 and 4 are to ensure that the solutions fit the MEG data, e.g., in terms of Fourier components of sensor waveforms. The frequency-domain VESTAL solution generation process 206 can include using linear-programming techniques as the minimum L1-norm solver, e.g., to solve Eq. 4 and obtain the source-space Fourier coefficient $\omega$, e.g., the current flow vectors for each voxel of MEG source current images.

The exemplary process 200 can include an image data producing process 208 to produce image data based on the source values (e.g., the source-space coefficients). For example, the frequency-domain VESTAL solutions can be used to produce source images representing MEG source power (e.g., within each voxel of an image, which can include ~10,000 voxels). The exemplary MEG source imaging diagram can be an MEG spatial map of the source values having a high resolution, e.g., a resolution of at least one source value per one millimeter volume of the brain. In some examples, the resolution of the MEG spatial map can be 2 mm to 3 mm, e.g., which can based on the signal-to-noise ratio. For example, the image data producing process 208 can include removing form systematic bias and constructing the VESTAL source power images for each frequency bins (e.g., in accordance with Eqs. 5 and 6). For example, the image data producing process 208 can include displaying the VESTAL-based MEG source power images on exemplary anatomical MRI images (e.g., of the brain). For example, an exemplary mask (e.g., such as brain cortical region mask) can be applied to group the exemplary MEG source power data from each source location (e.g., the exemplary ~10,000 voxels) into a smaller number of regions (e.g., such as 96 cortical regions) to develop exemplary 2D MEG frequency-power diagrams (e.g., including matrix dimensions: number of brain regions×number of frequency bins)

The disclosed VESTAL technology can be implemented in non-invasive diagnostic applications to detect and characterize loci of neuronal injury and abnormal neuronal networks, e.g., in patients with neurological and/or psychiatric disorders. FIG. 2B shows an exemplary process 210 to create a normative database that can be used to characterize and distinguish healthy and abnormal brains. For example, the exemplary process 210 can be implemented for MEG source imaging in a large number of healthy subjects (e.g., subjects without brain injury, disease, or disorder) to develop a healthy control data base for each cell of the exemplary 2D MEG frequency-power diagrams. As shown in FIG. 2B, the normal database producing process 210 can include a mean and standard deviation calculation process 212 to calculate the mean and standard deviation for each cell of an exemplary 2D MEG frequency-power diagrams across subjects within a group, e.g., such as the healthy control subjects. The normal database producing process 210 can include a statistical core value producing process 214 to produce statistical score values (e.g., referred to as Z-score values) based on the calculated mean and standard deviation values of the exemplary group. For example, the statistical core value producing process 214 can include converting the 2D MEG frequency-power diagram of each healthy control subject into a Z-score 2D diagram based on the group mean and standard deviation for each cell. The normal database producing process 210 can include a threshold determination process 216 to determine a threshold value that can be used to differentiate between normal and abnormal values. For example, the threshold determination process 216 can include selecting the highest Z-value for the entire Z-score diagram of each control, and designating that Z-value to represent that control's maximum Z-score. For example, the highest maximum Z-score of all of the controls can be chosen, e.g., by setting that value as the threshold to differentiate between normal (e.g., less than or equal to that threshold Z-score) vs. abnormally-high delta power (e.g., higher than that threshold Z-score). For example, the exemplary process 200 and 210 can be implemented for MEG source imaging in a large number of subjects with neurological or psychiatric disorders. Exemplary 2D MEG frequency-power diagrams of these exemplary subjects can be converted into Z-score 2D diagram based on the determined threshold, and regions with Z-scores exceeding the threshold (e.g., established in the healthy control database) can be identified.

Fast-VESTAL Techniques

Disclosed herein are systems, devices, and techniques for implementing Fast-VESTAL, which immensely improves upon VESTAL techniques to provide enhanced computational speed and other aspects of the source images. Implementations of the disclosed Fast-VESTAL technology can potentially provide several features and advantages including (1) the ability to localize multiple correlated sources, (2) the ability to faithfully recover source time-courses, (3) the robustness to different SNR conditions including SNR with negative dB levels, (4) the capability to handle correlated brain noise, and (5) the ability to produce statistical maps of MEG source images, among others. In some implementations, the disclosed Fast-VESTAL technology can be combined with an objective pre-whitening method to handle signals with correlated brain noise to objectively separate noise and signal subspaces and successfully remove correlated brain noise from the data.

Various implementations of the exemplary Fast-VESTAL technique described herein includes analysis of human median-nerve MEG responses. For example, results of such implementations showed that the exemplary Fast-VESTAL technique can be used to easily distinguish sources in the entire somatosensory network. Also, various implementations of the exemplary Fast-VESTAL technique can include obtaining the first 3D whole-head MEG source-amplitude images from resting-state signals in healthy control subjects, for all standard frequency bands, for comparisons between resting-state MEG sources images and known neurophysiology. The exemplary data shown in this document is based on 3D whole-head MEG source-amplitude images obtained from 41 healthy control subjects. Resting-state electromagnetic signals are one of the most widely examined human brain responses, dating back to the electroencephalogram (EEG) alpha recording. For low-frequency band, a comprehensive set of source-based neuronal amplitude/power images that cover the whole brain is produced using the disclosed technology for all frequency bands for the resting-state MEG/EEG recording. Results of exemplary simulations as well as cases with real MEG human responses showed substantially low signal leaking and lack of distortion in source time-courses when compared to beamformer techniques. The MEG source-amplitude imaging method (or the square-root of the source power images) is different from MEG source covariance/functional connectivity source analyses. The former assesses strength of the neuronal sources whereas the latter examines the similarity of the shapes of the source time-courses.

Figure 3A:
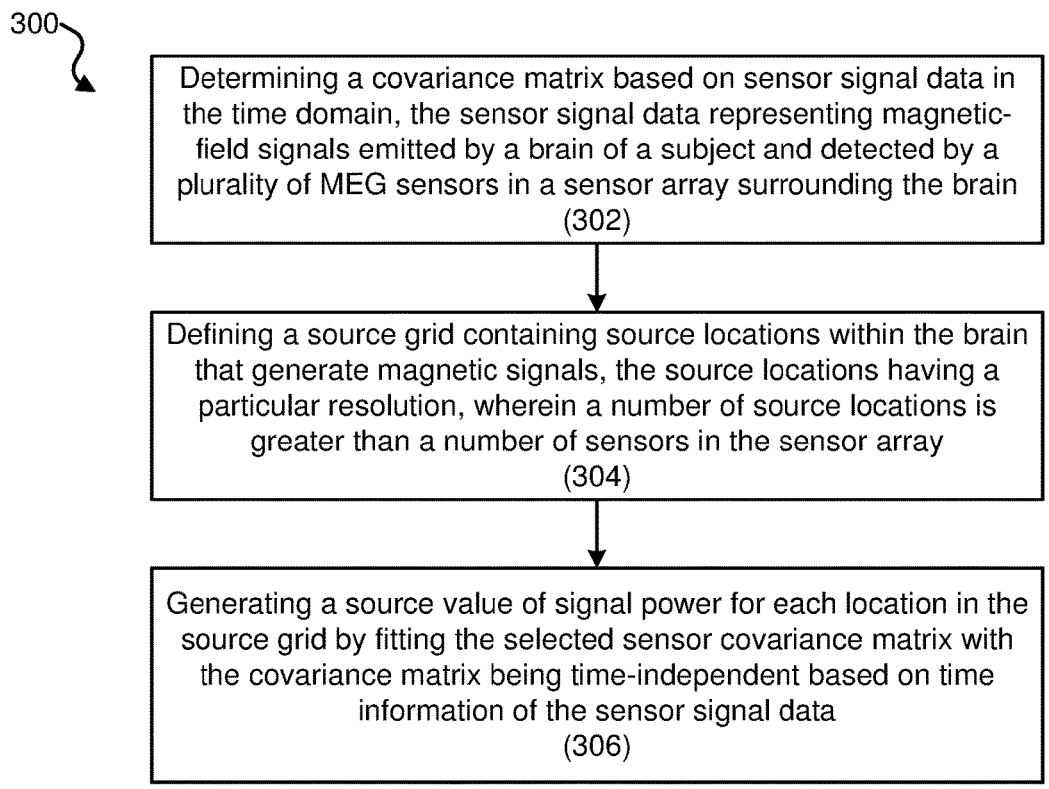
FIGS. 3A, 3B, 4A, 4B, 4C, 4D, 4E and 4F are process flow diagrams showing exemplary MEG-based Fast-VESTAL imaging processes.
Figure 3B:
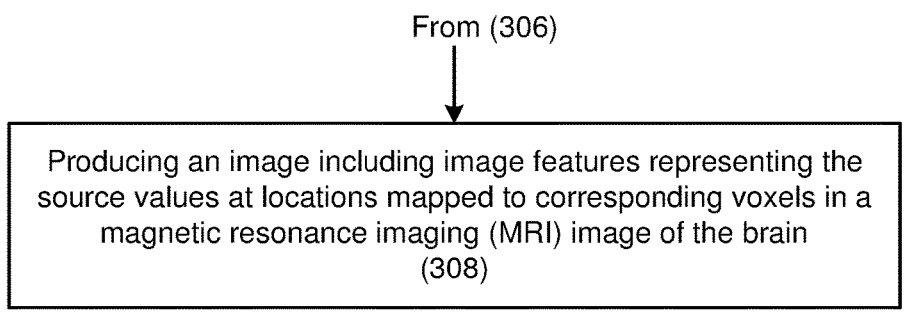

FIG. 3 is a process flow diagram showing an exemplary MEG-based imaging process (300). The MEG-based imaging process (300) can include determining a covariance matrix based on sensor signal data in the time domain, the sensor signal data representing magnetic-field signals emitted by a brain of a subject and detected by a plurality of MEG sensors in a sensor array surrounding the brain (302). The MEG-based imaging process (300) can include defining a source grid containing source locations within the brain that generate magnetic signals, the source locations having a particular resolution with a number of source locations being greater than a number of sensors in the sensor array (304). The MEG-based imaging process (300) can include generating a source value of signal power for each location in the source grid by fitting the selected sensor covariance matrix with the covariance matrix being time-independent based on time information of the sensor signal data (306). In some implementations, the MEG-based imaging process (300) can include producing an image including image features representing the source values at locations mapped to corresponding voxels in a magnetic resonance imaging (MRI) image of the brain (308).

Source Imaging of Dominant Spatial Modes Using Fast-VESTAL

Using a MEG-based system, such as system 100 described with respect to FIG. 1 above, MEG-based Fast-VESTAL imaging can be performed. FIGS. 4A, 4B, 4C, 4D, 4E and 4F are process flow diagrams illustrating an exemplary imaging process (400) for performing MEG source imaging using Fast-VESTAL. The Fast-VESTAL imaging process (400) can be implemented to obtain source amplitude images of resting-state MEG signals for different frequency bands. The Fast-VESTAL imaging process (400) includes a spatial source imaging process (402) for obtaining spatial source images. The spatial source imaging process (402) can be used to obtain L1-minimum-norm MEG source images for the dominant spatial modes of sensor-waveform covariance matrix. In addition, the Fast-VESTAL imaging process (400) includes a source time-course determining process (404) for determining source time-courses based on the spatial source images. The source time-course determining process (404) can be used to obtain accurate source time-courses with millisecond temporal resolution, e.g., using an inverse operator constructed from the spatial source images of first process. Also, the Fast-VESTAL imaging process 400 can incorporate an objective pre-whitening process (406) to objectively remove correlated brain noise as desired.

The spatial source imaging process (402) for obtaining spatial source images includes dividing a source space of a target brain of a subject into a grid of multiple potential source locations (408). One example of performing process (408) includes taking an imaging (lead-field) approach and dividing the source space (gray-matter brain volume) into a grid of thousands of potential source locations. The source grid used in Fast-VESTAL imaging process (400) is obtained by sampling a target brain area (e.g., the gray-matter areas) from MRI (e.g., T1-weighted MRI) of the subject (409). The spatial source imaging process (402) also includes using MEG sensors to detect sensor signal data representing time samples of magnetic field signals emitted by the target brain of the subject (410). The detected sensor signal data can be used to determine MEG sensor waveform signal in a data matrix format (412). For example, the MEG sensor waveform signal in time-domain B(t) in sensor-space can be expressed in a data matrix as follows: $B(t)=[b(t_1), b(t_2), \ldots, b(t_T)]$, where $t_1, t_2, \ldots, t_T$ are time samples and T is the total number of time samples and $b(t_i)$ is a M×1 vector containing the magnetic fields at M sensor sites at time sample $t_i$. The data matrix can be expressed as:

$$B(t)=GQ(t)+N(t) \qquad \text{Eq. (7,}$$

similar to Eq. 1 above)
where G is an M×2P gain (lead-field) matrix calculated from MEG forward modeling for the pre-defined source grid with P dipole locations, with each dipole location having two orthogonal orientations (i.e., θ and φ). Q(t) is a 2P×T source time-course matrix. In the spherical MEG forward head model, θ and φ represent the two tangential orientations for each dipole location, whereas in a realistic MEG forward model using the boundary element method (BEM), the θ and φ-orientations are obtained as the two dominant orientations from the singular-value decomposition (SVD) of the M×3 lead-field matrix for each dipole. The noise term N(t) in Eq. (7) is assumed to be Gaussian white noise. The MEG based system 100 performing the Fast-VESTAL imaging process (400) can determine whether correlated noise exists in the obtained MEG sensor waveform signal (406). Based on the determination at process (406), pre-whitening procedures can be applied to perform the objective pre-whitening process (408) when correlated noise is determined to exist. In the presently described technology, the objective pre-whitening method (408) can be applied to effectively remove correlated brain and environmental noise from the data matrix. The objective pre-whitening process (408) is describe further in below paragraphs. The inverse solution in Eq. (7) obtains the source time-courses Q(t) for given MEG sensor wave-forms B(t). In general, for each time-sample, since the number of unknown parameters is far greater than the number of sensor measurements (e.g., 2P>>M), MEG source imaging is dealing with a highly under-determined problem, and there are a large number of solutions that fit the data. To reduce the ambiguity, additional constraints (source models) are needed.

VEctor-based Spatio-Temporal analysis using L1-minimum norm (VESTAL) is a high-resolution time-domain MEG source imaging solution for Eq. (7) with the following exemplary properties: (1) it can model dipolar and non-dipolar sources; (2) no pre-determination of the number of sources (model order) is required; and (3) it can resolve 100% temporally correlated sources. However, VESTAL needs to analyze individual time samples $t_i$ in the time-domain signal in Eq. (7), or individual frequency bins if the MEG data are transferred into a frequency-domain signal. VESTAL's computational costs increase linearly with the number of time samples or frequency bins.

In the present Fast-VESTAL technique, the spatial source imaging process (402) can include a spatial mode determination process (414). The spatial mode determination process is used to determine a spatial modes in the MEG sensor waveform signal to remove the time dependent features. For example, the time-dependent features from Eq. (7) and only the spatial profiles are focused on. Removing the time-dependent features allows resultant MEG waveform signal to be time independent. Removing the time dependent features can be implemented by performing a SVD for the M×T MEG sensor waveform data matrix:

$$B(t) = U_B S_B V_B^T(t) \qquad \text{Eq. (8)}$$

where all temporal information in the MEG sensor waveform can be represented as a linear combination of the singular vectors in the matrix $V_B(t)$. In addition, SVD can be performed for G:

$$G = U_G S_G V_G^T \qquad \text{Eq. (9)}$$

By substituting Eqs. (8) (9) into Eq. (7) and multiplying the result with $V_B(t)$ from the right side, the following is presented:

$$U_B S_B = U_G S_G V_G^T H \qquad \text{Eq. (10)}$$

The 2P×M matrix H is called the source spatial map matrix for the given time window, and is independent of individual time samples. In the above deviation, what is used is the fact that the white noise is uncorrelated with the MEG sensor waveform (e.g., neuronal) signals $N(t)V_B^T(t) = 0$.

For each column of $U_B S_B$ a spatial mode of MEG sensor-waveforms can be determined. In Eq. (10), each spatial mode in the sensor-waveforms can be expressed as a linear combination of the corresponding source imaging maps (e.g., the columns of H). It is clear that the number of signal (e.g., dominant) spatial modes in a given MEG data set (usually ranges from a few to a tens of seconds) is substantially less than the number of time samples in the data (~100 s to ~100,000 s). Thus, by solving Eq. (10), the computational cost can be substantially reduced. This step of using temporal projection is similar to the temporal dimension reduction component of the Multiple Sparse Priors (MSP) method.

Spatial-Profile and Covariance Matrices of Sensor Waveforms

In practice, if the number of time samples is large, calculating the SVD of the sensor waveform matrix as in Eq. (8) can be time- and memory-consuming. However, $U_B S_B$ can be determined in the left hand side of Eq. (10) as the SVD of the spatial-profile of the sensor-waveform matrix $R = B(t)B(t)^T$:

$$R = B(t)B(t)^T = U_B S_B S_B^T U_B^T = U_B \Sigma_B U_B^T \qquad \text{Eq. (11)}$$

where the diagonal elements in $S_B$ are simply the square root (SQRT) of the corresponding eigenvalues of R which are the diagonal elements in $\Sigma_B$. If the MEG sensor waveforms B(t) are zero-mean across time for each MEG channel, R is the same as the sensor covariance matrix multiplied by the number of time samples T.

Fast-VESTAL Solution

Eq. (10) is under-determined, just like Eq. (7), with the number of unknown variables in each column of $H = [h_1, h_2, \ldots, h_k, \ldots, h_M]$ (e.g., 2P) much larger than the number of measurements in each column of $U_B S_B = [s_1 u_1, s_2 u_2, \ldots, s_k u_k, \ldots, s_M u_M]$ (e.g., M), so additional constraint(s) are needed to obtain a unique solution for Eq. (10). Here, the number of signal (dominant) spatial modes k is usually much smaller than the number of MEG sensor measurements M. In the present technology, for example, for individual dominant spatial modes of Eq. (10), Eq. (10) can be rewritten as:

$$U_G^T u_i s_i = S_G V_G^T h_i, i = 1, 2, \ldots, k \qquad \text{Eq. (12)}$$

To obtain the final Fast-VESTAL source image, a source imaging map is determined for each signal-related (i.e., dominant) spatial mode (416). In determining the source image map for each signal-related spatial mode, a weighing factor can be used to remove potential bias towards grid nodes (418). The Fast-VESTAL solution to Eq. (12) is:

$$\min(w^T|h_i|), \text{ subject to constraints } S_G V_G^T h_i \approx U_G^T u_i s_i, \\ i = 1, 2, \ldots, k \qquad \text{Eq. ('3)}$$

where $h_i$ is the source imaging map associated with the dominant spatial modes $u_i$ of the sensor-domain. In Eq. (13), w is a 2P×1 weighting vector chosen to remove potential bias towards grid nodes at the superficial layer and it is usually taken to be the column norm of the G matrix or a Gaussian function. In the present technology, $w = \sqrt{\text{diag}(V_G V_G^T)}$ is chosen, which removes some small bias for the reconstructed source locations in the above choices of w.

In general, for example, the solution to Eq. (13) is a non-linear minimization procedure since the source imaging maps $h_i$ (associated with dominance spatial modes $u_i$) can be either positive or negative. However, in practice, one can always replace the absolute values in $|h_i|$ with the following two sets of non-negative values related to $h_i$, and solve the set of equations through linear programming (LP). Specifically, for example, with the introduction of two new non-negative variables $h_i^a$ and $h_i^b$, Eq. (13) can be rewritten as:

$$\min(w^T(h_i^a + h_i^b)) \text{ subject to } S_G V_G^T h_i \approx U_G^T u_i s_i, h_i = h_i^a - h_i^b, i = 1, 2, \ldots, k. \qquad \text{Eq. (14)}$$

Eq. (14) can be solved readily by several LP packages. In the exemplary implementations described herein, for example, SeDuMi was used to solve the above equation-set to get source imaging map for each dominant spatial mode of sensor-domain signal. This exemplary step is repeated for all dominant spatial modes to obtain the final Fast-VESTAL source image matrix. The computational cost of Fast-VESTAL is proportional to the number of dominant (signal-related) spatial modes which is usually much fewer than the number of time samples.

The Fast-VESTAL source imaging result can be plotted on the source grid as:

$$A = \sqrt{\text{diag}(HH^T)/T} \qquad \text{Eq. (15)}$$

which is the 2P×1 root-mean-square (RMS) source amplitude value, mean across time at each grid node. The main feature of A is that it is highly sparse, with many of its elements being either zero or close to zero, as a direct consequence of L1-norm minimization.

One problem that should be addressed by the minimum L1-norm approach is that the solution has a small tendency (bias) towards the coordinate axes. To address the bias towards the coordinate axes, the weighing factor in process (418) can include a correction factor (420). For example, in spherical MEG head model, for a dipole at the $i^{th}$ node of the grid, the vector-based L1-minimum norm solution can also be expressed as minimizing $$\sum_{i=1}^{P} w_i \omega_i (|\cos(\psi_i)| + |\sin(\psi_i)|)$$

where $\psi_i$ is the angle between total dipole moment and the orientation of the elevation in a tangential plane containing the dipole node, and $\omega_i = \sqrt{(\omega_i^\theta)^2 + (\omega_i^\phi)^2}$ is the non-negative dipole strength. This can introduce a bias towards the coordinate axes. To handle this small bias, an additional correction factor $(|\cos(\psi_i^e)|+|\sin(\psi_i^e)|)^{-1}$ was included in the weighting vector w in Eq. (14) for one more iteration, where $\psi_i^e$ is the angle associated with the estimated orientation based on L1-minimum norm solution without the correction factor.

Obtaining Source Time-Courses in Fast-VESTAL

An exemplary primary advantage of MEG over other functional imaging techniques (e.g., fMRI and PET) is its excellent temporal resolution. To capitalize on this, it is essential that a source imaging approach not only accurately localizes the neuronal activities, but also faithfully recovers the source time-courses with high temporal resolution.

In the present technology, for example, the spatial images obtained by Fast-VESTAL in Eq. (15) were used to obtain the source time-courses. Determining the source time-course using the spatial images in process (404) can include constructing an inverse operator matrix based on the Fast-VESTAL spatial image (422), and applying the constructed inverse operation to the sensor waveform signal in matrix form B(t) (424). An inverse operator matrix that can be directly applied to the sensor waveform matrix B(t) can be developed as follows. First, for example, the Fast-VESTAL spatial image in Eq. (15) is assigned as a weighting variable to the gain (lead-field) matrix:

$$\tilde{G} = G \bullet (JA^T)$$  Eq. (16)

where $J = [1, 1, \ldots, 1]^T$ is a M×1 vector of ones, and • indicates the element-wise matrix product. $\tilde{G}$ is the weighted gain (lead-field) matrix with each of the 2P columns weighted by the 2P elements from A in Eq. (15). Since the source maps from the Fast-VESTAL are highly sparse with most of its elements being zero or near zero, the weighted gain matrix G is also sparse. Using the SVD of this weighted gain matrix, $$\tilde{G} = U_{\tilde{G}} S_{\tilde{G}} V_{\tilde{G}}^T$$  Eq. (17)

the linear inverse operator for G can be constructed as:

$$\tilde{G}^+ = V_{\tilde{G}}(S_{\tilde{G}} + \alpha I)^{-1} U_{\tilde{G}}^T$$  Eq. (18)

in which I is an identity matrix and $\alpha$ is the regularization parameter. Using a linear inverse operator matrix, such as $\tilde{G}^+$, the reconstructed, best-fitting, source time-courses of Fast-VESTAL solution can be obtained:

$$\hat{Q}(t) \approx [\tilde{G}^+ \bullet (AJ^T)]B(t) = \tilde{G}_A^+ B(t)$$  Eq. (19)

Here, the inverse operator matrix $\tilde{G}_A^+$ can be called the Fast-VESTAL source time-course operator. The millisecond-by-millisecond source time-course matrix $\hat{Q}(t)$ is obtained by applying $\tilde{G}_A^+$ to the sensor waveform matrix B(t) as shown in Eq. (19). In short, the estimated Fast-VESTAL source time-course $\hat{Q}(t)$ is related to the A in Eq. (19), and A is related to Fast-VESTAL spatial source map matrix H in Eq. (15).

Goodness-of-Fit to the MEG Sensor Signals

Figure 4A:
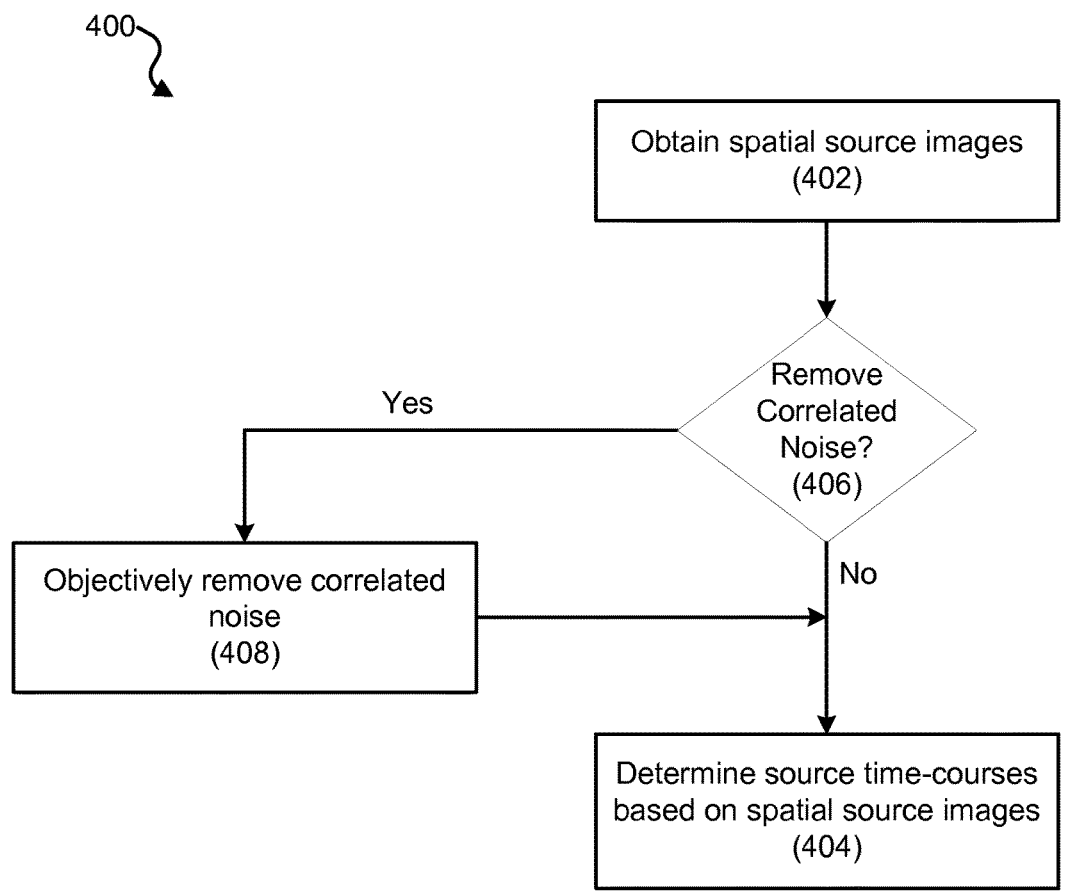
Figure 4B:
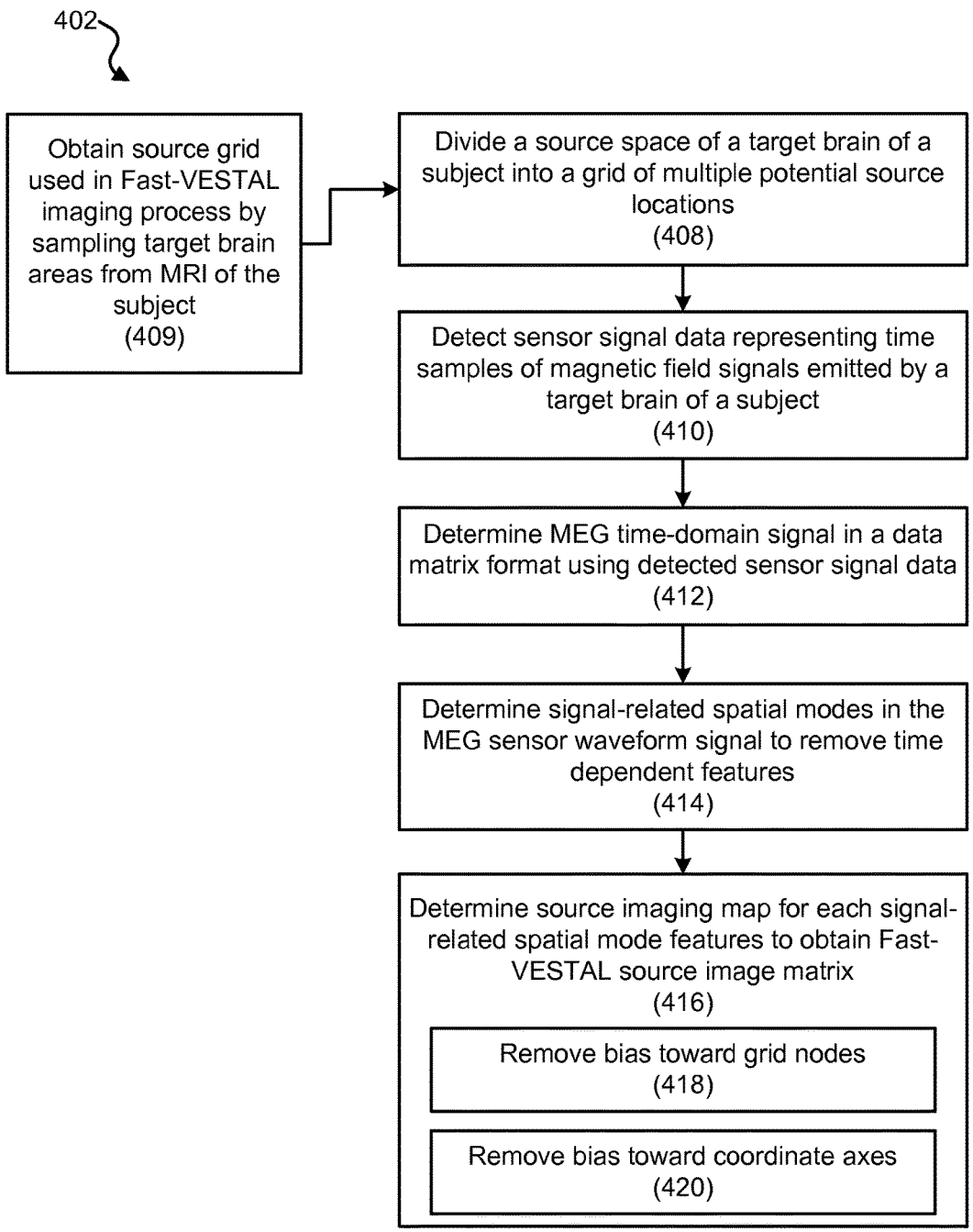
Figure 4C:
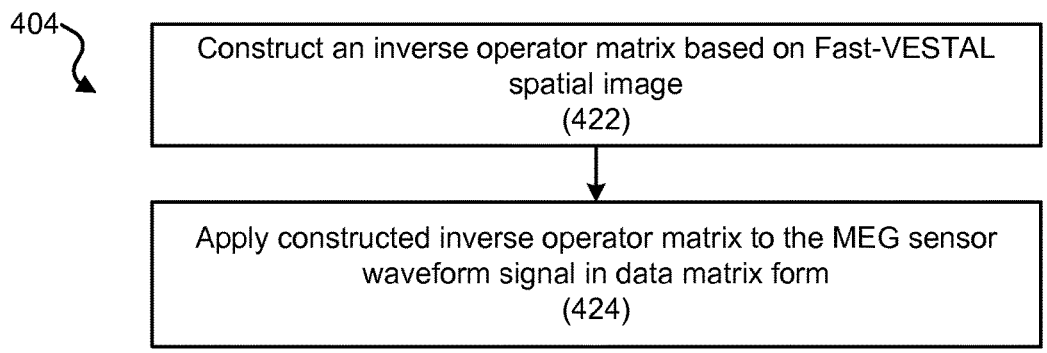
Figure 4D:
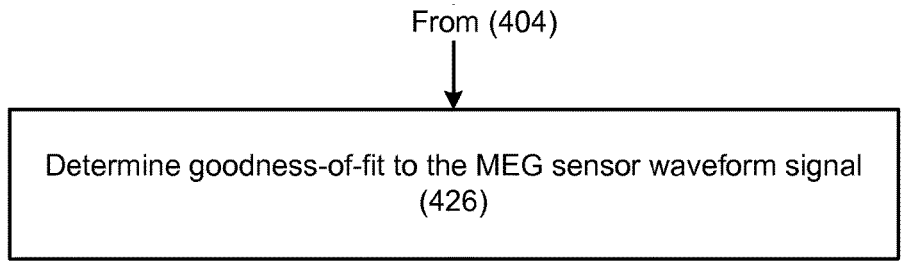
Figure 4E:
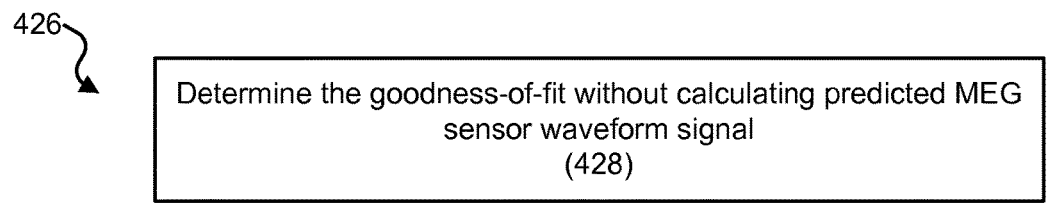
Figure 4F:
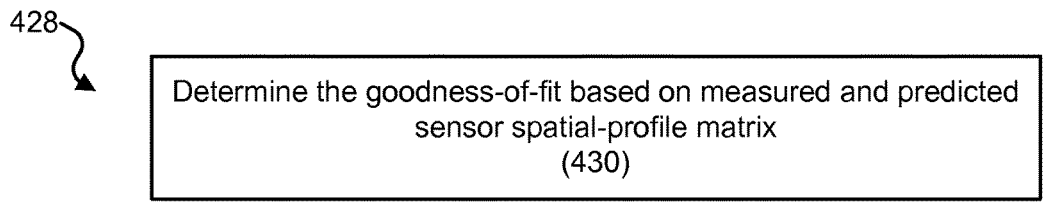

As shown in FIG. 4D, the MEG based imaging process 400 can include determining the goodness-of-fit to the MEG sensor waveform signal (426) using the source time-courses determined at process (404). The goodness-of-fit to the MEG sensor waveform may be obtained by comparing the predicted sensor waveform using the best-fitting source time-courses from Eq. (19) to the measured MEG sensor waveforms. For example, the goodness-of-fit can be calculated directly from Eq. (19) without having to calculate the predicted MEG sensor waveforms (428) as shown in FIG. 4E. In this exemplary approach, the best-fitting source spatial-profile matrix or the source covariance matrix can also be obtained as:

$$\hat{R}_{SOURCE} = \tilde{G}_A^+ R \tilde{G}_A^{+T}$$  Eq. (20)

Then, the best-fitting sensor spatial-profile matrix or the sensor covariance matrix can be expressed as:

$$\hat{R} = G \hat{R}_{SOURCE} G^T$$  Eq. (21)

The goodness-of-fit measure of the MEG sensor signals is then calculated based on measured and the predicted sensor spatial-profile matrix or the sensor covariance matrix (430). See FIG. 4F. For example, the goodness-of-fit measure of the MEG sensor signals can be determined using the diagonal elements of both the measured and the predicted sensor spatial-profile matrix or the sensor covariance matrix:

$$\text{Goodness\_of\_fit} = \left(1 - \frac{\sum_{i=1}^{M}(R_{ii} - \hat{R}_{ii})^2}{\sum_{i=1}^{M} R_{ii}^2}\right) \times 100\%$$  Eq. (22)

Exemplary Computer Simulations Using White Noise

In the present technology, exemplary computer simulations were used to assess three key issues related to the performance of Fast-VESTAL, e.g., 1) the algorithm's ability to localize multiple correlated sources, 2) the algorithm's performance for different SNR conditions with white as well as real brain noise, and 3) the algorithm's accuracy of reconstruction of source time-courses.

Figure 5A:
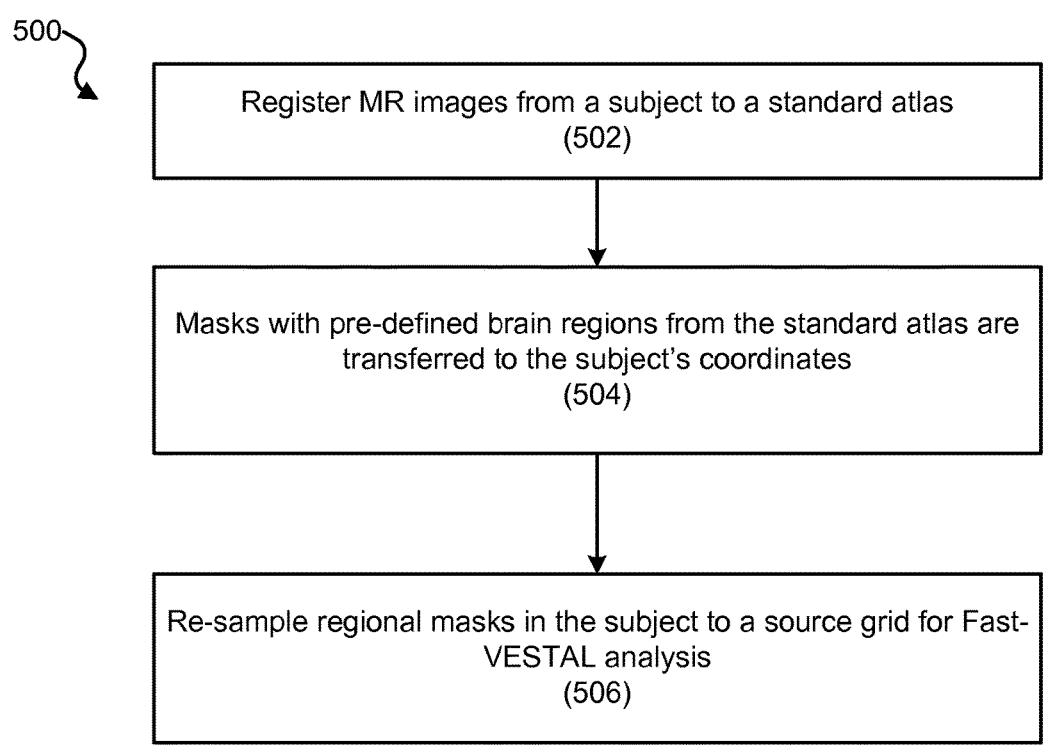
FIG. 5A is a process flow diagram showing an exemplary process for performing a computer simulation to assess Fast-VESTAL performance.

FIG. 5A is a process flow diagram showing an exemplary process for performing a computer simulation to assess Fast-VESTAL performance (500). The process (500) is used to obtain source grid used by Fast-VESTAL process by obtaining MR images from a subject's brain. For example, the source grid used by Fast-VESTAL was obtained by sampling the gray-matter areas from the T1-weighted MRI of each subject. The processing pipeline for assessing Fast-VESTAL performance (500) includes the following exemplary steps. (1) T1-weighted MR images from a subject is registered to a standard atlas (502). For example, the T1-weighted MR images from a subject can be registered to a standard atlas (e.g., MNI-152) using registration programs in FSL (www.fmrib.ox.ac.uk/fsl/). (2) Masks with pre-defined brain regions from the standard atlas are transferred to the subject's coordinates (504). For example, the cortical, subcortical, and cerebellum gray-matter masks with pre-defined brain regions from the standard atlas in FSL can be transferred to the individual subject's coordinates, using the inverse of the transformation in process (502). In process (504), the Harvard-Oxford Atlas (part of the FSL software) can be used to parcellate gray matter into 96 cortical gray-matter regions (48 in each hemisphere), 15 subcortical gray-matter regions, and the cerebellum. (3) Regional masks in the subject are re-sampled to a source grid for Fast-VESTAL analysis (506). For example, the regional masks in the subject can be re-sampled to a cubic source grid with 5 mm size for Fast-VESTAL analysis, which leads to a grid with ~7,000 nodes. Realistic BEM head model was used for MEG forward calculation, with the BEM mesh obtained from tessellating the inner skull surface from the MRI into ~6000 triangular elements with ~5 mm size.

Figure 5B:
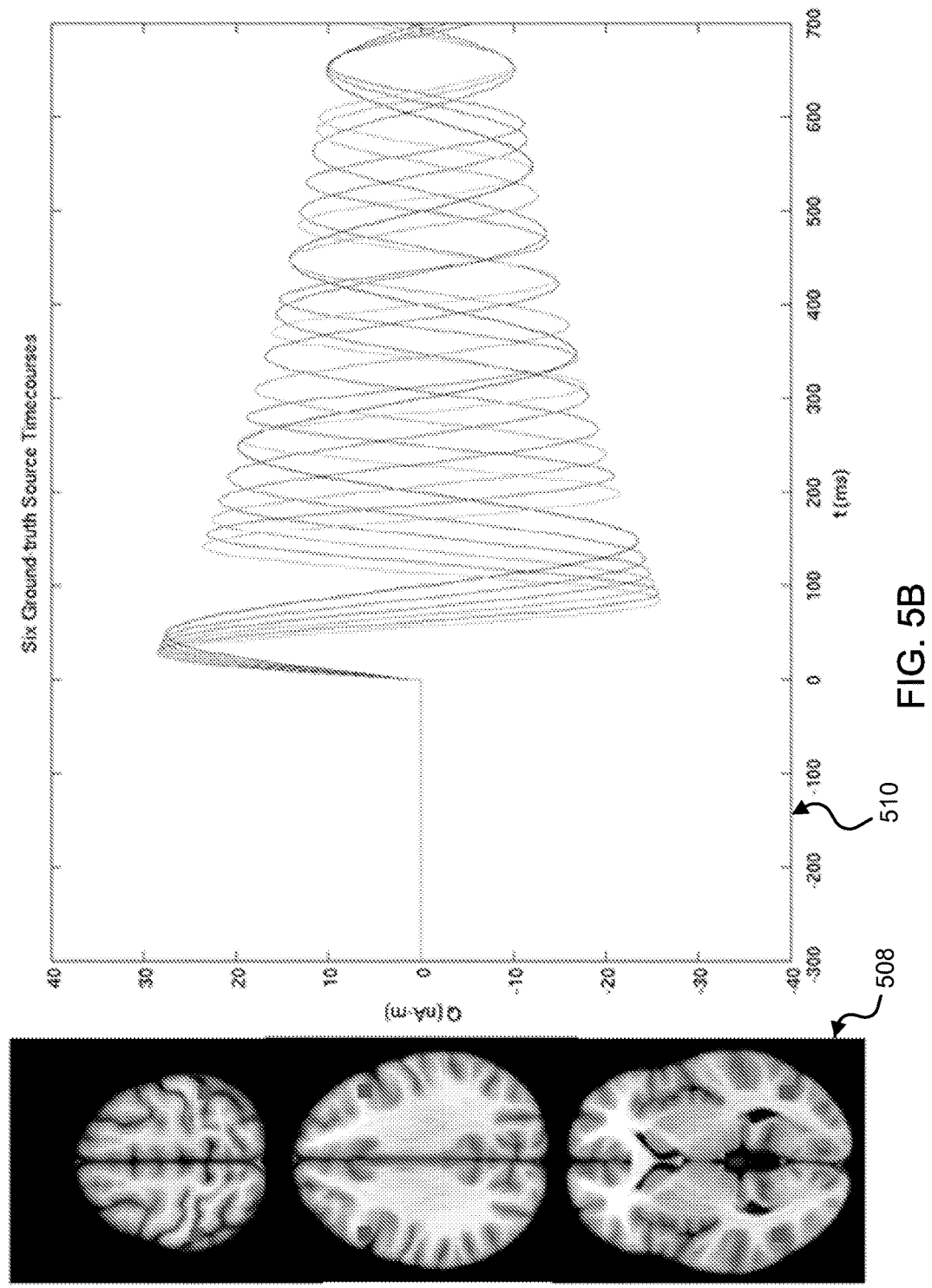
FIG. 5B shows, in the left panel, ground-truth locations of six simulated sources, and in the right panel, six correlated source time-courses used in computer simulations to mimic evoked response, with 300 ms for pre-stimulus and 700 ms for post-stimulus intervals.

FIG. 5B shows, in the left panel 508, ground-truth locations of six simulated sources, and in the right panel 510, six correlated source time-courses used in computer simulations to mimic evoked response, with 300 ms for pre-stimulus and 700 ms for post-stimulus intervals. The performance of Fast-VESTAL was first examined using six simulated dipolar sources (FIG. 5B, left panel). Correlated source time-courses (ground-truth) were assigned to these sources to mimic evoked responses with 300 ms pre-stimulus and 700 post-stimulus intervals (FIG. 5B, right panel). MEG sensor waveforms were calculated using the BEM model for the sensor configuration of Elekta/Neuromag VectorView™ whole-head MEG system (Elekta-Neuromag, Helsinki, Finland) with 306 MEG channels that contains 204 planar gradiometers and 102 magnetometers. These 6 sources were placed as follows: two at L-R middle frontal gyri, two in L-R postcentral gyri and superior parietal lobules, and two in L-R lateral occipital cortex (FIG. 1B). The ground-truth orientations of these 6 sources were [−0.14, −0.75, 0.64], [−0.52, 0.40, 0.76], [−0.78, 0.17, −0.60], [0.01, 0.99, 0.11], [−0.16, 0.14, 0.98], and [0.47, 0.80, −0.37], respectively. Three different levels of random white noise were added to the sensor wave forms to examine Fast-VESTAL's performance in reconstructing the source locations and source time-courses. After adding the three levels of white noise, the SNRs of the noisy MEG sensor waveforms were at 3.74 (White-noise Level-1), 1.24 (White-noise Level-2), and 0.53 (White-noise Level-3) respectively for the entire interval, and were at 4.46, 1.48, and 0.64 respectively for the post-stimulus interval, measured by Frobenius norms (see the Exemplary Results section). Since statistical analyses (see below) depend on some noise in the pre-stimulus interval, a negligible amount of white noise ("Level-0") was added to the noiseless MEG sensor waveform with the SNR>$10^6$. Since the SNR was so high for Level-0, this condition is referred to as "Noiseless" throughout this document.

The selection of the number of dominant signal modes k in $S_B$ in Eq. (10) is straightforward for data with white noise. The selection of k was based on the "L-shaped" nature of the singular value curve of the MEG sensor signal in Eq. (8) or equivalently the SQRT of eigenvalues of the sensor covariance matrix in Eq. (11), e.g., allowing to effectively separate the signal subspace from the noise subspace (see the Exemplary Results section).

Objective Pre-Whitening Method to Handle Correlated Brain Noise with Pre-Whitening, Eigenvalue Plots, and Objective Threshold When studying human MEG responses, correlated environment noise and especially brain noise are common; this is different from white noise. In situations with correlated noise, the determination of signal (e.g., dominant) spatial modes k becomes challenging. The disclosed pre-whitening method can be implemented to handle correlated noise. In these exemplary implementations described using simulated correlated noise, if one has complete knowledge of the correlated noise, the pre-whitening step effectively determines the signal subspace and removes the correlated noise. However, it is still a topic of research how to handle correlated brain noise in realistic situations when only incomplete or non-simultaneously collected information about the correlated noise is available. An example is evoked MEG responses, wherein brain (correlated) noise can be estimated during the pre-stimulus interval, but not during the post-stimulus interval when the evoked signal mixes with the brain noise. Another example is when brain noise used for pre-whitening is collected before or after the actual task session. So in practice, one must find: 1) an objective way to measure the efficacy of the pre-whitening step, 2) an additional procedure to further remove residual correlated noise when pre-whitening step is not completely successful, and 3) an objective way to identify noise subspace in the pre-whitened signal covariance matrix.

Figure 6:
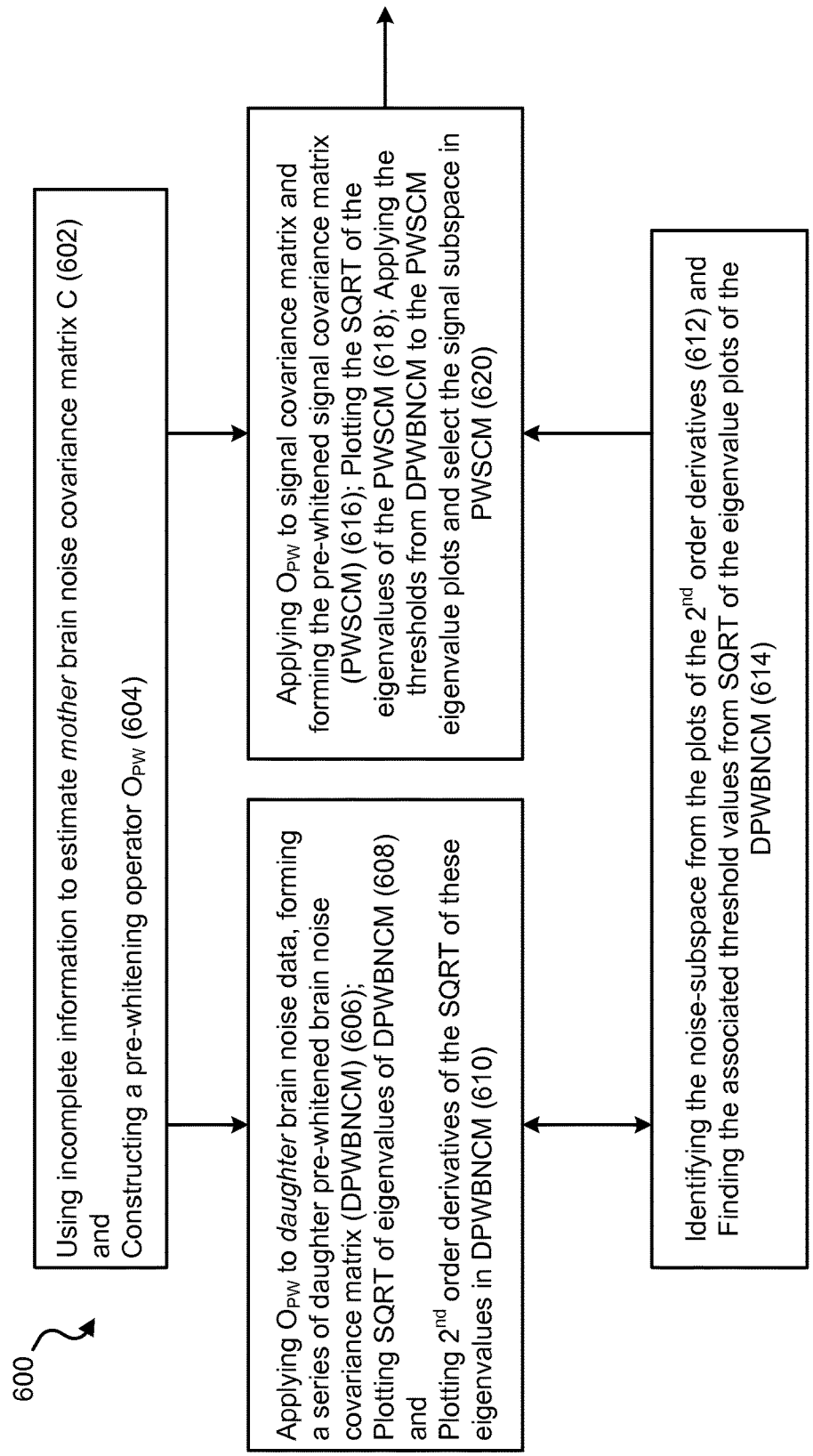
FIG. 6 shows a flow-chart of an exemplary Objective Pre-whitening Method (OPWM) of the present technology for removing correlated brain noise from the data. The same process was applied to remove correlated environmental noise when replacing the daughter pre-whitened brain noise covariance matrices (DPWBNCM) in the chart with the daughter pre-whitened empty-room covariance matrix (DP-WERCM).

In the present technology, a new Objective Pre-whitening Method (OPWM) is disclosed to address the above challenges for effectively removing correlated brain noise. FIG. 6 shows an exemplary OPWM (600). The exemplary OPWM (600) of the disclosed technology includes the following. A "mother" correlated brain noise covariance matrix is estimated based on incomplete information (602) and a pre-whitening operator (see below) is constructed (604). The constructed pre-whitening operator is applied to a series of "daughter" brain noise data sets, thereby forming a series of daughter pre-whitened brain noise covariance matrices (DPWBNCM) (606). Also, the SQRT of eigenvalues of the formed DPWBNCM is plotted (608), and the second-order derivatives of the SQRT of eigenvalues of DPWBNCM are plotted (610). If the pre-whitening process does not completely remove the correlated brain noise (it is often the case), the leading second-order derivatives will be substantially different from zero. The noise-subspace is identified from the plots of the second-order derivatives of eigenvalues of DPWBNCM (612) and the associated threshold values are found from the SQRT of the eigenvalue plots of the DPWBNCM (614). Also, the pre-whitening operator can be applied to the signal covariance matrix to obtain the pre-whitened signal covariance matrix (PWSCM) (616). The SQRT of the eigenvalues of the PWSCM is plotted (618). The thresholds from the DPWBNCM in (614) can be applied to the PWSCM eigenvalue plots (618) and the signal subspace in the PWSCM can be selected (620).

Pre-Whitening Process:

In the pre-whitening process, a pre-whitening operator is constructed. For example, eigenvalue decomposition (EVD) was performed on an estimated mother noise covariance matrix (see later for how to obtain such a matrix) $C = U_C \Omega_C U_C^T$, and then constructed a pre-whitening operator:

$$O_{PW} = U_C \Omega_C^{-1/2} U_C^T \qquad \text{Eq. (23)}$$

The pre-whitening operators is applied a to the gain matrices in Eqs. (7)(8)(17), MEG sensor waveforms in Eqs. (7)(8)(19), or sensor covariance matrices in Eqs. (11)(20):

$$G_{PW} = O_{PW} G; \ \tilde{G}_{PW} = O_{PW} \tilde{G}; \ B(t)_{PW} = O_{PW} B(t);$$
$$R_{PW} = O_{PW} R O_{PW}^T, \qquad \text{Eq. (24)}$$

The rest of the formulation of Fast-VESTAL takes the same format when replacing these matrices with their corresponding pre-whitening ones. Note that after the pre-whitening step, the MEG sensor waveforms and sensor covariance matrices will become dimensionless (i.e., ratio scores). In the exemplary implementation of Eq. (23), the calculation of $\Omega_C^{-1/2}$ was based on the top 60 largest singular values in $\Omega_C$, due to the fact that the later matrix becomes rank 64 after applying MaxFilter to any data set in the Elekta MEG system.

Brain-Noise Data:

In order to examine the robustness of Fast-VESTAL in realistic situations of correlated brain noise, MEG brain noise were collected from a healthy subject watching a fixation point for over 2 hours, in multiple sessions of 5-minute recordings from different days. After co-registering these data sessions and removing epochs containing eye-blinks, eye-movements, and other artifacts using Max-Filter (see below), the fixation brain signals were divided into a pool of over 6,100 epochs that were free of artifacts, each of 1000 ms duration. Using these data, constructed were three levels of brain noise that matched the noise levels of the three white-noise conditions based on Frobenius norms. The numbers of randomly selected epochs for signal averaging in each of the three brain-noise conditions were: 125, 14, and 3, respectively. These conditions were referred as brain-noise Levels-1, 2, and 3.

Assessing the Efficacy of Pre-Whitening Using Only Brain-Noise Data:

Before the realistic brain noise was added to the simulated signal to challenge the performance of the Fast-VESTAL algorithm, examined was the robustness of the estimated mother noise-covariance matrix in removing correlated brain noise. In practice, for example, the estimation of the mother noise covariance is always based on partial information. Thus, the estimated mother covariance matrix of correlated brain noise was constructed using the pre-stimulus interval partial data (not the entire interval), e.g., assuming that the pre-whitening step removes the correlated noise for the entire interval, including the post-stimulus section.

A Monte-Carlo approach was used to evaluate the efficacy of the pre-whitening approach. For each brain-noise condition, 40 sets of epochs were randomly selected, each epoch lasting 1000 ms, from a pool of over 6,100 epochs of human brain-noise recordings. Specifically, for example, for the brain-noise Level-1 condition, each of the 40 sets of epochs contained 125 trials that were then averaged (i.e., 5,000 total epochs). In each set, estimated was the mother brain-noise covariance matrix from the first 300 ms interval of the averaged data, and ran the pre-whitening step through the entire 1000 ms interval (e.g., daughter brain-noise condition) using Eqs. (23) and (24). Next, plotted was the SQRT of the eigenvalues of the daughter pre-whitened brain-noise covariance matrix (DPWBNCM) for the entire interval. As shown in the exemplary Results Section, these plots and their second-order derivatives objectively assess the quality of the pre-whitening step and provided an objective way to separate signal subspace from the noise subspace. This procedure was repeated for the conditions with brain-noise Level-2 (14 trials averaging) and Level-3 (3 trials averaging). It is important to emphasize that there was no addition of any simulated signal during this procedure—only brain-noise data were involved in the exemplary analyses.

Analyzing Human Median-Nerve MEG Response

The performance of Fast-VESTAL was further examined using human MEG responses evoked by unilateral median-nerve stimulation. This task is particularly relevant because an excellent understanding of the underlying neuronal activity allows prediction with a high degree of confidence where sources should be found, and hence to confirm or refute the correctness of the calculated source localizations. MEG recordings were conducted from a healthy subject as he underwent right median-nerve stimulation using a bipolar Grass™ constant current stimulator. The stimuli were square-wave electric pulses (0.2 ms duration) delivered at about 1 Hz (ISI: 800 ms to 1200 ms). The intensity of the stimulation was adjusted until robust thumb twitches were observed. Magnetic fields evoked by median-nerve stimulation were measured using an Elekta/Neuromag™ whole-head Vectorview™ MEG system in a 6-layer magnetically shielded room (IMEDCO-AG, Switzerland). EOG electrodes were used to detect eye blinks and eye movements. An interval of 500 ms post-stimulus was recorded, using 300 ms pre-stimulus data for constructing the noise covariance matrix for pre-whitening. Data were sampled at 1000 Hz and run through a high-pass filter with 0.1 Hz cut-off and through a notch filter (58-62 Hz) to remove 60 Hz powerline noise. Two hundred artifact-free responses were averaged with respect to the stimulus trigger to increase the SNR. Maxfilter, also known as signal space separation, was used to remove external interferences. A five-minute session of resting-state brain noise (eyes-open), collected from the same subject on a different day, was used to examine the efficacy of the pre-whitening step and to identify the noise subspace.

MEG Resting-State Recordings in Healthy Subjects

To examine the performance of Fast-VESTAL technique for spontaneous data, applied was the exemplary Fast-VESTAL technique to obtain whole-brain source imaging for resting-state MEG data in standard frequency bands. Study participants included 41 healthy control subjects with no history of neurological or psychiatric disorders (age 26.7±8.4 years, 34 males). Three blocks of resting-state MEG data with eyes-closed for 5 minutes were collected for each block using the Elekta/Neuromag VectorView™ whole-head MEG system at the UCSD MEG Center. During the recording, subjects were instructed to keep their eyes closed and empty their mind. Data were sampled at 1000 Hz and were run through a high-pass filter with 0.1 Hz cut-off and a low-pass filter with 330 Hz cut-off. Eye blinks, eye movements, and heart signals were monitored. Precautions were taken to ensure head stability: foam wedges were inserted between the subject's head and the inside of the unit, and a Velcro strap was placed under the subject's chin and anchored in superior and posterior axes. The head positions were measured, e.g., with the head movement across different sessions was less than 5 mm (usually 2-3 mm).

MEG eyes-closed data were first run through MaxFilter to remove external interferences (e.g., magnetic artifacts due to metal objects, strong cardiac signals, environment noise, etc.), and to co-register the MEG data by removing the small head movements across the three 5-min eyes-closed sessions. Next, residual artifacts near the sensor array due to eye movements and residual cardiac signals were removed using Independent Component Analysis. The software is a customized version of ICALAB (bsp.brain.riken.jp/ICALAB/). The EKG artifacts in the MEG data were also removed when the MEG data were passed through MaxFilter. In some examples, removal of EKG artifacts using MaxFilter can be straightforward since EKG signals clearly represent magnetic fields in the Vector Spherical Harmonic Expansion (in signal space separation), external to the MEG sensor array.

Structural MRIs of the subject's head were collected using a General Electric 1.5 T Excite MRI scanner (ver. 14 software release). The acquisition contains a standard high-resolution anatomical volume with a resolution of 0.94× 0.94×1.2 $mm^3$ using a T1-weighted 3D-IR-FSPGR pulse sequence. To co-register the MEG with MRI coordinate systems, three anatomical landmarks (e.g., left and right pre-auricular points, and nasion) were measured for each subject using the Probe Position Identification system (Polhemus, USA). By identifying the same three points on the subject's MR images using MRILAB software developed by Elekta/Neuromag, a transformation matrix involving both rotation and translation between the MEG and MR coordinate systems was generated. To increase the reliability of the MEG-MR co-registration, approximately 80 points on the scalp were digitized with the Polhemus system, in addition to the three landmarks, and those points were co-registered onto the scalp surface of the MR images. The MEG-MR co-registration error was expected to be less than 3 mm, e.g., based on the MEG median-nerve task that reliably produces primary somatosensory cortex responses for hand representations that are associated with unique anatomical landmarks. The T1-weighted images were also used to extract the innermost skull surface (e.g., SEGLAB software developed by Elekta/Neuromag). The innermost skull surface was used to construct a realistic head model for MEG forward calculation based on the BEM model.

To analyze the human resting-state data and assess statistical significance (see below), also analyzed were 41 sets of "empty-room" data sets that were acquired when no human subjects were inside the MEG scanner. An extra set of empty-room data were used to estimate the mother noise covariance matrix in the exemplary OPWM step. These empty-room data sets (each lasting about 2 minutes) were collected over a 3-year period that coincided with the human resting-state recordings. The exemplary OPWM developed for simulated signal with brain noise and the human median-nerve response was applied in the resting-state data analyses. Here, to remove the correlated noise from the environment, first, an estimated mother noise covariance matrix was constructed using the extra empty-room data set, and the pre-whitening operator Eq. (23) was built from the mother noise covariance matrix. Next, the pre-whitening operator was applied to each of the 41 daughter empty-room data sets to create the daughter pre-whitened empty-room covariance matrices (DPWERCM). The SQRT of the eigenvalues from such DPWERCM provided the objective threshold for distinguishing noise subspace from the signal subspace. This exemplary threshold was used in the Fast-VESTAL analysis of the pre-whitened data covariance matrices for the 41 empty-room data sets and the resting-state data from 41 human subjects (see Exemplary Results Section). For example, for comparison, beamformer analysis was applied to the same 82 pre-whitened data sets.

Exemplary Assessment of the Statistical Significance of the Fast-VESTAL Results

The exemplary implementations included developing an approach to assess the statistical significance of the exemplary Fast-VESTAL results, which can then be used to construct statistical maps of the neuronal activities. For the simulation data with different noise levels, F-tests assessed the variances between the post-stimulus 700 ms interval over the pre-stimulus 300 ms interval for each grid node. The F-value maps for the Fast-VESTAL solution were constructed for the ~7000 grid nodes. False discovery rate (FDR) corrected for multiple comparisons (corrected p=0.01) was employed. Additional thresholding based on the post-stimulus RMS value of 0.3 nA-m was applied. Grid nodes with activities below such threshold were considered not detectable and excluded from the statistical analysis.

For example, to assess statistical significance in the analyses of resting-state MEG data, Fast-VESTAL was used to analyze 41 data sets from human resting-state recordings and 41 empty-room data after pre-whitening and objective selection of the signal subspace (see above). After a square-root transformation, all source images were registered to the MNI-152 brain-atlas coordinates using FLIRT software in FSL, and spatially smoothed using 5-mm Gaussian kernel to reduce inter-subject anatomical difference. The Fast-VESTAL results from the empty-room data sets served as the control group to evaluate the statistical significance of source amplitudes from the human resting-state data in two-tailed t-tests. T-test values were plotted as statistical maps across the grid nodes, using FDR correction (corrected p=0.01). The same statistical procedures were applied to the source images obtained from beamformer.

Other Exemplary Parameter Settings in Fast-VESTAL

As with any MEG source imaging techniques, optimal performance of Fast-VESTAL depends on the settings of certain parameters. For example, in Fast-VESTAL, three parameters need to be set: (1) the number of dominant singular values in $S_G$ from the SVG of the MEG gain (lead-field) matrix G in Eq. (10); (8) the regularization parameter a in the inverse operator $\tilde{G}^+$ in Eq. (18) to obtain the Fast-VESTAL source time-courses; and (3) the number of dominant signal modes k in $S_B$ from the SVD of the MEG sensor waveform in Eq. (2), or equivalently in the sensor covariance matrix in Eq. (11) for white-noise conditions; and the corresponding ones in Eq. (24) for signal with correlated brain noise after the pre-whitening step. The disclosed approach can differentiate noise subspace from the signal subspace and objectively estimate dominant signal modes k, for the conditions with real correlated brain noise.

For example, the setting of the other two parameters was straightforward without any iterations and/or updating procedures: in all simulations and processing of empirical MEG data using the exemplary Fast-VESTAL technique, the parameter a was set at 5% of the largest singular values in $S_{\tilde{G}}$ in Eq. (18); the number of dominant singular values in $S_G$ was set to 80 in Eq. (10) and all other smaller singular values in $S_G$ were set to be zero. These exemplar settings were independent of the MEG signals or the noise levels (see Exemplary Results Section).

Exemplary Results Section

Exemplary Computer Simulation Results with White Noise, Corrected Sources, and Different SNRs Different levels of white noise were added to the MEG sensor waveforms calculated from the 6 sources, which are shown in FIG. 7(A)(E)(I)(M) where 204 planar gradiometers were super-imposed. SNR was defined as the ratio of the Frobenius norms of the noiseless MEG sensor waveform matrix over the random white sensor noise waveform matrix. For the whole 1000 ms time interval, the SNRs for the simulated noisy data sets were at $1.86 \times 10^6$ (125.4 dB); 3.74 (11.45 dB); 1.24 (1.90 dB); and 0.53 (−5.49 dB), corresponding to noise Levels 0 ("noiseless"), 1, 2, and 3 respectively. For just the post-stimulus interval, the SNRS were at $2.23 \times 10^6$ (126.9 dB) for the "noiseless" Level-0; at 4.46 (12.90 dB) for Level-1; at 1.48 (3.45 dB) for Level-2; and at 0.64 (−3.95 dB) for Level-3. Fast-VESTAL was used to reconstruct the source locations and source time-courses. In all cases, the number of dominant signal modes in $S_B$ (i.e., size of the signal subspace) was selected to be 6, based on the "L-shape" singular value curve (see below). Standard-VESTAL and beamformer were also used to reconstruct the location and source time-courses. The noise features in the sensor waveforms from 110 magnetometers was similar (not shown) to that of the gradiometers.

Source Time-Course Reconstruction:

The 6 source time-courses reconstructed by Fast-VESTAL (Eq. (19)) for the noise levels 0-3 are shown in FIG. 7(B)(F)(J)(N). Good reconstructions, in terms of shape, onset, and amplitude, were obtained for all 6 source time-courses, including the high-noise-level condition. In calculating each of the reconstructed source time-courses, summed up were the activities via SVD from all voxels within 10 mm from the center voxel with the strongest activities in each of the 6 clusters.

The reconstructed source time-courses from the Standard-VESTAL (FIG. 7(C)(G)(K)(O)) were highly similar to those from the Fast-VESTAL, although more noise were seen in the standard VESTAL results for the high noise levels (FIG. 7(K)(O)). For noise Level-0 (noiseless), the reconstructed source time-courses from both Fast-VESTAL (FIG. 7(B)) and Standard-VESTAL (FIG. 7(C)) were virtually identical to the ground-truth source time-courses with strong correlations (FIG. 5B). In addition, beamformer was used to analyze the same simulated data with the reconstructed source time-courses shown in FIG. 7(D)(H)(L)(P). In beamformer solutions, select were the nodes with maximum F-values (see below) within 10 cm from the true source locations. All constructed source time-courses using beamformer exhibited substantial distortions, even for the noiseless condition.

Table 1 shows (1) the percent variance explained (PVE) in the reconstructed source time-courses; (2) PVE of inter-source cross correlation (ICC) among reconstructed source time-courses (e.g., shown in lower-left triangle 800, 802, 804, 806 in FIG. 8). The exemplary comparisons are made for the solutions from Fast-VESTAL, Standard-VESTAL, and Beamformer, and arranged separately for white noise (left half) from the real brain noise (right half). Orientations errors were also listed.

The rest of the ICC values (highlighted by the white triangle 800 in the lower-left corner) vary from 0.01 to 0.40. The ICC from both Fast-VESTAL in FIG. 8(B) and Standard-VESTAL in FIG. 4(C) for the white-noise Level-1 condition closely matched the ground truth. In contrast, ICC from the beamformer reconstructed source time-courses showed markedly reduced correlations over the ground truth.

Figure 8:
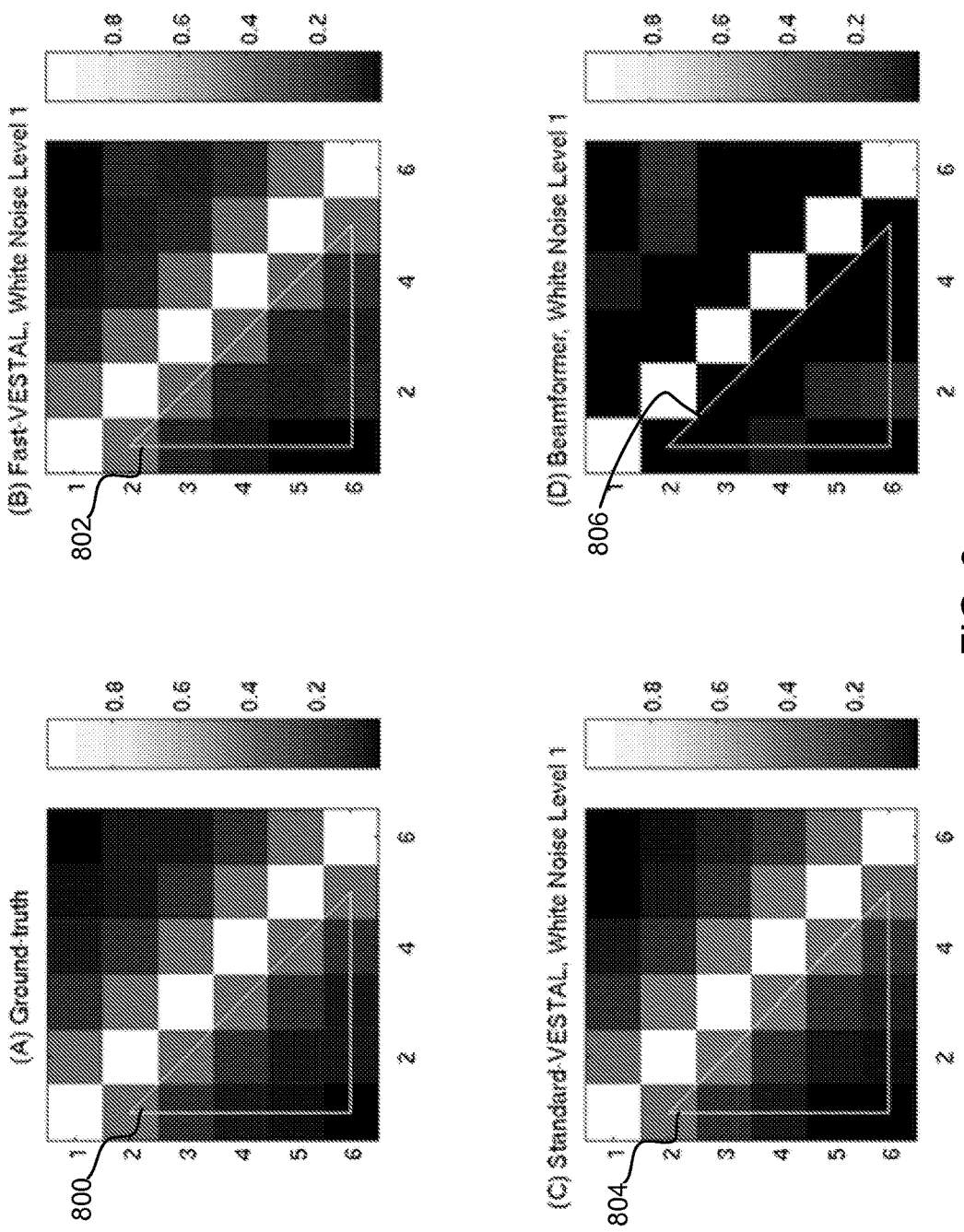
FIG. 8 shows a cross correlation coefficient matrix for the 6 simulated source. (A): using ground-truth source time-courses; (B): using time-courses reconstructed by Fast-VESTAL at white-noise Level-1; (C): by Standard-VESTAL; (D): by beamformer. The coefficients under the lower-left white triangles 800, 802, 804 and 806 were used to calculate the inter-source cross correlation (ICC) and their percent variance explained to the ground-truth values, as listed in Table 1.

Also calculated were the PVE values (relative to the ground-truth) for the ICC measures under the white triangles 800, 802, 804, 806 in the cross-correlation matrices in FIG. 8 from the three source modeling techniques, which are shown in the middle-left panel of Table 1. As highlighted in bold, the PVE values for the ICC from Fast-VESTAL are above 98%, markedly higher than those from beamformer,

| Noise Levels | Fast VESTAL | Std VESTAL | Beamformer | Fast VESTAL | Std VESTAL | Beamformer |
| --- | --- | --- | --- | --- | --- | --- |
| | Source Time-course PVE (%), White Noise | | | Source Time-courses PVE (%), Brain Noise | | |
| Level-0 | 100.0-100.0 | 100.0-100.0 | 77.5-89.9 | — | — | — |
| Level-1 | 99.6-99.9 | 99.0-99.8 | 77.2-89.5 | 97.7-99.2 | 95.7-99.4 | 60.0-91.6 |
| Level-2 | 96.9-98.9 | 86.8-95.7 | 74.2-87.3 | 87.4-96.2 | 70.5-90.5 | 58.7-78.3 |
| Level-3 | 83.9-94.5 | 78.1-93.3 | 60.7-77.9 | 43.6-87.3 | 33.5-85.7 | 9.3-59.0 |
| | ICC PVE (%), White Noise | | | ICC PVE (%), Brain Noise | | |
| Level-0 | 100.0 | 100.0 | 8.7 | — | — | — |
| Level-1 | 99.7 | 99.5 | 8.7 | 99.5 | 92.4 | 18.4 |
| Level-2 | 99.7 | 93.5 | 8.9 | 96.9 | 71.1 | 18.2 |
| Level-3 | 98.4 | 92.4 | 13.2 | 60.2 | 45.1 | 15.5 |
| | Orientation error (deg), White Noise | | | Orientation error (deg), Brain Noise | | |
| Level-0 | 0.0-0.0 | 0.0-0.0 | 0.2-8.0 | — | — | — |
| Level-1 | 0.1-0.5 | 0.2-0.7 | 0.3-8.1 | 0.1-1.5 | 0.4-2.1 | 0.7-13.6 |
| Level-2 | 0.2-2.0 | 0.3-3.1 | 0.6-8.2 | 0.6-6.5 | 0.6-8.5 | 0.9-20.4 |
| Level-3 | 0.7-13.1 | 1.2-12.5 | 0.9-16.8 | 0.7-18.5 | 1.0-21.5 | 1.4-24.4 |

Table 1 lists the percent variance explained (PVE) in the reconstructed source time-courses relative to the ground-truth source time-courses by Fast-VESTAL, Standard-VESTAL, and beamformer. For each source, the PVE of source time-courses was defined as:

$$PVE_q = \left(1 - \frac{\sum_i (q_i(t) - \hat{q}_i(t))^2}{\sum_i q_i(t)^2}\right) \times 100\%,$$

where the q(t) and q̂(t) are the ground-truth and reconstructed source time-courses, respectively. The upper-left panel of the table lists the range of PVE for the 6 sources at different white-noise levels. The PVE values from Fast-VESTAL solutions were in the upper 90s % to 100% range for white-noise Levels 0-2; and between 83.9% to 94.5% for the Level-3 condition where the SNR was substantially less than one. The PVE values from the Standard-VESTAL solution were quite high as well, but less than those from the Fast-VESTAL. In contrast, the PVE from the beamformer-reconstructed sources were markedly lower, even at the noiseless (Level-0) condition, indicating substantial distortions in the reconstructed source time-courses.

Inter-Source Cross Correlation Exam:

Another important measure of reconstructed source time-courses is the inter-source cross correlation (ICC). The ICC assessed if the reconstructed source time-courses preserve the inter-relationship of the time-courses among different sources. FIG. 8(A) plots the cross-correlation matrix of the 6 ground-truth source time-courses. The diagonal elements are all one since each source 100% correlated with itself.

which are 13.2% or lower. The performance of Standard-VESTAL was also good with PVE for ICC all above 92%, yet slightly inferior to those of the Fast-VESTAL.

Statistical Maps and Source Location Reconstruction for Signals with White Noise:

The exemplary approach can be implemented to assess the statistical significance of the Fast-VESTAL results and use it to construct statistical maps of the neuronal activities. For the simulation data with different white-noise levels, F-test assesses the statistical significance in variances between post-stimulus 700 ms interval over the pre-stimulus 300 ms interval for each grid node. The F-value maps from the Fast-VESTAL, Standard-VESTAL, and beamformer are shown in the 4-upper panels of FIG. 9 for white-noise Levels 0-3. The range of the F-values across different noise levels were orders of magnitudes different, due to different SNRs. To display the F-values in a comparable fashion, the threshold of the color scale was set to the F-value corresponding to corrected p-value of 0.01 (FDR), whereas the saturation value of the color scale was set to be $F_{saturation} = F_{threshold} + (F_{max} - F_{threshold}) \times 0.3$. Here, $F_{max}$ was the maximum F-value in the brain volume for a specific noise level condition.

For noise Level-0, the maps from Fast-VESTAL and Standard-VESTAL were virtually identical to the ground-truth locations of the 6 simulated sources (FIG. 5B). The statistical maps from beamformer solution revealed the 6 local maxima that matched the ground-truth locations. However, the spatial extent of the beamformer local maxima is markedly larger than those from the two VESTAL techniques, with above threshold F-values in wide-spread areas across the brain, suggesting potential signal leakage from the beamformer solution. Good source location reconstructions were also obtained from both Fast-VESTAL and Standard-VESTAL for white-noise Levels 1-3 as shown in FIG. 9(B)(C)(D), although some activities spread to the neighboring voxels for the highly noisy condition (i.e., Level-3). In contract, substantial signal leakage was observed in the beamformer solution for all three noise level conditions.

Monte-Carlo Analysis for the Efficacy Pre-Whitening and Objective Threshold for the Cut-Off of Noise Subspace The robustness of Fast-VESTAL was examined using correlated MEG brain noise collected from a healthy subject when he was watching a fixation point for over 2 hours in multiple 5-minute sessions. The brain-noise data were divided into a pool of over 6,100 artifact-free epochs (1000 ms duration). Then, Monte-Carlo analysis was performed, in which three conditions of brain noise were constructed that approximately matched the noise levels of the white-noise conditions based on Frobenius norms. The numbers of randomly selected epochs for trail-averaging in the brain-noise Level-1, 2, and 3 conditions were 125, 14, and 3, respectively.

Figure 10:
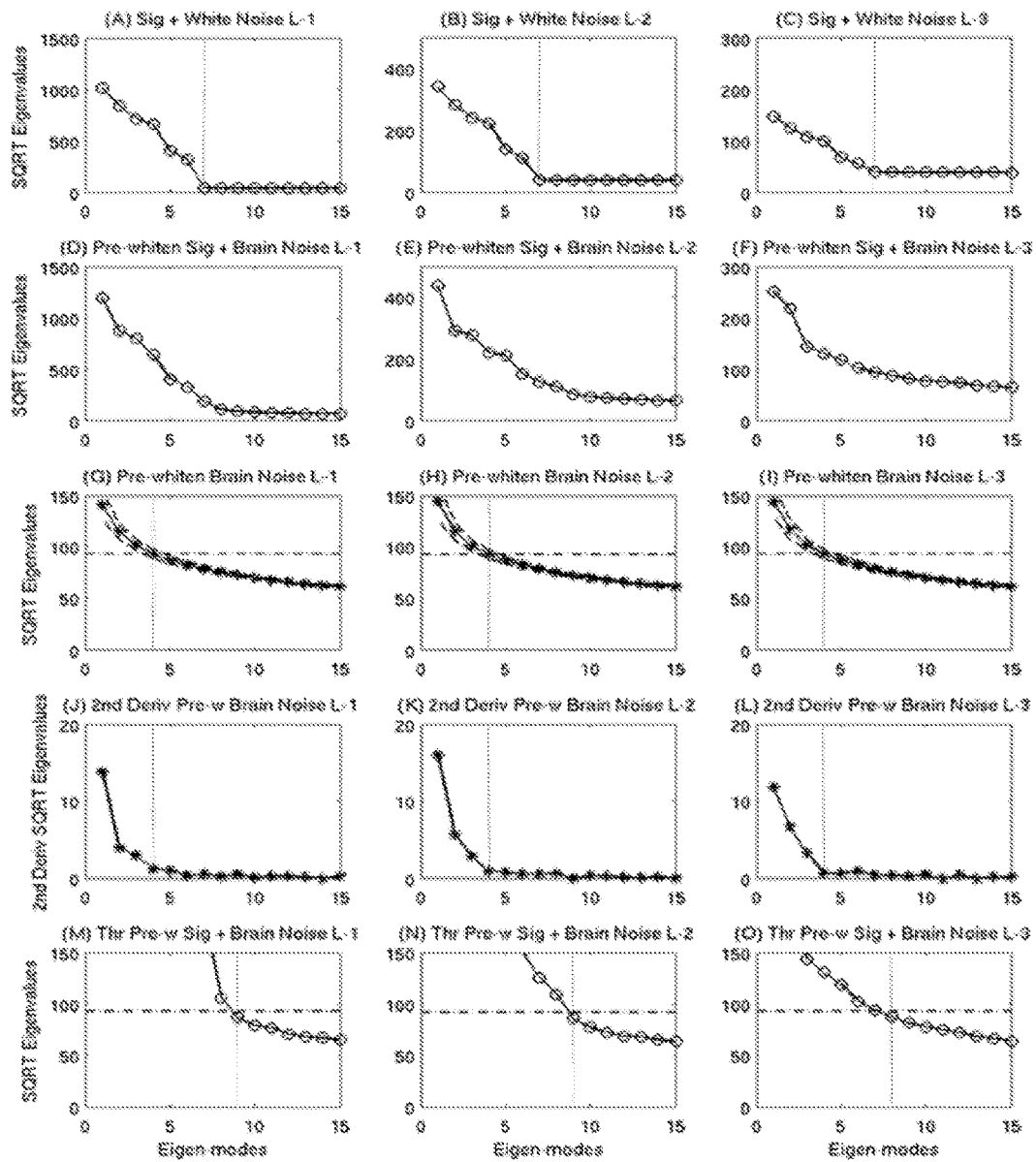
FIG. 10 shows objective thresholding in OPWM to separate noise subspace from signal subspace. Row 1: the square root (SQRT) plots of the eigenvalues in the sensor covariance matrices from simulated signal with white-noise Levels 1-3. Vertical dotted lines indicated the beginning of the noise subspace. Row 2: SQRT plots of the eigenvalues in pre-whitened sensor covariance matrices from simulated signal with brain-noise Levels 1-3. No clear distinctions were seen between noise and signal subspaces. Row 3: SQRT plots of eigenvalues in pre-whitened sensor covariance matrices for daughter brain-noise conditions from the Monte-Carlo analysis. The dash-dotted lines were the thresholds associated with the beginning eigenmode from noise subspace determined in Row 4. Row 4: second-order derivatives of the SQRT plots of eigenvalues in Row 3. Clear cutoffs of the noise and signal subspaces are seen as indicated by vertical dotted lines. Row 5: Application of the objective threshold to curves from Row 2.

One key issue for the signal with correlated brain noise is that the boundary between signal subspace and noise subspace is blurred, which makes determining the number of signal (dominant) spatial modes k in Eqs. (12)-(14) more challenging than for cases with white noise. In FIG. 10(A)(B)(C), the SQRT plots of the eigenvalues in the sensor covariance matrices from simulated signal (white-noise Levels 1-3) clearly showed different characteristics between the signal subspace (i.e., Spatial Modes 1-6), and the flat noise subspace. The vertical dotted lines mark the beginning of the noise subspace (i.e., number 7). However, there is no clear boundary between signal subspace and noise subspace for the conditions of simulated signal with different levels of real brain noise added as shown in FIG. 10(D)(E)(F). This is a common and difficult problem for analyzing MEG signals with real correlated brain noise.

To solve this problem, first examined was the efficacy of removing brain noise from the data for the entire 1000 ms epoch when we constructed the estimated (mother) brain-noise covariance matrix only using a portion of the interval. Here, we were only dealing with epochs with brain noise: no simulated signal was added in this test. First, we first performed 40 Monte-Carlo analyses to examine epochs for each brain-noise level condition. For example, for the brain-noise Level-1, we examine 40 sets of 1000 ms epochs, and within each set, we averaged 125 trials (i.e., 5,000 random epochs were involved). In each set, we performed pre-whitening to the whole 1000 ms epoch following Eqs. (23) and (24), by using only the first 300 ms to construct the mother noise covariance matrix. For brain-noise Level-1 condition with 125 trials, asterisks connected by solid line in FIG. 10(G) show the SQRT of the eigenvalues of the daughter pre-whitened brain-noise covariance matrices (DP-WBNCM) from the entire 1000 ms interval. The two dashed line indicate the range of one standard deviation across the 40 sets of Monte-Carlo analysis. Very similar results were seen for brain-noise condition Level-2 with 14 trials (FIG. 10(H)), and for Level-3 with 3 trials (FIG. 10(I)).

The important characteristic of the SQRT plots of the eigenvalues from the DPWBNCM for the entire 1000 interval was their second-order derivatives, plotted in FIG. 10(J). The leading eigenvalues were different from zero suggesting the pre-whitening step did not completely remove the correlated brain noise. However, a clear boundary was visible between the signal subspace (i.e. eigenmodes 1-3) indicating residual brain signal after pre-whitening, and noise subspace as marked by the vertical dotted line for the condition of brain-noise Level-1. Obvious distinctions between residual signal subspace and noise subspace were also observed for brain-noise Level-2 (FIG. 10(K)) and Level-3 (FIG. 10(L)), using the second-order derivative approach. Now, knowing the cutoff of the noise subspace (i.e., $4^{th}$ eigenmode), we can go back to FIG. 10(G)(H)(I) and identify the objective threshold of noise subspace in the actual SQRT of the eigenvalue plots, which is the value associated with the fourth eigenmode as indicated by the horizontal lines. The objective thresholds (horizontal lines) were virtually identical across all three brain-noise conditions. All the eigenmodes with their associated eigenvalue SQRTs above the lines belong to the signal subspace.

Finally, applied was objective thresholds to the exemplary simulated data that contained signals from the 6 simulated sources with different levels of brain noise added. For signal with brain-noise Level-1, FIG. 10(M) showed the same SQRT of the eigenvalues as in FIG. 10(D), but at a zoom-in scale. The horizontal line exhibited the same objective threshold obtained from the brain-noise Monte-Carlo analysis in FIG. 10(G). Eigenvalues below the threshold belong to the noise subspace, the beginning of which is designated by the dotted vertical line in FIG. 10(M) (i.e., $9^{th}$ eigenmode). The same threshold approach was applied to simulated signal with real brain-noise Levels 2 and 3. As indicated by the dotted lines in FIGS. 10(N) and 10(O), the noise subspace starts at the ninth and eighth eigenmodes for brain-noise Level-2 and 3, respectively.

Computer Simulation Results with Real Brain Noise, Correlated Sources, and Different SNRs The realistic brain noise was added to the simulated signal to challenge the performance of Fast-VESTAL. Following the pre-whitening step and objective threshold method described in the previous section, we reconstructed the source time-courses and location maps using Fast-VESTAL, Standard-VESTAL, and beamformer. FIG. 11(A) displays the MEG sensor waveforms containing simulated signals from 6 sources plus the real brain noise after 125 trial averages (Level 1 brain noise). The reconstructed source time-courses from Fast-VESTAL (FIG. 11(B)) matched the ground truth source time-courses well. Reconstructed source time-courses from Standard-VESTAL were reasonably good (FIG. 11(C)), but inferior to Fast-VESTAL. Obvious distortions were seen in the reconstructed source time-courses from beamformer (FIG. 11(D)). For Level-2 brain noise with 14 trials of averaging (sensor waveforms shown in FIG. 11(E)), reconstructed source time-courses from Fast-VESTAL (FIG. 11(F)) and Standard-VESTAL (FIG. 11(G)) again outperformed those from beamformer (FIG. 11(H)). For the simulated signal with high (i.e., Level-3) brain noise with only 3 trials of averaging, the signal in the post-stimulus interval is barely visible in the MEG sensor waveforms in FIG. 11(I), yet the reconstructed source time-courses from Fast-VESTAL (FIG. 11(J)) and Standard-VESTAL (FIG. 11(K)) still appeared to capture the main signature of the true source time-courses, although they were noisier than the other noise conditions. Distortion in the source time-courses was particularly marked from beamformer (FIG. 11(L)).

For all three conditions with real brain noise, the upper-right panel in Table 1 lists the PVE relative to the ground-truth source time-courses using the source time-courses that were reconstructed from Fast-VESTAL, Standard-VESTAL, and beamformer. All values are lower than the corresponding white-noise conditions, especially for the brain-noise Level-3. The Fast-VESTAL showed the highest PVE, followed by Standard-VESTAL, and beamformer. Likewise, the inter-source correlation PVE values for the signal with three levels of real brain noise were listed the middle-right panel in Table 1. FAST-VESTAL showed the highest ICC PVE, with values above 95% for Levels 1 and 3, but only 60.2% for Level-3. This contrasted with the moderate ICC PVE values from Standard-VESTAL and the notably low values from beamformer.

Source Orientation Reconstruction

The bottom panel of Table 1 lists the errors in source orientation for each solution. Orientation errors were calculated for the center voxel with the strongest activities within 10 mm from the true source locations. The source-orientation parameters were obtained accurately by Fast-VESTAL for the simulated data. For white and brain-noise Levels 0-2, the orientation errors were less than 10 degrees. The largest error in source orientation was 18.5 degrees for brain-noise Level-3 condition. Orientation errors from Standard-VESTAL and beamformer were also reasonably small, but somewhat larger than those from Fast-VESTAL.

Cutoff of the Singular Values in the Gain Matrix in Fast-VESTAL

Figure 12:
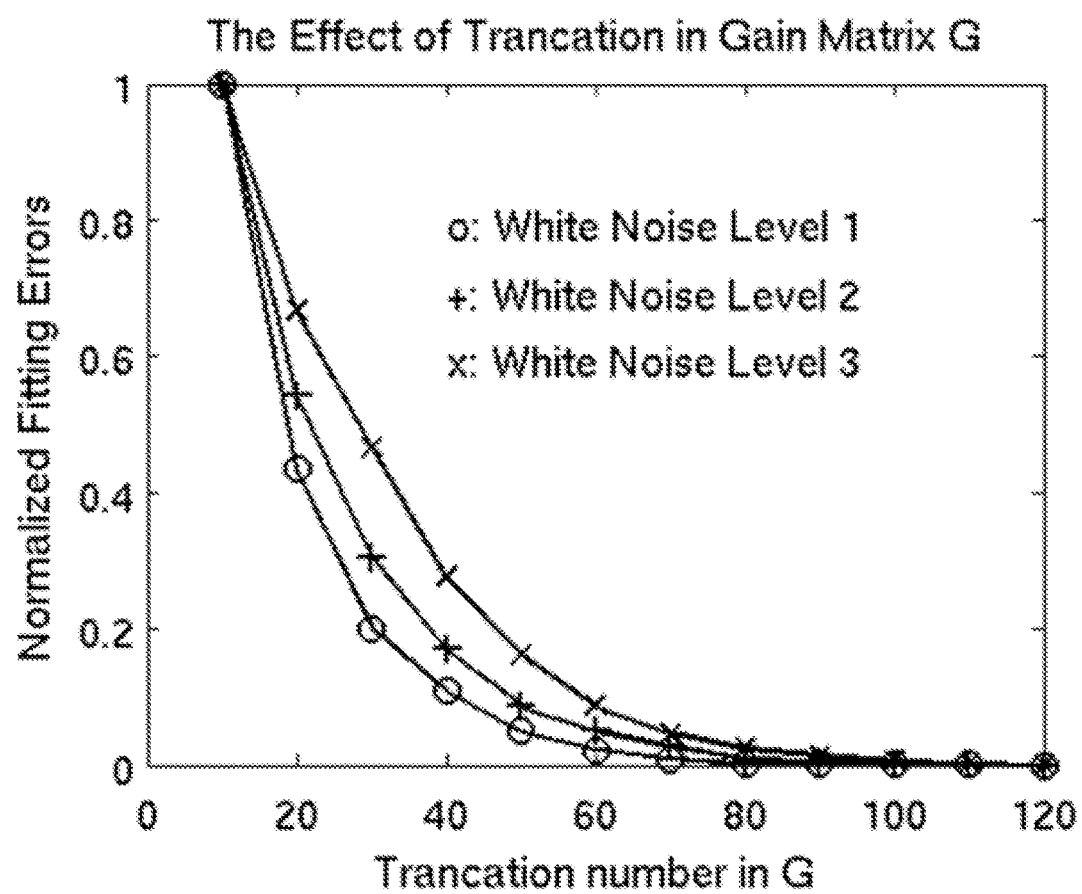
FIG. 12 shows normalized error of the Fast-VESTAL predicted MEG sensor waveforms over the ground truth, as a function of the singular value cut-off in the gain matrix. In all three conditions with different white-noise levels, the errors of prediction reach the saturation level ~80.

The number of dominant singular values in $S_G$ was set to 80 in Eq. (10) and all other smaller singular values in $S_G$ were set to be zero. FIG. 12 plots the normalized error of the Fast-VESTAL-predicted MEG sensor waveforms over the ground truth, as a function of the singular value cut-off in $S_G$. In all three conditions with different white-noise levels, the errors of prediction reached the saturation level ~80.

Human Median-Nerve Results for Fast-VESTAL and Beamformer

Figure 13A:
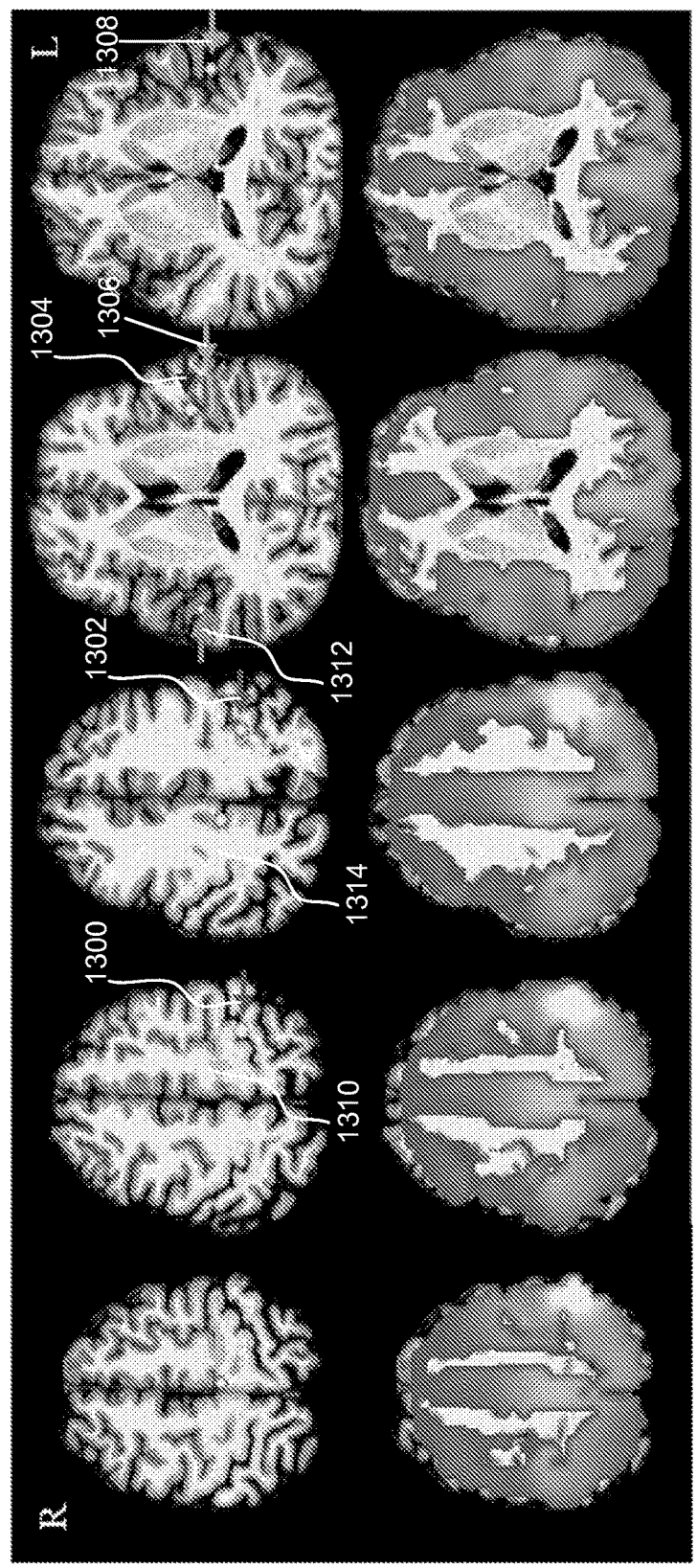
FIG. 13A shows, in the top row, F-value maps of axial MRI view for the locations of six sources obtained by Fast-VESTAL for right median nerve stimulation. The color scale for the F-value was the same as in FIG. 8. Red arrow 1300, 1302 for cSI; Blue arrow 1304 for cSII-a; Green arrow 1306, 1308 for cSII-b; Cyan arrow 1310 for cSMA; Magenta arrow 1312 for iSII; Yellow arrow 1314 for iSMA.
Figure 13B:
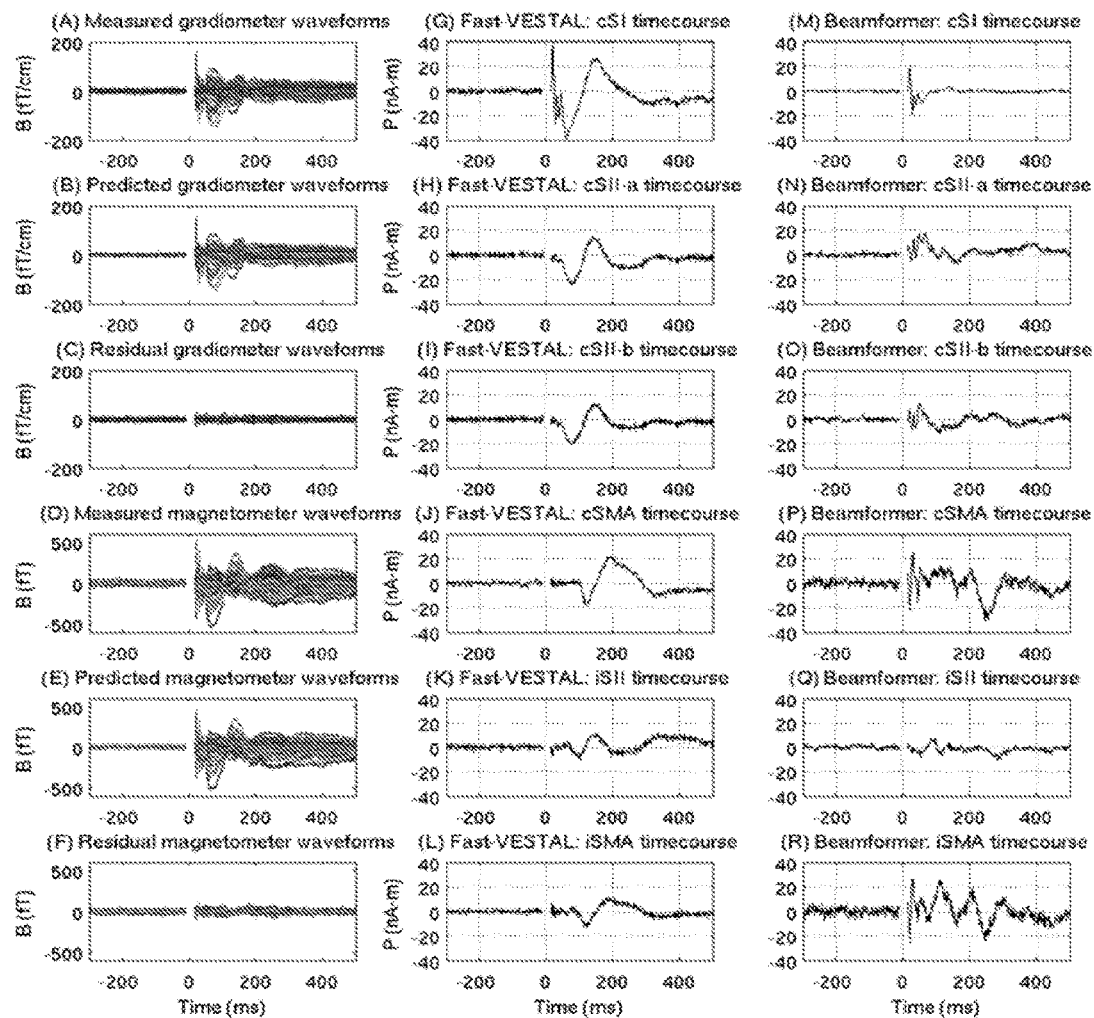
FIG. 13B shows, in the Left column, measured and predicted MEG sensor waveforms from Fast-VESTAL; in the Middle column, Fast-VESTAL source time-courses for the above sources; and in the Right column, source time-courses from beamformer.

Fast-VESTAL was applied to a data set containing MEG responses evoked by right median-nerve stimulation in a healthy subject. FIG. 13B (A)(D) show the measured sensor-waveforms of MEG responses for the −300 ms-500 ms duration evoked by the right median-nerve stimulation, with 204 gradiometers and 110 magnetometers superimposed, respectively. The −10 ms to 15 ms gap was removed from the analysis due to the large artifact from the electrical stimuli. The remaining −300 ms to −10 ms pre-stimulus interval was used to construct the estimated noise covariance matrix and to pre-whiten the response for the entire interval. To examine the efficacy of the pre-whitening step and identify the noise subspace, a five-minute session of brain-noise recording collected from the same subject, but on a different day, was divided into ~310 artifact-free epochs, each lasting 800 ms, with the first 300 ms used to estimate the mother brain-noise covariance matrix. The number of dominant spatial modes was selected using the same OPWM that we developed for the simulated signal with correlated brain noise.

Figure 9:
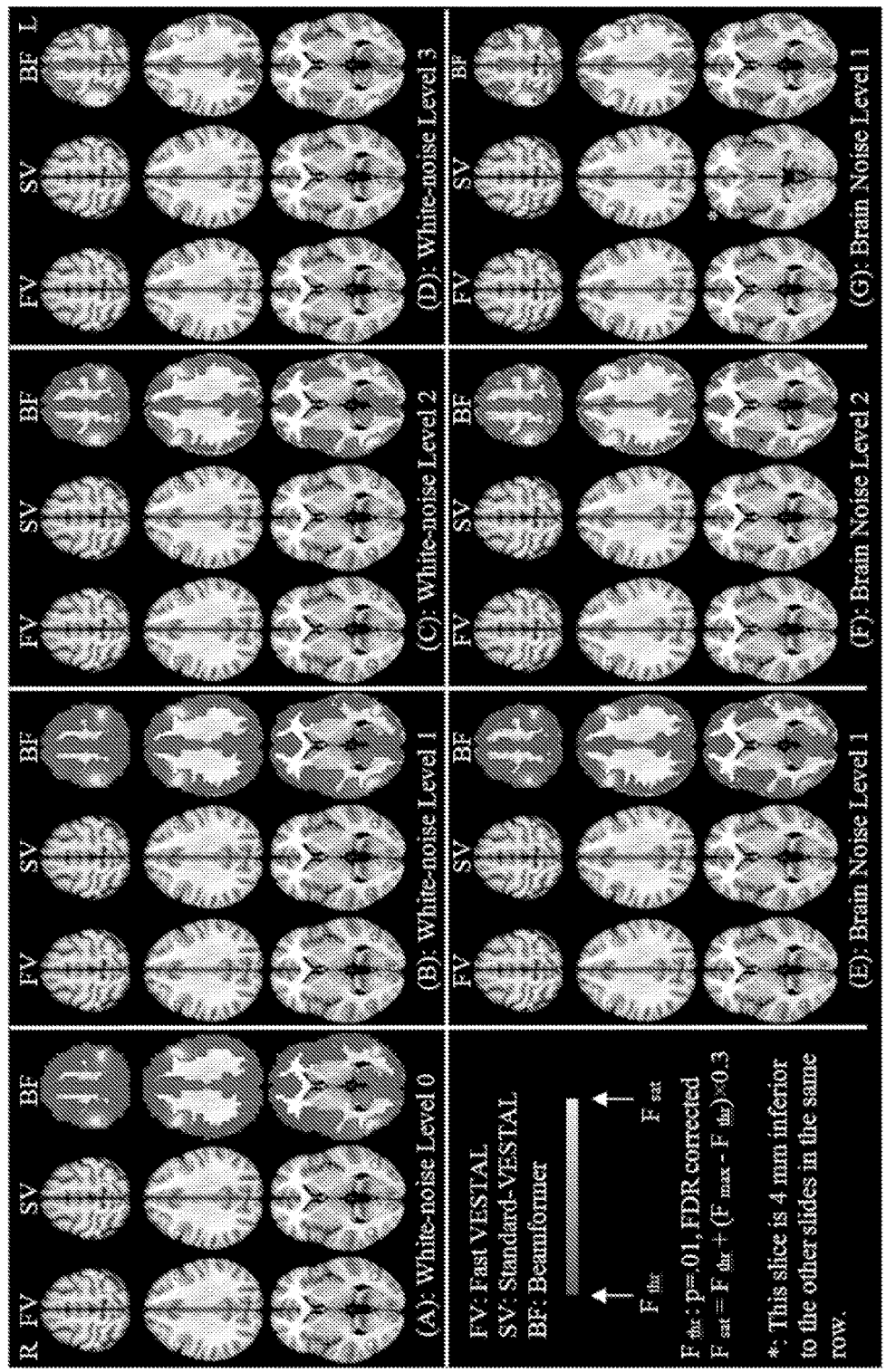
FIG. 9 shows F-value maps (post-stimulus over pre-stimulus) of source activity for the six simulated sources reconstructed from FV: Fast-VESTAL; SV: Standard-VESTAL; BF: beamformer. The upper four panels were for white-noise Level-0 (A); white-noise Level-1 (B); white-noise Level-2 (C); and white-noise Level-3 (D). The three lower panels were for brain-noise Level-1 (E) with 125 trial-averaging; brain-noise Level-2 (F) with 14 trial-averaging; and brain-noise Level-3 (G) with 3 trial-averaging.

The predicted MEG sensor waveforms in FIG. 13B (B) (E) from the Fast-VESTAL solution matched the measurement very well. FIG. 13B (C)(F) show that mainly noise remained in the residual waveforms (i.e., measured minus predicted). The upper panel of FIG. 13A shows the spatial maps significance sources, based on the F-tests of source time-courses in the post-stimulus interval versus the pre-stimulus baseline. Six sources were obtained by Fast-VESTAL for the responses evoked by the right median nerve stimuli: one in contralateral (left) primary somatosensory cortex (cSI), two in contralateral secondary somatosensory areas (cSII-a and cSII-b), one in contralateral supplementary motor area (cSMA), one in ipsilateral (right) secondary somatosensory area (iSII), and one in ipsilateral supplementary motor area (iSMA). The color scale in FIG. 13A was set in the same manner as for the F-test spatial maps in simulations (FIG. 9).

The plots in FIG. 13B (G)-(L) show the time-courses of the 6 sources from Fast-VESTAL. The cSI time-course showed sharp early-components that peaked at ~20 ms and ~30 ms with opposite polarities (FIG. 13B (G)). These sharp transient components were not observed in the time-courses of the other sources. Two slow components at ~60 ms and ~150 ms were also seen in the cSI time-courses. The time-courses of the two cSII sources (i.e., cSII-a and cSII-b) were very similar with peak latencies of the first and second components at ~75 ms and ~140 ms, respectively (FIG. 13B (H)(I)). The time-course of cSMA shows two slow components with peak latencies at ~125 ms and ~180 ms, respectively (FIG. 13B (J)). The amplitude of the iSII source was weaker than for cSII, with peak latencies at ~90 ms and ~150 ms (FIG. 13B (K)). The iSMA time-course showed similar peak latencies as those of cSMA, but with weaker amplitude (FIB. 9B (L)). Table 2 lists the cross-correlation coefficients among these 6 sources, which varied between 12% and 98%.

TABLE 2 shows Fast-VESTAL cross correlation coefficients among the time-courses from 6 sources evoked by median-nerve stimuli in post-stimulus interval.

|  | cSI | cSII-a | cSII-b | cSMA | iSII | iSMA |
| --- | --- | --- | --- | --- | --- | --- |
| cSI |  |  |  |  |  |  |
| cSII-a | 0.71 |  |  |  |  |  |
| cSII-b | 0.77 | 0.98 |  |  |  |  |
| cSMA | 0.25 | 0.32 | 0.18 |  |  |  |
| iSII | 0.12 | 0.65 | 0.61 | 0.60 |  |  |
| iSMA | 0.22 | 0.31 | 0.16 | 0.95 | 0.51 |  |

For comparison, we also performed beamformer analysis on the same data median-nerve responses with 200 trials. There is controversy surrounding whether the signal covariance matrix should be reconstructed using the averaged signal or the un-averaged trials. We performed analysis using both approaches and obtained virtually the same results. FIG. 13A presents the beamformer result using the approach with un-averaged trials. The upper panel of FIG. 13A (second row) displays the statistically significant sources, based on F-tests of source time-courses in the post-stimulus interval versus the pre-stimulus baseline. The sole local maximum in this statistical map was in the cSI area. No clearly distinguishable local maxima were observed in other brain regions such as cSII or iSII. As for the simulated cases, the beamformer solution exhibited wide spread signal leakage to other regions.

Out of curiosity, we plotted the beamformer source time-courses in FIG. 13B (M)-(R) of the same six areas that Fast-VESTAL showed strong activities. Since many of these areas did not show visible local maxima, we had to use the same locations obtained from the Fast-VESTAL solution as seeds for obtaining the beamformer source time-courses. The early and sharp components of the cSI time-course (FIG. 13B (M)) were similar to that obtained by Fast-VESTAL (FIG. 13B (G)), but the late slow components were missing in the beamformer solution. The remaining source time-courses from beamformer appear substantially different from those obtained from Fast-VESTAL. Many beamformer-derived source time-courses showed the strong early and sharp components that were absent in Fast-VESTAL, except for cSI source.

Whole-Brain Source Amplitude Imaging for Resting-State MEG Signals Using Fast-VESTAL Fast-VESTAL was used to obtain the source amplitude (RMS) images of human resting-state (eyes-closed) MEG signals from 41 healthy control subjects and from 41 sets of empty-room data. In each human and empty-room data set, the MEG sensor covariance matrix for the resting-state recording was calculated for four different frequency bands, namely in alpha (8-10 Hz), beta (15-30 Hz), gamma (30-100 Hz), and low frequency (1-7 Hz) bands, after artifact removal and noise reduction pre-processing steps (see the Methods Section). Fast-VESTAL source images were obtained using the sensor covariance matrix and then transformed from the subject's native coordinates to the MNI-152 atlas coordinates.

Figure 14:
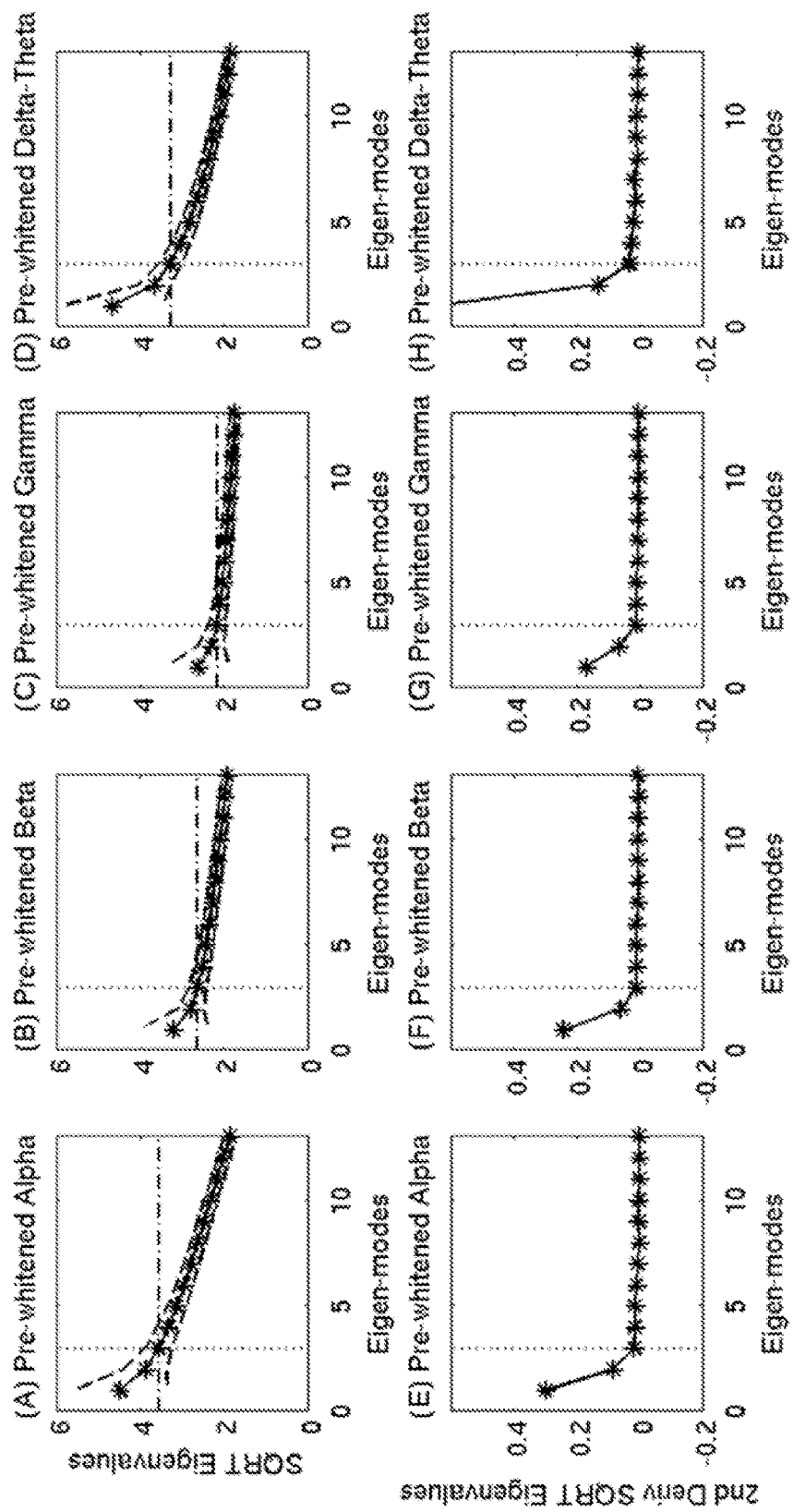
FIG. 14 shows OPWM separate noise and signal subspaces in empty room data. Top row: SQRT of eigenvalues from the daughter pre-whitened empty room covariance matrix (DPWERCM) for alpha (A), beta (B), gamma (C), and delta+theta (D) frequency bands. Bottom row: second-order derivatives of the SQRT of the eigenvalues. The vertical dotted lines show the beginning of the noise subspace, which are then used in the top row to determine the threshold of noise subspace (dash-dotted lines in top row).

FIG. 14 shows the process of using OPWM to separate the noise subspace from the signal subspace in the empty room data. After the pre-whitening step using the pre-whitening operator built from the mother noise covariance matrix of an extra empty-room data set (see Method), the SQRTs of the eigenvalues for the daughter pre-whitened empty room covariance matrix or DPWERCM were calculated from each of the 41 empty-room data sets. FIG. 14 (A)-(D) display the mean (solid lines) and standard deviations (dashed lines) for such SQRT of the eigenvalues of DPWERCM, across 41 empty-room sets, for alpha, beta, gamma, and delta plus theta bands, respectively. Like in the simulated case in FIG. 10, the second-order derivatives of the SQRTs of the eigenvalues from PWERCM show the clear cut of the noise-subspace at the eigenmode 3 for all bands. The thresholds for the SQRT of the eigenvalues for DPWERCM for the starts of the noise subspace were obtained from the horizontal dash-dotted lines in FIG. 14 (A)-(D) for all frequency bands. Such thresholds were used to determine the cutoffs of the signal subspaces (spatial modes) in the pre-whitened covariance matrices for 41 the empty-room data and the 41 human resting-state data in the Fast-VESTAL data analyses. For each of the 41 empty-room datasets, minimum 2 spatial modes were used in Fast-VESTAL analysis.

Figure 15:
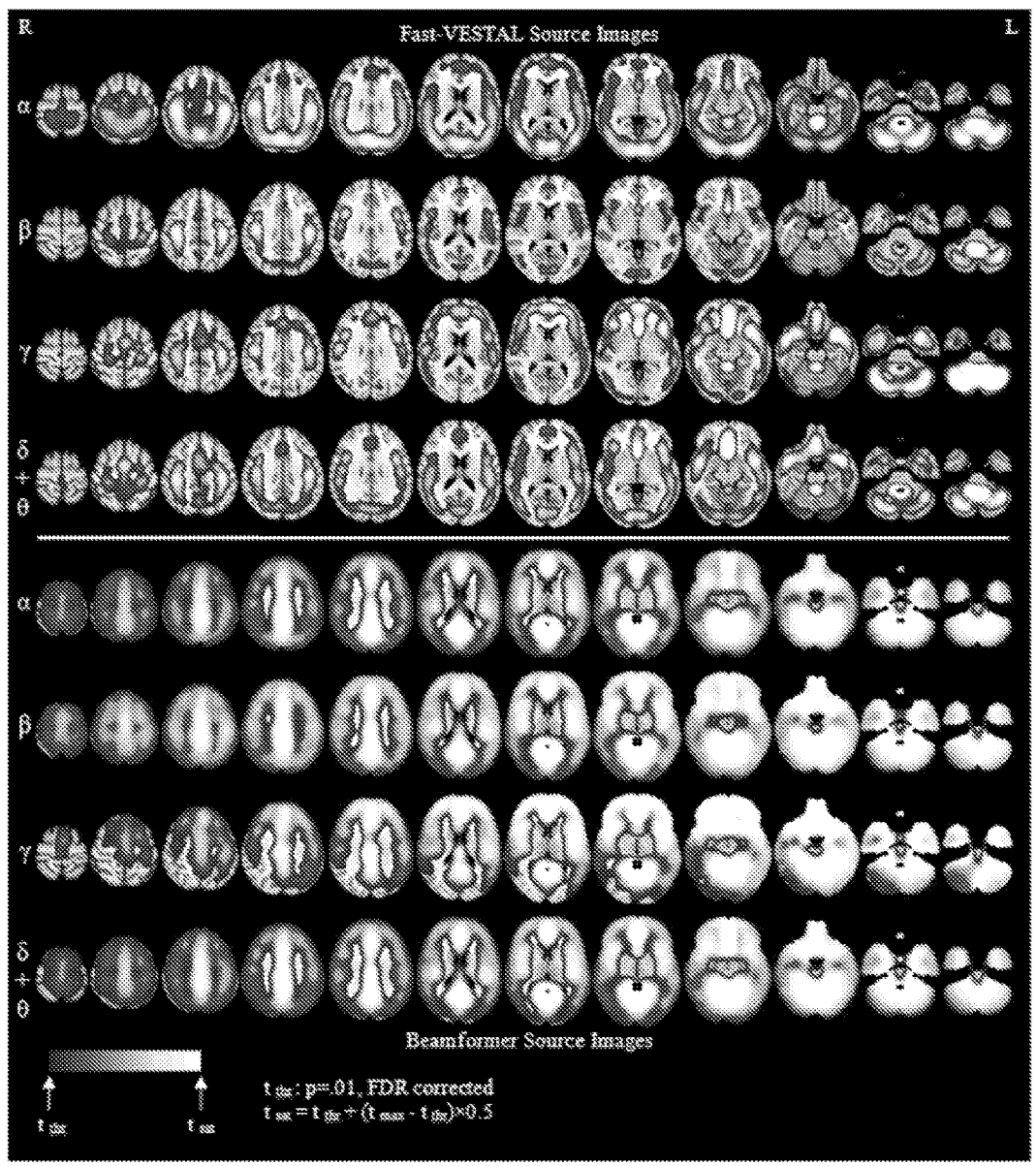
FIG. 15 shows, in Upper panels (Rows 1-4), whole brain t-value maps of the Fast-VESTAL source amplitude images for resting-state (eyes-closed) in alpha, beta, gamma, and delta+theta frequency bands; and in Lower panels (Rows 5-8), t-value maps of beamformer source amplitudes images for different frequency bands.

The t-value maps for the Fast-VESTAL solutions from human subjects versus the empty-room were shown in the 4 upper panels in the upper panel (top 4 rows) of FIG. 15 for different frequency bands in MNI-152 brain atlas coordinates, using the registration and smoothing steps described previously. The ranges of the t-values across bands were markedly different due to the different SNR levels from human rhythms (e.g., the SNRs in the alpha band were much larger than those in the gamma band). To effective plotted these t-values in a comparable fashion, the color scales in FIG. 15 were chosen in the following way: the threshold of the color scale was set to the t-value corresponding to corrected p-value of 0.01 (FDR), and the saturation value of the color scale was set as $t_{saturation} = t_{threshold} + (t_{max} - t_{threshold}) \times 0.5$. Here, $t_{max}$ was the maximum t-value in the brain volume for that specific noise level condition.

Alpha-Band Source Amplitude Images:

For the alpha band (first row in FIG. 15), the source amplitude images show strong cortical activity from the bilateral intracalcarine cortices, supracalcarine cortices, cuneal and precuneus, postcentral gyri, superior parietal lobules, and midline subcallosal cortices. Considerable alpha-band activity is also evident in the bilateral lateral-occipital cortices, angular gyri, and parietal operculum, and posterior aspects of superior and middle temporal gyri. Cerebella and brain-stem also show strong alpha activity. An interesting phenomenon is that frontal cortices do not show as strong alpha activity as the posterior portion of the brain.

Beta-Band Source Amplitude Images:

A different picture was seen for the MEG source images in the beta band (second row in FIG. 15). The bilateral postcentral gyri and midline subcallosal cortices show strong beta-band activity. However, beta-band activity is not as pronounced as alpha-band activity in bilateral intracalcarine and lateral-occipital cortices, supracalcarine cortices cuneous and precuneus, parietal operculum, and temporal lobes. Beta-band activity is significant in frontal areas (bilateral precentral gyri, frontal operculum, and anterior aspect of midline paracingulate and cingulate gyri). Strong beta-band activity is still seen in the brain-stem, but is not as pronounced in the cerebella.

Gamma-Band Source Amplitude Images:

Many interesting patterns of activity were seen in the gamma band (third row of FIG. 15). Strong activity was notable from midline paracingulate and cingulate gyri, bilateral superior and middle frontal sulci, frontal operculum and midline subcallosal cortices. In addition, bilateral precentral gyri, supramarginal gyri, parietal operculum, angular gyri, superior parietal lobules, middle temporal gyri, and midline precuneus also show substantial activity. Furthermore, bilateral anterior hippocampi, amygdala, and the temporal poles show strong gamma-band activity, which is markedly more prominent than the activity from the same regions in alpha or beta bands. Bilateral cerebella and brain-stem show strongest gamma-band activities among all bands, in the relative scale. Interestingly, the occipital lobe and posterior temporal lobe do not exhibit strong gamma-band activity.

Low Frequency-Band Source Amplitude Images:

The bottom row of FIG. 15 shows strong low-frequency activity (1-7 Hz) from bilateral intracalcarine cortices, supracalcarine cortices, midline paracingulate, frontal medial cortices, subcallosal cortices, and midline posterior cingulate. Considerable low-frequency activity is also seen in the bilateral Heschl's gyri, frontal operculum, precentral and poscentral gyri, angular gyri, parietal operculum, and middle temporal gyri. Bilateral anterior hippocampi, amygdala, temporal poles, and brain stem also show strong low-frequency activity.

Beamformer Source Amplitude Images:

The source images obtained by beamformer for the human resting-state data were substantially different from those by Fast-VESTAL. The bottom four rows in FIG. 15 show the beamformer source amplitude images as t-value maps between 41 healthy subjects versus 41 empty-room data sets. The different frequency bands were largely undifferentiated by beamformer maps. In all bands, almost all brain areas showed activity, except in subcortical regions and in superior portions of the cortex for gamma band activity. The regions that the exhibited the highest activity were the midline structures and the cerebellum.

Fast-VESTAL's Low Computational Costs

The computational cost of the conventional VESTAL is already relative low, e.g., as compared with many non-linear optimization approaches such as non-linear multiple-dipole modeling, and is substantially lower than that of Standard-VESTAL. In the above examples, the total number of time-samples was 1000, 777, and ~900,000 for the simulated data, human median-nerve, and human resting-state signals, respectively. Despite the high variability in the number of time-samples in these datasets, the total analysis time was typically in the range of tens of seconds to obtain source images on a source grid with ~7,000 nodes using Fast-VESTAL for each dataset. The computational cost of Fast-VESTAL is approximately proportional to the number dominance (signal-related) spatial modes k when solving Eq. (14), and is not directly related to the number of time samples as for the Standard-VESTAL. It takes about 10 seconds to solve the L1-minimum solution and obtain a volume of source images for each dominance (signal-related) spatial mode in Eq. (14). The time $\Delta_{L1}$ for solving one L1-minimum norm problem is almost the same for one spatial mode in Fast-VESTAL, one time-sample in Standard time-domain VESTAL, and one frequency-bin in Standard frequency-domain VESTAL. The total computational cost is $\mu k \times \Delta_{L1}$ Fast-VESTAL and $T \times \Delta_{L1}$ for Standard time-domain VESTAL. For the simulation cases with 6 spatial modes and 1000 time samples, the Fast-VESTAL was approximately 1000/6=166.7 time faster than Standard-VESTAL. All programs were developed in MATLAB and all analyses done on a Dell Precision 7500 Workstation with Dual Intel Xeon X5550 Processors (each with 8M Cache, 2.67 GHz, and 6.40 GT/s QPI) and with 24 GB System RAM. Although Fast-VESTAL is inherently a good candidate for parallel processing, no parallel processing was performed in the present exemplary implementations.

Discussion of the Exemplary Implementations

Discussion of Exemplary Results of Fast-VESTAL and Standard-VESTAL Versus Beamformer for Simulated Data In the present technology, a fast MEG source imaging technique based on a L1-minimum-norm solution, namely Fast-VESTAL is disclosed. Using simulations, the performance of Fast-VESTAL was assessed by multiple criteria including its 1) ability to localize multiple correlated sources and faithfully recover source time-courses; 2) robustness to different SNR conditions (including SNR with negative dB levels); 3) accuracy in reconstructing MEG source images; and 4) its computational cost. In addition, we developed an objective pre-whitening method, OPWM, and used it in Fast-VESTAL to remove correlated brain noise.

The exemplary results demonstrated that Fast-VESTAL accurately localized multiple sources in both white-noise and real brain-noise conditions, even under poor SNR situations (FIG. 9). In addition, the source orientation errors of the Fast-VESTAL solution were small. As the sensor noise levels increased, the orientation errors of Fast-VESTAL also increased, but for all simulated sources and SNR conditions the orientation errors were <14 and <19 degrees in the white-noise and real brain-noise conditions, respectively (Table 1). Standard-VESTAL performed similarly, but slightly inferior to Fast-VESTAL in terms of obtaining source locations and orientations for white and real brain-noise conditions. In contrast, although the beamformer was able to adequately obtain the source location and orientation, the widths of the local minima were substantially wider than those from Fast- or Standard-VESTAL. Notably, we did not intentionally choose highly simulated sources with 90%-100% correlations that VESTAL methods, but not beamformer, could localize. Nevertheless, one problem in all spatial maps from the beamformer solution was the serious signal leakage to regions where no signals should exist.

Figure 7:
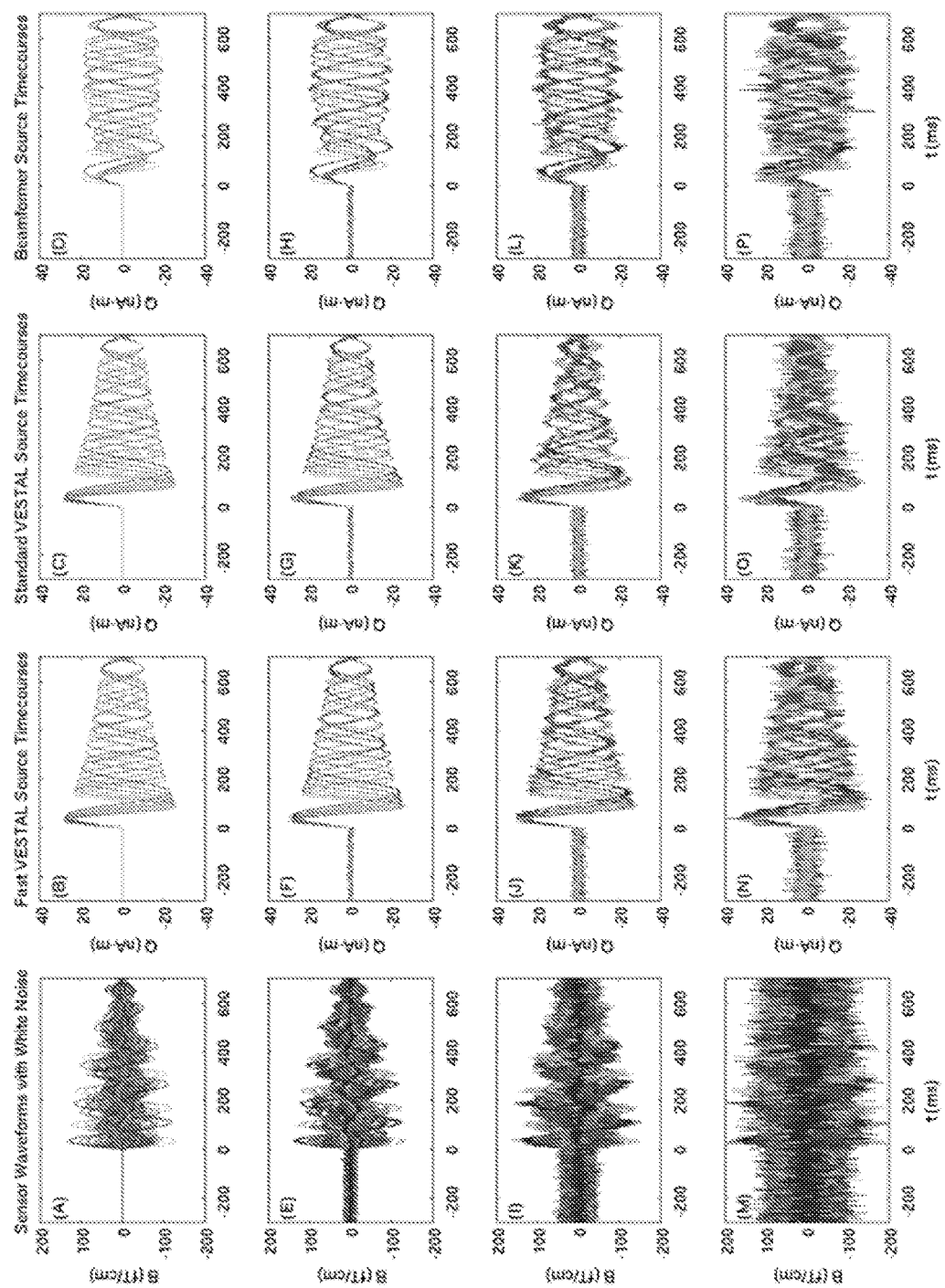
FIG. 7 shows simulated MEG sensor waveforms added white noise (first column) and source time-courses reconstructed from Fast-VESTAL (second column), Standard-VESTAL (third column), and beamformer (fourth column). Each row displays the data for different white-noise levels. Row 1: white-noise Level-0 (post-stimulus SNR=$2.23 \times 10^6$ or 126.9 dB); Row 2: white-noise Level-1 with post-stimulus SNR=4.46 or 12.90 dB; Row 3: white-noise Level-2 with post-stimulus SNR=1.48 or 3.45 dB; and Row 4: white-noise Level-3 with post-stimulus SNR=0.64 or −3.95 dB.
Figure 11:
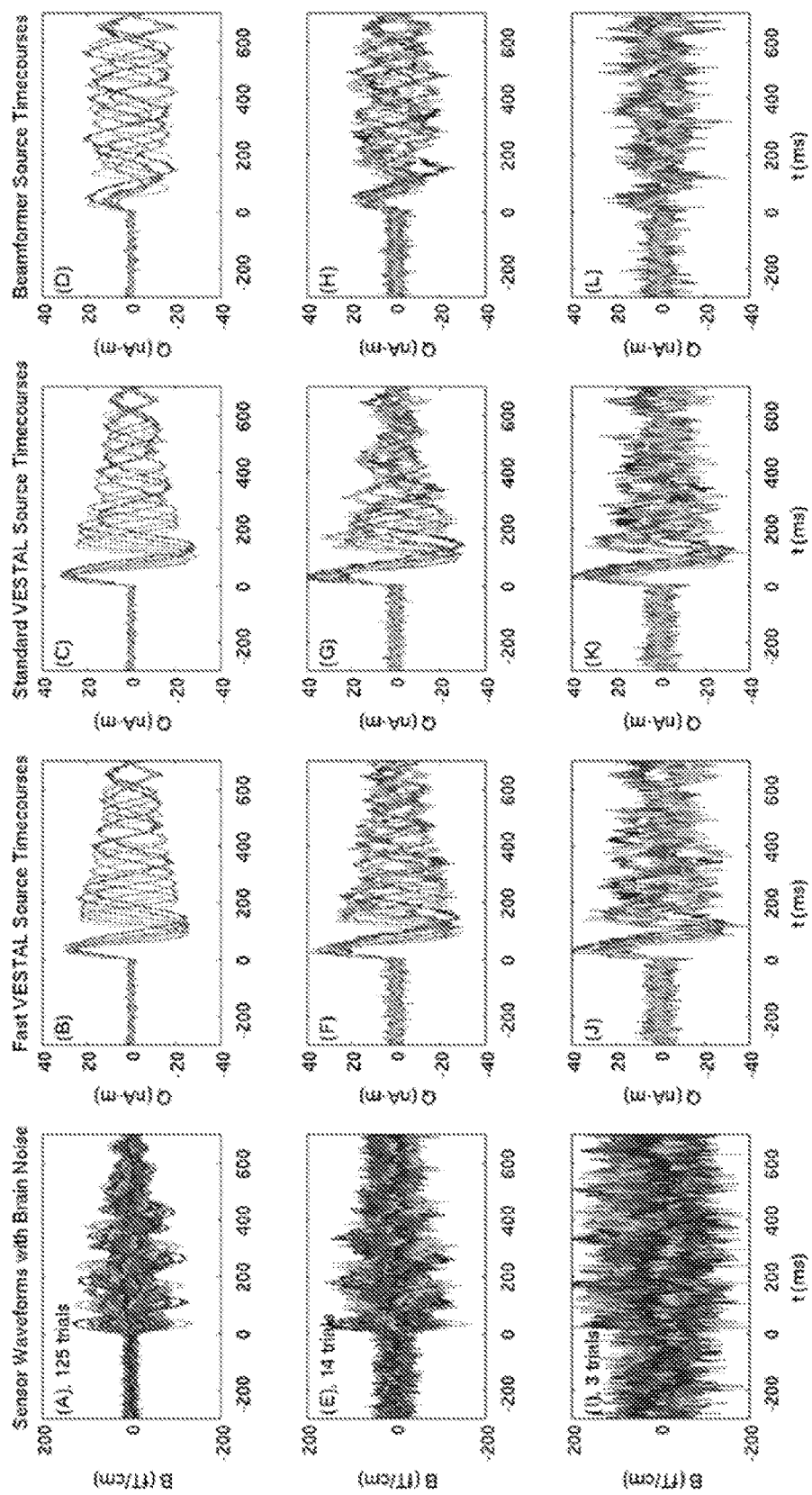
FIG. 11 shows simulated MEG sensor waveforms with different levels of real brain noise and the reconstructed source time-courses. Column 1: MEG sensor waveforms with brain-noise Levels 1-3. The associated number of trials for averaging was 125 (Level-1), 14 (Level-2), and 3 (Level-3), respectively. Column 2: reconstructed source time-courses from Fast-VESTAL. Column 3: from Standard-VESTAL. Column 4: from beamformer.

For example, one main advantage of Fast-VESTAL and Standard-VESTAL over beamformer has been the VESTAL algorithms' robustness for accurately obtaining correlated source time-courses, even at poor SNR levels and with real brain noise (FIGS. 7 and 11). Quantitative assessments (FIG. 8 and middle panels of Table 1) supported this feature with Fast- and Standard-VESTAL demonstrating PVE values for the ICC over 90% in most of the cases, whereas those values from beamformer were extremely low. We believe that the reason for Fast- and Standard-VESTAL's very good performance in obtaining source time-courses and maintaining high ICC is that no temporal constraints are imposed on the solutions. This is not the case in beamformer techniques, which assume that source time-courses are uncorrelated, and independent component analysis, which assumes that the source time-courses are statistically independent.

For example, another strength of Fast-VESTAL is its substantial improvement on computational speed over the Standard-VESTAL technique. In fact, the computational cost of Fast-VESTAL is basically independent of the time samples in the data, but instead proportional to the number of spatial modes in the sensor-spatial-profile matrix or sensor-covariance matrix, which usually takes tens of seconds or less. In contrast, the analysis time of Standard-VESTAL is proportional to the number of time-samples time-domain MEG data or frequency bins in frequency domain MEG data. The time for solving one L1-minimum norm problem is almost the same for one spatial mode in Fast-VESTAL, one time-sample in time-domain Standard-VESTAL, and one frequency-bin in frequency-domain Standard-VESTAL. Consequently, it took tens of seconds for Fast-VESTAL to obtain high-resolution MEG source images when processing datasets containing ~100-1000 (evoked MEG response) to ~100,000 (spontaneous MEG data) time samples. The processing time using Standard-VESTAL can be orders of magnitude longer.

The exemplary step of using temporal projection Eq. (10) in Fast-VESTAL is similar to the temporal dimension reduction in the Multiple Sparse Priors (MSP) method. Both approaches adopted the temporal projection and used sensor covariance matrix for dimension reduction. One difference is that Fast-VESTAL explicitly obtains the minimum L1-norm solution for dominate spatial modes in the sensor waveforms after the temporal projection using Eq. (10), whereas MSP performs both temporal and spatial projections and seeks the hyperparameters using the iterative expected maximization (EM) approach. A unique feature of Fast-VESTAL is that the process of obtaining the minimum L1-norm solution for dominate spatial modes is 1) guaranteed to converge and 2) non-iterative, without the need for controlling the converging process/criteria. Another unique feature of Fast-VESTAL is that we explicitly provide an inverse operator Eq. (18) based on the solution to faithfully recover the source time-courses with the same temporal resolution as the original sampling rate (e.g., in millisecond) even under extremely poor SNR conditions. It is also important to note that dimension reduction using Eq. (10) is not limited to the minimum L1 norm solution. In fact, minimum L2-norm can also be used to solve Eq. (10) if a widely distributed non-sparse solution is desired.

Objective Pre-Whitening Method for Removing Correlated Brain Noise

In the present technology, disclosed is an objective approach (i.e., OPWM) to effectively remove correlated brain noise (FIG. 6). OPWM provided 1) an objective way to measure the efficacy of the pre-whitening step, when the estimated correlated noise matrix was constructed using incomplete or non-real time information; 2) an additional procedure to further remove residual correlated noise when pre-whitening step is not completely successful, which was based on the plots of SQRT of eigenvalues of the daughter pre-whitening correlated noise covariance matrices; and 3) an objective way to identify noise subspace in the pre-whitened signal covariance matrix. A unique feature of OPWM is that it uses the second-order derivatives of the SQRT of the eigenvalues from the daughter pre-whitened noise covariance matrices. We discovered this feature based on the fact that in cases of pure white noise, the SQRT of the eigenvalues from noise subspace should be exactly zero. In correlated brain-noise cases, we found the second-order derivatives of the SQRT of the eigenvalues from the daughter pre-whitened noise covariance matrices is an effective way to differentiate noise subspace from residual signal subspace after pre-whitening. OPWM was applied extensively in the present exemplary implementations to remove correlated brain noise before the MEG signals were processed by Fast-VESTAL, Standard-VESTAL, and beamformer. The high similarity of the results from these three inverse source imaging methods for white-noise and brain-noise conditions underscores the good performance of OPWN (FIG. 7 versus FIG. 11; upper panels versus lower panels in FIG. 9; and left versus right panels in Table). We believe that the OPWM approach for removing correlated noise from the data is not inherently limited to Fast-VESTAL or MEG signal processing, but rather could be applied to any time-series analysis.

Median-Nerve Response

The application of Fast-VESTAL to the median-nerve MEG response of a single subject demonstrated the strength of this method in localizing multiple sources in human brain responses that are highly correlated. The cSI source from primary somatosensory cortex and its time-course, which exhibited initial sharp transient components at 20 and 30 ms followed by slow later components, are consistent with the known neurophysiology of the somatosensory system and previous studies. Since a relatively large time-window of 15 to 500 ms post-stimulus interval was used in this analysis, the cluster of cSI sources from Fast-VESTAL covered Brodmann areas (BA) 1, 2, and 3b (FIG. 13), which are all part of the hand representation of the primary somatosensory cortex and are highly contiguous in space. The cluster did not further differentiate the sub-regions of the cSI cortex (e.g., BA 3b from BA 1 and 2) as they do in conventional VESTAL analysis using individual time samples from a much shorter post-stimulus interval. Likewise the cSI time course shown in FIG. 13B (A) actually represented the combined activities from BA 3b, 1, and 2, namely, the early transient 20 ms and 30 ms activities from BA 3b plus the later ~60 ms and ~150 ms activities from BA 1 and 2. Responses from these sub-regions within SI were originally revealed using the Standard-VESTAL algorithm when analyzing individual time samples in a much shorter post-stimulus interval. In fact, we applied Fast-VESTAL to the analysis of a shorter period (i.e., 15-150 ms) and indeed observed two sub-clusters within cSI cortex, one in BA 3b and another in BA 1 and 2, with the time-course of the BA 3b sub-cluster showing strong transient 20 ms and 30 ms activity, and the BA 1 and 2 sub-clusters showing later ~60 ms and ~150 ms activities (figure not shown).

The contralateral and ipsilateral SII and SMA responses obtained from Fast-VESTAL (FIG. 13) also agreed well with previous findings. It was notable that there were two sources in the cSII region, one slightly more posterior (cSII-b, green arrow 1306, 1308) than the other (cSII-a, blue arrow 1304). The cSII-b source is also calles to ventral parietal cortex by others. The source time-courses obtained from Fast-VESTAL further revealed that these 6 sources were inter-correlated with correlation coefficients ranging from 10% to 98%. Altogether, these findings demonstrate Fast-VESTAL's ability to localize highly-correlated sources and resolve source time-courses, which is vital for a more complete understanding of the neurophysiology of the somatosensory system. In addition, the cSI source preceded the other sources in contralateral and ipsilateral hemispheres (FIG. 9A). Activity in cSIIs and cSMA of the contralateral hemisphere was earlier than those from corresponding areas in the ipsilateral hemisphere (i.e., iSII and iSMA). In addition, the time-courses of sources in the regions of the same functional type correlated more strongly than those that were functionally different (Table 2). For example, correlations between cSII-a and cSII-b (98%), cSII-a and iSII (65%), cSII-b and iSII (61%), and cSMA and iSMA (95%) were markedly higher than for cSI and iSII (12%) or cSII-a and cSMA (32%). An exception was the high correlation of cSI with cSII-a and cSII-b, which may be indicative of the strong functional connectivity of these two areas. These findings are highly consistent with the known neurophysiology of the somatosensory system.

In contrast, the beamformer solution was only able to find one obvious local maximum in the cSI (FIG. 13A, second row). The absence of the other sources that are known to exist was striking, and underscores the beamformer's difficulty in source detection under the conditions examined in present exemplary implementations. In published studies that used beamformer for analyzing median nerve responses, cSII, iSII, and other non-primary somatosensory sources were not reported. We believe this was due to the high inter-source cross correlations, which substantially violate the basic beamformer assumption that the sources must be uncorrelated. An exemplary explanation was supported by a close analysis of the cross correlations in Table 2 in which 8 out of the 15 cross correlation coefficients from Fast-VESTAL are above 50%. Furthermore, the early transient activity at 20-30 ms post-stimulus from the beamformer source time-courses (location seeded by Fast-VESTAL solutions) in cSII-a (FIG. 13B (M), cSII-b (FIG. 13B (N)), cSMA (FIG. 13B (P)), and iSMA (FIG. 13B (R)) was inconsistent with known neurophysiology of the somatosensory system owing to lack of direct thalamo-cortical projections to these non-primary somatosensory areas.

For example, a previous study suggested that the use of un-averaged individual trials rather than trial-averaged responses to construct signal covariance matrix may improve the localization of correlated sources, assuming these correlated sources may attenuate their correlations in the un-averaged trials. However, we found no difference between these two approaches in the exemplary beamformer analyses of median nerve data. Failing to show improvement using the un-averaged trials approach in beamformer suggests that the neuronal sources evoked by median-nerve stimuli are actually highly time-locked to the electric stimuli, such that beamformer will have problems localizing the correlated time-locked sources.

Source Amplitude Images of Human Resting-State Activity

The present exemplary implementations also assessed the performance of Fast-VESTAL relative to the beamformer in reconstructing resting-state MEG source amplitude images for each standard frequency band. This is the first comprehensive MEG/EEG source amplitude (power) imaging study for resting-state signal that covers the entire brain for multiple frequency bands. The MEG source-amplitude imaging method (or the square-root of the source power images) in the present exemplary implementations for the human resting-state rhythms is different from the MEG source covariance/functional connectivity source analysis. Here, we assessed how strong the neuronal sources were for different frequency bands, whereas the MEG source covariance/functional connectivity source analysis examines the similarity of the shapes of the source time-courses. Although the source-amplitude images are intrinsically different from the functional connectivity images, we do notice a high degree of similarity between Fast-VESTAL source-amplitude images and the most recent functional connectivity images. For example, the use of variance information (i.e. data that have not been variance normalized) in source-space projected Hilbert envelope time series yields important spatial information. They showed that employing the variance information in functional connectivity analyses improves the spatial delineation of network nodes. Additional analyses are needed to explore the similar findings across the two apparently different approaches (i.e., source-amplitude versus functional-connectivity images using variance information).

Resting-state alpha-band activity detected by EEG and MEG is known to be strong in the posterior half of the head (occipital, parietal, and posterior temporal regions), but may extend into the central areas in regions that generate the rolandic mu rhythm. The exemplary results obtained from Fast-VESTAL for the alpha-band were highly consistent with this neurophysiology. The present technology builds upon this knowledge by providing a more refined analysis of the generators of human alpha-band activity. For example within the occipital lobe, activity from intracalcarine, supracalcarine, and lateral-occipital cortices was clearly distinguishable in the Fast-VESTAL source images (FIG. 15). Likewise, it has not been clear whether the alpha-band activities in the central sulcus area (i.e., the rolandic mu rhythm) are mainly from the postcentral gyrus (primary somatosensory cortex), the precentral gyrus (primary motor cortex), or both. The Fast-VESTAL source images in the alpha band showed that although alpha activity extended to the precentral gyrus, the dominant activity was clearly from the postcentral gyrus, more specifically from the hand representation area of the somatosensory cortex.

The exemplary Fast-VESTAL source-amplitude images for the generation of the beta-band MEG signals were also highly consistent with previous EEG and MEG findings. Beta-band activity from the pre- and postcentral gyri are part of the rolandic mu rhythm. The Fast-VESTAL source images further showed that the postcentral gyri beta-band (mu) activity is mainly from the hand representation area of the somatosensory cortex.

The exemplary gamma-band source amplitude images from Fast-VESTAL also clearly showed larger involvement of frontal generators, different from those previously observed in alpha or beta bands (FIG. 15). Interestingly, gamma-band activity was also found in the anterior hippocampi, the amygdala, and the temporal pole. These results suggest that MEG resting-state gamma-band signal may be useful for studying memory and emotion processing. Fast-VESTAL-based MEG source amplitude images were also derived for low-frequency bands: delta (1-4 Hz) and theta (4-7 Hz) bands. The locations of midline frontal activity in paracingulate gyrus, medial frontal cortices, and subcallosal cortices appear to be consistent with theta activity seen in EEG, even though most of EEG studies were task-activated (e.g., problem solving) and provided no specific information on source locations. Another interesting finding from the Fast-VESTAL result is the high degree of similarity between gamma band and delta-theta band for the inferior frontal and anterior temporal regions (FIG. 15). The exemplary analyzing of the functional connectivity of these regions across these frequency bands can be implemented.

The exemplary results of source amplitude resting-state images using Beamformer were markedly different from those employing Fast-VESTAL. Beamformer showed little spatial differentiation among the different frequency bands. Although the neurophysiology of the human somatosensory system has been well studied, an understanding of the source amplitude images for different frequency bands is limited. As such, the quality of the beamformer source amplitude images for resting-state data cannot be assessed with certainty, which may be a limitation of the present exemplary implementations. Additional information from techniques such as ECoG will be needed to address this issue.

The disclosed Fast-VESTAL MEG source imaging algorithm can obtain L1-minimum-norm solutions for the sensor-waveform covariance matrix. Exemplary computer simulations demonstrated that Fast-VESTAL localizes correlated sources and accurately reconstructs their source time-courses even at poor signal-SNR conditions. Also disclosed is an objective pre-whitening method (OPWM) that can be used in implementations with Fast-VESTAL to objectively remove correlated brain noise. For example, the application of Fast-VESTAL to human MEG median-nerve responses in the described exemplary implementations further demonstrated its power in reconstructing source time-courses, e.g., which were highly consistent with known electrophysiology of the human somatosensory system. Furthermore, the exemplary Fast-VESTAL technique provided the first set of comprehensive MEG source-amplitude images that covered the entire brain in standard atlas coordinates for different frequency bands of resting-state signals. The disclosed Fast-VESTAL technology can be implemented such that it uses substantially low computational costs.

In one aspect, a method includes determining a covariance matrix based on sensor signal data in the time domain, the sensor signal data representing magnetic-field signals emitted by a brain of a subject and detected by a plurality of MEG sensors in a sensor array surrounding the brain, defining a source grid containing source locations within the brain that generate magnetic signals, the source locations having a particular resolution, in which a number of source locations is greater than a number of sensors in the sensor array, and generating a source value of signal power for each location in the source grid by fitting the selected sensor covariance matrix, in which the covariance matrix is time-independent based on time information of the sensor signal data.

In some aspects, for example, the disclosed covariance-domain MEG source imaging techniques can be combined with frequency-domain MEG source imaging techniques to further speed-up the data processing. For example, the relation between frequency-domain MEG source imaging and covariance-matrix-based high resolution MEG source imaging can be complimentary. For example, if the MEG signal of interest is within a pre-known frequency band (e.g., delta: 1-4 Hz, theta: 5-7 Hz, alpha: 8-13 Hz, beta: 15-30 Hz, and gamma: 30-100 Hz), the frequency-domain approach may be a powerful tool for MEG source imaging. On the other hand, if the MEG signal of interest is better represented in time-domain and/or the MEG signals could be distributed across multiple frequency bands, the covariance-matrix-based approach may be used.

Implementations of the subject matter and the functional operations described in this patent document and appendix can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and appendix contain many specifics, these should not be construed as limitations on the scope of any invention or of what may be claimed, but rather as descriptions of features that may be specific to particular embodiments of particular inventions. Certain features that are described in this patent document and appendix in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and appendix should not be understood as requiring such separation in all embodiments.

Only a few implementations and examples are described and other implementations, enhancements and variations can be made based on what is described and illustrated in this patent document and appendix.

What is claimed are techniques and structures as described and shown, including:

1. A method for high-resolution magnetoencephalography (MEG) source imaging, comprising:
   determining a covariance matrix based on sensor signal data in the time domain, the sensor signal data representing magnetic-field signals emitted by a brain of a subject and detected by a plurality of MEG sensors in a sensor array surrounding the brain;
   defining a source grid containing source locations within the brain that generate magnetic signals, the source locations having a particular resolution, wherein a number of source locations is greater than a number of sensors in the sensor array; and
   generating a source value of signal power for each location in the source grid by fitting to the sensor signal data using the covariance matrix,
   wherein the covariance matrix is time-independent based on time information of the sensor signal data.

2. The method of claim 1, wherein the number of source locations is at least 30 times greater than the number of sensors in the sensor array.

3. The method of claim 2, wherein the number of source locations include at least 10,000 voxels.

4. The method of claim 2, wherein the number of sensors in the sensor array includes at least 250 sensors.

5. The method of claim 1, further comprising:
   producing an image including image features representing the source values at locations mapped to corresponding voxels in a magnetic resonance imaging (MRI) image of the brain.

6. A magnetoencephalography (MEG) source imaging system, comprising:
   a MEG machine including MEG sensors configured to acquire magnetic field signal data including MEG sensor waveform signals from a brain of a subject, the MEG sensor signal data representing magnetic-field signals emitted by the brain of the subject; and
   a processing unit including a processor configured to perform the following:
      determine time-independent signal-related spatial modes from the MEG sensor waveform signals,
      obtain spatial source images of the brain based on the determined time-independent signal-related spatial modes, and
      determine source time-courses of the obtained spatial source images.

7. The MEG source imaging system of claim 6, wherein the processing unit is configured to objectively remove correlated noise from the MEG sensor waveform signals.

8. The MEG source imaging system of claim 6, wherein the processing unit is configured to obtain the spatial source images of the brain based on the determined time-independent signal-related spatial modes based at least on a source imaging map associated with each time-independent signal-related spatial mode.

9. The MEG source imaging system of claim 8, wherein the processing unit is configured to remove bias toward grid nodes that correspond to locations in the brain that generate the MEG sensor waveform signals.

10. The MEG source imaging system of claim 8, wherein the processing unit is configured to remove bias of the spatial source images towards coordinate axes of the spatial source images.

11. The MEG source imaging system of claim 6, wherein the processing unit is configured to determine the source time-courses of the obtained spatial source images based at least on the following:
   an inverse operator matrix constructed based on the obtained spatial source images; and
   application of the constructed inverse operator matrix to the MEG sensor waveform signal.

12. The MEG source imaging system of claim 6, wherein the processing unit is configured to determine a goodness-of-fit to the MEG sensor waveform signal.

13. The MEG source imaging system of claim 12, wherein the processing unit is configured to determine the goodness-of-fit without calculating a predicted MEG sensor waveform signal.

14. The MEG source imaging system of claim 12, wherein the processing unit is configured to determine the goodness-of-fit based at least on measured and predicted sensor spatial-profile matrix.

15. The MEG source imaging system of claim 7, wherein the processing unit is configured to objectively remove the correlated noise from the MEG sensor waveform signals based at least on the following:
   a mother brain noise covariance matrix estimated based on incomplete information;
   a pre-whitening operator constructed based on the estimated mother brain noise covariance matrix;
   a daughter pre-whitened brain noise covariance matrix formed based on application of the pre-whitening operator to daughter brain noise data;
   a plot of square root of eigenvalues of the daughter pre-whitened brain noise covariance matrix;
   a plot of 2nd order derivatives of the square root of the eigenvalues in the daughter pre-whitened brain noise covariance matrix;
   a noise-subspace identified from the plot of 2nd order derivatives; and
   associated threshold values from the plot of square root of the eigenvalues of the daughter pre-whitened brain noise covariance matrix.

16. The MEG source imaging system of claim 6, comprising:
   a magnetic resonance imaging (MRI) machine configured to acquire MRI images to obtain a source grid of the brain.

17. A tangible non-transitory storage medium embodying a computer program product comprising instructions for performing magnetoencephalography (MEG) source imaging when executed by a processing unit, the instructions including:
   determining by the processing unit a covariance matrix based on sensor signal data in the time domain, the sensor signal data representing magnetic-field signals emitted by a brain of a subject and detected by a plurality of MEG sensors in a sensor array surrounding the brain;
   defining by the processing unit a source grid containing source locations within the brain that generate magnetic signals, the source locations having a particular resolution, wherein a number of source locations is greater than a number of sensors in the sensor array; and
   generating a source value of signal power for each location in the source grid by fitting to the sensor signal data using the covariance matrix,
   wherein the covariance matrix is time-independent based on time information of the sensor signal data.

18. The tangible non-transitory storage medium embodying a computer program product comprising instructions for performing magnetoencephalography (MEG) source imaging of claim 17, wherein the number of source locations is at least 30 times greater than the number of sensors in the sensor array.

19. The tangible non-transitory storage medium embodying a computer program product comprising instructions for performing magnetoencephalography (MEG) source imaging of claim 18, wherein the number of source locations include at least 10,000 voxels.

20. The tangible non-transitory storage medium embodying a computer program product comprising instructions for performing magnetoencephalography (MEG) source imaging of claim 18, wherein the number of sensors in the sensor array includes at least 250 sensors.

21. The tangible non-transitory storage medium embodying a computer program product comprising instructions for performing magnetoencephalography (MEG) source imaging of claim 17, the instructions including:
   producing by the processor an image including image features representing the source values at locations mapped to corresponding voxels in a magnetic resonance imaging (MRI) image of the brain.

* * * * *